United States Patent
Pietri et al.

(10) Patent No.: US 11,447,749 B2
(45) Date of Patent: Sep. 20, 2022

(54) METHODS FOR DIFFERENTIATING MESENCHYMAL STEM CELLS

(71) Applicant: BONE THERAPEUTICS S.A., Gosselies (BE)

(72) Inventors: Sandra Pietri, Moha (BE); Xuan Mai Nguyen, Woluwé-Saint-Pierre (BE); Enrico Bastianelli, Rhode-Saint-Genèse (BE); Sabrina Ena, Montigny-le-Tilleul (BE); Pierre-Yves Laruelle, Moutier-sur-Sambre (BE); Isabelle Tytgat, Ophain (BE)

(73) Assignee: Bone Therapeutics S.A., Gosselies (BE)

( * ) Notice: Subject to any disclaimer, the term of this patent is extended or adjusted under 35 U.S.C. 154(b) by 0 days.

(21) Appl. No.: 16/757,033

(22) PCT Filed: Sep. 25, 2018

(86) PCT No.: PCT/EP2018/076030
§ 371 (c)(1),
(2) Date: Apr. 17, 2020

(87) PCT Pub. No.: WO2019/076591
PCT Pub. Date: Apr. 25, 2019

(65) Prior Publication Data
US 2020/0354682 A1 Nov. 12, 2020

(30) Foreign Application Priority Data
Oct. 20, 2017 (EP) .................................... 17197605

(51) Int. Cl.
*C12N 5/0775* (2010.01)
*A61K 35/28* (2015.01)
*A61K 9/00* (2006.01)

(52) U.S. Cl.
CPC ............ *C12N 5/0663* (2013.01); *A61K 35/28* (2013.01); *A61K 9/0019* (2013.01); *C12N 2501/115* (2013.01); *C12N 2501/15* (2013.01); *C12N 2501/91* (2013.01)

(58) Field of Classification Search
CPC .............. C12N 5/0663; C12N 2501/15; C12N 2501/91; C12N 2501/115; A61K 35/28
See application file for complete search history.

(56) References Cited

U.S. PATENT DOCUMENTS

| | | | |
|---|---|---|---|
| 2003/0139410 A1 | 7/2003 | Sugaya et al. | |
| 2010/0105132 A1* | 4/2010 | Totey ................... | C12N 5/0663 435/352 |

FOREIGN PATENT DOCUMENTS

| | | |
|---|---|---|
| CN | 101384707 A | 3/2009 |
| CN | 104204193 A | 12/2014 |
| CN | 105142650 A | 12/2015 |
| JP | 2016067311 A * | 5/2016 ............ C12N 5/077 |
| WO | 2009087213 A1 | 7/2009 |
| WO | 2013121426 A1 | 8/2013 |

OTHER PUBLICATIONS

USP heparin monograph, downloaded from www.fda.gov/drugs/postmarket-drug-safety-information-patients-and-providers/question-and-answers-about-changes-usp-heparin-monograph. p. 1-3 (Year: 2018).*
Kubiczkova et al. TGF-β—an excellent servant but a bad master. Journal of Translational Medicine 2012, 10:183, p. 1-24 (Year: 2012).*
Beederman et al. BMP signaling in mesenchymal stem cell differentiation and bone formation. J Biomed Sci Eng. Aug. 2013 ; 6(8A): 32-52. (Year: 2013).*
Zhou et al. Dominance of SOX9 function over RUNX2 during skeletogenesis. PNAS vol. 103, No. 50; p. 19004-19009 (Year: 2006).*
Lei, Jennifer, et al. "Cell Number and Chondrogenesis in Human Mesenchymal Stem Cell Aggregates Is Affected by the Sulfation Level of Heparin Used as a Cell Coating." Journal of Biomedical Materials Research Part A, vol. 104, No. 7, 2016, pp. 1817-1829. document, 2 pages.
Ling, Ling, et al. "Effect of Heparin on the Biological Properties and Molecular Signature of Human Mesenchymal Stem Cells." Gene, vol. 576, No. 1, 2016, pp. 292-303.
PCT International Preliminary Report on Patentability, Application No. PCT/EP2018/076030 Bone Therapeutics SA, International filing date of Sep. 25, 2018, dated Oct. 7, 2019, Authorized Office M. Paiol Rovira, 15 pages.
PCT International Search Report and Written Opinion; Application No. PCT/EP2018/076030 Bone Therapeutics SA, International filing date of Sep. 25, 2018, dated Jan. 3, 2019, Authorized Office Elena Armandola, 11 pages.
Chinese Office Action and Search Report, Application No. 201880068267.0, Applicant: Bone Therapeutics, S.A., Filed Sep. 25, 2018, National Intellectual Property Administration of the Peoples Republic of China, dated Feb. 23, 2021, 7 pgs (translation).

(Continued)

*Primary Examiner* — Taeyoon Kim
(74) *Attorney, Agent, or Firm* — Patent Law Works, LLP

(57) ABSTRACT

The application discloses a method for obtaining MSC-derived cells with improved transplantation properties from MSC, the method comprising a cell size reduction step, wherein said cell size reduction step is characterized by contacting MSC or MSC-derived cells in vitro or ex vivo with heparin or a derivative or analogue thereof at a concentration of at least 0.01 IU/ml. The application further provides a method for obtaining mesenchymal stem cell-derived cells from mesenchymal stem cells (MSC) comprising contacting MSC in vitro or ex vivo with FGF-2, TGFβ and at least 0.01 IU/ml heparin or a derivative or analogue thereof. The invention also provides the so-obtained cells and cell populations, as well as further products comprising such and uses thereof.

6 Claims, 16 Drawing Sheets

Specification includes a Sequence Listing.

(56) References Cited

OTHER PUBLICATIONS

Yao, Ke et al., Differentiation of rat adipose derived mesenchymal stem cells into motoneurons induced by heparin combined with laminin, China Journal of Modern Medicine, vol. 25, No. 22, Aug. 31, 2015, pp. 11-17, total 7 pgs, with translation.

Hemeda, Hatim, et al. "Heparin Concentration Is Critical for Cell Culture with Human Platelet Lysate." Cytotherapy (Oxford, England), vol. 15, No. 9, 2013, pp. 1174-1181.

Mimura, Sumiyo, et al. "Growth Factor-Defined Culture Medium for Human Mesenchymal Stem Cells." The International Journal of Developmental Biology, vol. 55, No. 2, 2011, pp. 181-187.

Novokhatsky A.S., et al. The Problem of Contamination with Cells and New Approaches to Control of Transplantable Lines, The D.I. Ivanovskii Institute of Virology of the Academy of Medical Sciences of the USSR, Moscow. Jun. 24, 1976; 4: 396-408. English Translation 14 pgs.

Vechkanov E.M., et al., Fundamentals of Cell Engineering: Textbook.—Rostov-on-Don, (2012)136 p.; pp. 15-17, Google Translation of pp. 15-17 only.

French, Dorothy M, et al. "WISP-1 Is an Osteoblastic Regulator Expressed During Skeletal Development and Fracture Repair." The American Journal of Pathology, vol. 165, No. 3, 2004, pp. 855-867.

Komori, Toshihisa. "Regulation of Proliferation, Differentiation and Functions of Osteoblasts by Runx2." International Journal of Molecular Sciences, vol. 20, No. 7, 2019, p. 1694.

Robert, Anny W, et al. "Adipogenesis, Osteogenesis, and Chondrogenesis of Human Mesenchymal Stem/Stromal Cells: A Comparative Transcriptome Approach." Frontiers in Cell and Developmental Biology, vol. 8, 2020, p. 561.

Leonidovich, Petrovsky Yaroslav, "Comparative Characteristics Mesenchymal Stromale Cells Of Human Bone Marrow, Adipose Tissue And Placenta." Allergology and Immunology, Nov. 2009, Thesis abstract for the degree of Candidate of Biological Sciences. 19 pgs. (Machine generated translation).

* cited by examiner

FIGURE 8
Excipient
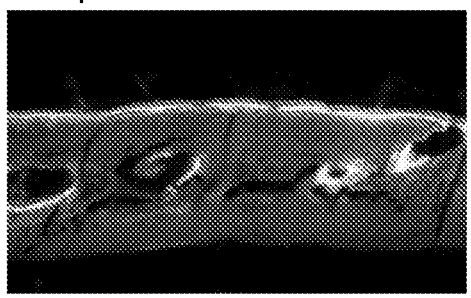 } New bone formation
Bone-forming cells A
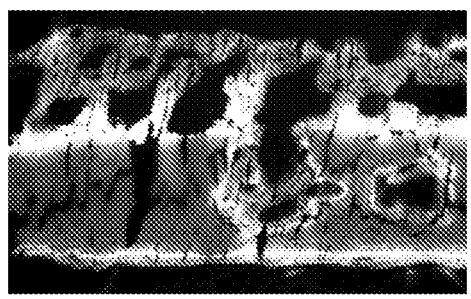 } New bone formation
Bone-forming cells B
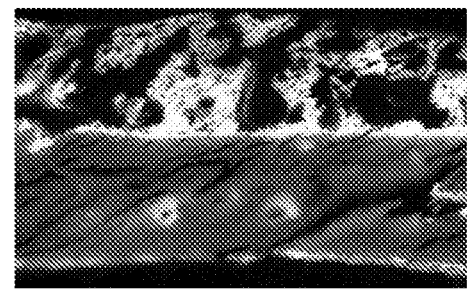 } New bone formation

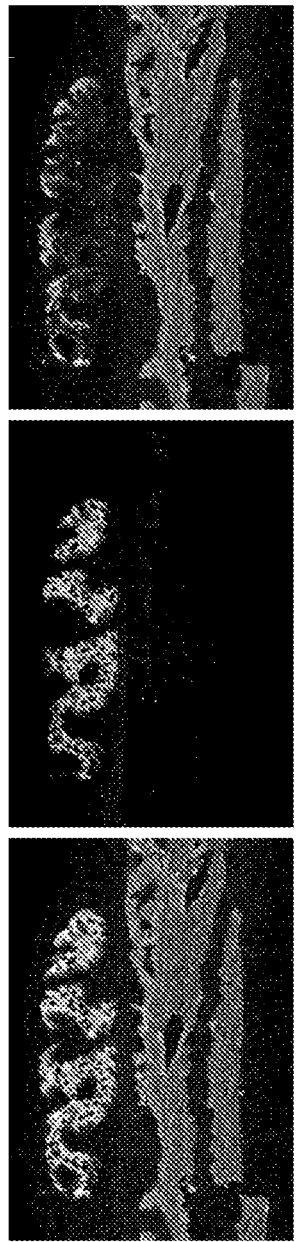

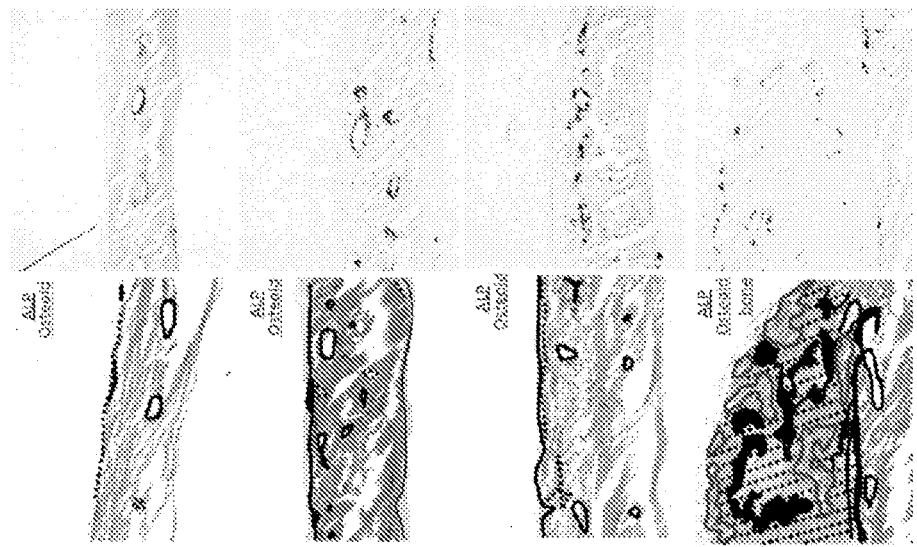
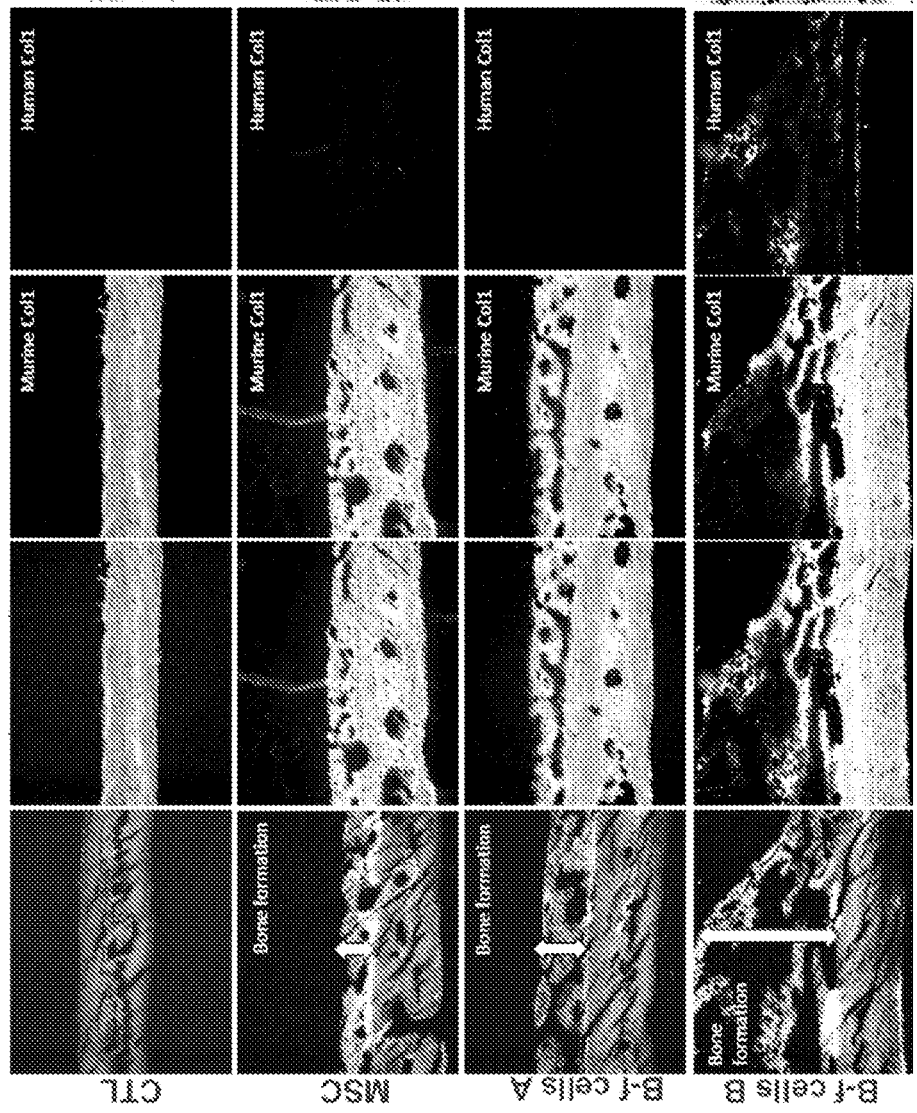

SEQUENCE LISTING

```
<160> NUMBER OF SEQ ID NOS: 26

<210> SEQ ID NO 1
<211> LENGTH: 20
<212> TYPE: DNA
<213> ORGANISM: artificial sequence
<220> FEATURE:
<223> OTHER INFORMATION: Runx2 forward primer

<400> SEQUENCE: 1
ggttccagca ggtagctgag                                              20

<210> SEQ ID NO 2
<211> LENGTH: 20
<212> TYPE: DNA
<213> ORGANISM: artificial sequence
<220> FEATURE:
<223> OTHER INFORMATION: Runx2 reverse primer

<400> SEQUENCE: 2
agacaccaaa ctccacagcc                                              20

<210> SEQ ID NO 3
<211> LENGTH: 20
<212> TYPE: DNA
<213> ORGANISM: artificial sequence
<220> FEATURE:
<223> OTHER INFORMATION: SOX9 forward primer

<400> SEQUENCE: 3
taaaggcaac tcgtacccaa                                              20

<210> SEQ ID NO 4
<211> LENGTH: 20
<212> TYPE: DNA
<213> ORGANISM: artificial sequence
<220> FEATURE:
<223> OTHER INFORMATION: SOX9 reverse primer

<400> SEQUENCE: 4
attctccatc atcctccacg                                              20

<210> SEQ ID NO 5
<211> LENGTH: 20
<212> TYPE: DNA
<213> ORGANISM: artificial sequence
<220> FEATURE:
<223> OTHER INFORMATION: BMP2 forward primer
```

<400> SEQUENCE: 5
ggaacggaca ttcggtcctt                                           20

<210> SEQ ID NO 6
<211> LENGTH: 21
<212> TYPE: DNA
<213> ORGANISM: artificial sequence
<220> FEATURE:
<223> OTHER INFORMATION: BMP2 reverse primer

<400> SEQUENCE: 6
caccatggtc gacctttagg a                                         21

<210> SEQ ID NO 7
<211> LENGTH: 24
<212> TYPE: DNA
<213> ORGANISM: artificial sequence
<220> FEATURE:
<223> OTHER INFORMATION: ALPL forward primer

<400> SEQUENCE: 7
accattccca cgtcttcaca tttg                                      24

<210> SEQ ID NO 8
<211> LENGTH: 22
<212> TYPE: DNA
<213> ORGANISM: artificial sequence
<220> FEATURE:
<223> OTHER INFORMATION: ALPL reverse primer

<400> SEQUENCE: 8
agacattctc tcgttcaccg cc                                        22

<210> SEQ ID NO 9
<211> LENGTH: 21
<212> TYPE: DNA
<213> ORGANISM: artificial sequence
<220> FEATURE:
<223> OTHER INFORMATION: MMP13 forward primer

<400> SEQUENCE: 9
tggaattaag gagcatggcg a                                         21

<210> SEQ ID NO 10
<211> LENGTH: 20
<212> TYPE: DNA
<213> ORGANISM: artificial sequence
<220> FEATURE:
<223> OTHER INFORMATION: MMP13 reverse primer

<400> SEQUENCE: 10
aactcatgcg cagcaacaag                                           20

<210> SEQ ID NO 11
<211> LENGTH: 23
<212> TYPE: DNA
<213> ORGANISM: artificial sequence
<220> FEATURE:
<223> OTHER INFORMATION: CHI3L1 forward primer

<400> SEQUENCE: 11
tgggtctcaa agattttcca aga                                       23

<210> SEQ ID NO 12
<211> LENGTH: 20

<212> TYPE: DNA
<213> ORGANISM: artificial sequence
<220> FEATURE:
<223> OTHER INFORMATION: CHI3L1 reverse primer

<400> SEQUENCE: 12
gctgtttgtc tctccgtcca                                            20

<210> SEQ ID NO 13
<211> LENGTH: 22
<212> TYPE: DNA
<213> ORGANISM: artificial sequence
<220> FEATURE:
<223> OTHER INFORMATION: DCN forward primer

<400> SEQUENCE: 13
aaaatgccca aaactcttca gg                                         22

<210> SEQ ID NO 14
<211> LENGTH: 21
<212> TYPE: DNA
<213> ORGANISM: artificial sequence
<220> FEATURE:
<223> OTHER INFORMATION: DCN reverse primer

<400> SEQUENCE: 14
gccccatttt caattcctga g                                          21

<210> SEQ ID NO 15
<211> LENGTH: 18
<212> TYPE: DNA
<213> ORGANISM: artificial sequence
<220> FEATURE:
<223> OTHER INFORMATION: OCN forward primer

<400> SEQUENCE: 15
aaggtgcagc ctttgtgt                                              18

<210> SEQ ID NO 16
<211> LENGTH: 20
<212> TYPE: DNA
<213> ORGANISM: artificial sequence
<220> FEATURE:
<223> OTHER INFORMATION: OCN reverse primer

<400> SEQUENCE: 16
gctcccagcc attgatacag                                            20

<210> SEQ ID NO 17
<211> LENGTH: 19
<212> TYPE: DNA
<213> ORGANISM: artificial sequence
<220> FEATURE:
<223> OTHER INFORMATION: SPON1 forward primer

<400> SEQUENCE: 17
cctgcggaac tgccaagta                                             19

<210> SEQ ID NO 18
<211> LENGTH: 19
<212> TYPE: DNA
<213> ORGANISM: artificial sequence
<220> FEATURE:
<223> OTHER INFORMATION: SPON1 reverse primer

<400> SEQUENCE: 18
cacgggtgag cccaattct					19

<210> SEQ ID NO 19
<211> LENGTH: 20
<212> TYPE: DNA
<213> ORGANISM: artificial sequence
<220> FEATURE:
<223> OTHER INFORMATION: POSTN forward primer

<400> SEQUENCE: 19
tttgggcacc aaaaagaaat					20

<210> SEQ ID NO 20
<211> LENGTH: 22
<212> TYPE: DNA
<213> ORGANISM: artificial sequence
<220> FEATURE:
<223> OTHER INFORMATION: POSTN reverse primer

<400> SEQUENCE: 20
ttctcatata accagggcaa ca					22

<210> SEQ ID NO 21
<211> LENGTH: 20
<212> TYPE: DNA
<213> ORGANISM: artificial sequence
<220> FEATURE:
<223> OTHER INFORMATION: RPL13 forward primer

<400> SEQUENCE: 21
cataggaagc tgggagcaag					20

<210> SEQ ID NO 22
<211> LENGTH: 20
<212> TYPE: DNA
<213> ORGANISM: artificial sequence
<220> FEATURE:
<223> OTHER INFORMATION: RPL13 reverse primer

<400> SEQUENCE: 22
gccctccaat cagtcttctg					20

<210> SEQ ID NO 23
<211> LENGTH: 20
<212> TYPE: DNA
<213> ORGANISM: artificial sequence
<220> FEATURE:
<223> OTHER INFORMATION: TBP forward primer

<400> SEQUENCE: 23
aacaacagcc tgccaccttta					20

<210> SEQ ID NO 24
<211> LENGTH: 20
<212> TYPE: DNA
<213> ORGANISM: artificial sequence
<220> FEATURE:
<223> OTHER INFORMATION: TBP reverse primer

<400> SEQUENCE: 24
gccataaggc atcattggac					20

<210> SEQ ID NO 25
<211> LENGTH: 19
<212> TYPE: DNA
<213> ORGANISM: artificial sequence

```
<220> FEATURE:
<223> OTHER INFORMATION: HPRT forward primer

<400> SEQUENCE: 25
ccctggcgtc gtgattagt                                                    19

<210> SEQ ID NO 26
<211> LENGTH: 21
<212> TYPE: DNA
<213> ORGANISM: artificial sequence
<220> FEATURE:
<223> OTHER INFORMATION: HPRT reverse primer

<400> SEQUENCE: 26
gtgatggcct cccatctcct t                                                 21
```

METHODS FOR DIFFERENTIATING MESENCHYMAL STEM CELLS

FIELD OF THE INVENTION

The invention relates to methods for expansion and/or differentiation of mesenchymal stem cells (MSC), to MSC-derived cells and cell populations, and to products comprising such cells and cell populations, methods and uses.

BACKGROUND

Transplantation of stem cells capable of undergoing osteogenic differentiation, of cells that are committed towards osteogenic differentiation or of cells with bone-forming ability is a promising avenue for the treatment of bone-related diseases, in particular when the treatment requires production of new bone tissues.

Mesenchymal stem cells (MSC) have been used previously to treat bone disorders (Gangji et al., 2005 Expert Opin Biol Ther 5: 437-42). However, although such relatively undifferentiated stem cells can be transplanted, they are not committed to an osteoblastic lineage and therefore a considerable proportion of so transplanted stem cells may not eventually contribute to the formation of the desired bone tissue. Moreover, the quantity of such stem cells is frequently unsatisfactory.

WO 2007/093431 concerns a method for in vitro expansion of isolated MSC, which yielded cells displaying an osteoblastic phenotype. In said method, human MSC were cultured in the presence of serum or plasma and basic fibroblast growth factor (FGF-2).

WO 2009/087213 concerns a method for obtaining osteoprogenitors, osteoblasts or osteoblast phenotype cells from human MSC in vitro or ex vivo, comprising contacting said MSC with human plasma or serum, FGF-2 and transforming growth factor beta (TGF-β).

There exists a continuous need for novel cells and cell populations useful in among others therapy, such as novel MSC-derived cells and cell populations, and methods for producing the same.

SUMMARY

As corroborated by the experimental section, which illustrates certain representative embodiments of the invention, the inventors realized that the transplantation potential of mesenchymal stem cells (MSC)-derived cells can be considerably augmented when said cells are obtained by contacting MSC or MSC-derived cells in vitro or ex vivo with heparin or a derivative or analogue. More particularly, the inventors found that contacting MSC or MSC-derived cells with heparin or a derivative or analogue, preferably heparin or a derivative or analogue thereof at a concentration of at least 0.01 IU/ml, gives rise to new MSC-cell derived cell populations of which the cells have a standardized, homogeneous, and comparatively small cell size. Such MSC-cell derived cells have improved transplantation properties, such as (i) improved suitability for parenteral (e.g., intravascular, including intravenous) administration, (ii) the possibility to deliver in vivo a tunable and high cell concentration with a limited volume, (iii) a good in vivo safety profile and/or (iv) a good syringeability when delivered parenterally.

Furthermore, the present MSC-derived cells are capable to induce bone formation. In addition to the osteo-inductive properties, the present inventors found that the present MSC-derived cells also display a high osteogenic activity. The osteogenic activity advantageously leads to the occurrence of mineralized nodules produced through endochondral ossification.

Hence, in an aspect, the invention provides a method for obtaining MSC-derived cells with improved transplantation properties from MSC, the method comprising a size reduction step, wherein said size reduction step is characterized by contacting MSC or MSC-derived cells in vitro or ex vivo with heparin or a derivative or analogue thereof at a concentration of at least 0.01 IU/ml.

In a further aspect the invention provides a method for obtaining MSC-derived cells from MSC comprising contacting MSC in vitro or ex vivo with FGF-2, TGFβ and heparin or a derivative or analogue thereof at a concentration of at least 0.01 IU/ml.

In a further aspect, the invention provides a method for obtaining MSC-derived cells from MSC comprising contacting MSC in vitro or ex vivo with FGF-2, TGFβ and heparin or a derivative or analogue thereof, whereby at least 60% of the MSC-derived cells in suspension have a diameter equal to or less than 25 μm ($D_{60} \leq 25$ μm) and wherein at most 5% of the MSC-derived cells in suspension have a diameter of more than 35 μM.

In another aspect, the invention provides a population of MSC-derived cells obtainable by in vitro or ex vivo expansion of MSC, whereby at least 60% of the MSC-derived cells in suspension have a diameter equal to or less than 25 μm ($D_{60} \leq 25$ μm) and wherein at most 5% of the MSC-derived cells in suspension have a diameter of more than 35 μM.

In another aspect, the invention provides a pharmaceutical composition comprising the population of MSC-derived cells as taught herein.

In another aspect, the invention provides the population of MSC-derived cells or the pharmaceutical composition as taught herein for use as a medicament.

These and further aspects and preferred embodiments of the invention are described in the following sections and in the appended claims. The subject-matter of the appended claims is hereby specifically incorporated in this specification.

BRIEF DESCRIPTION OF THE FIGURES

FIG. 8 illustrates the neo bone formation on a murine bone calvaria coronal section evidenced by murine and human calcium-binding fluorochromes, 2 weeks after administration of excipient alone (control condition), MSC-derived bone-forming cells A (generated with FGF-2 and TGFβ1) or MSC-derived bone-forming cells B (generated with FGF-2, TGFβ1 and heparin).

FIG. 10 illustrates anti-murine and anti-human type I collagen double immunostaining (immunofluorescence) performed on murine bone calvaria coronal sections 2 weeks after administration of MSC-derived bone-forming cells B (generated with FGF-2, TGFβ1 and heparin).

FIG. 10a illustrates anti-human and anti-murine type I collagen double immunostaining (merge) while FIGS. 10b and 10c show anti-human and anti-murine type I collagen immunostaining respectively.

FIG. 12 illustrates histology staining of murine bone calvaria coronal sections, 2 weeks after administration of excipient alone, MSC, MSC-derived bone-forming cells A generated with FGF-2 and TGFβ1 (b-f cells A), or MSC-derived bone-forming cells B generated with FGF-2, TGFβ1 and heparin (b-f cells B). (A) calcium-binding fluorochromes were sequentially injected intraperitoneally (alizarin-red→calcein green→calcein blue→tetracycline) to evidence the neo-bone formation (arrows) and evaluate the dynamic of the bone-formation; (B) immunofluorescence (IF) human+murine type I collagen; (C) IF murine type I collagen; (D) IF human type I collagen. Anti-human and anti-murine type I collagen double immunofluorescence was performed to allow the detection of human and murin type I collagen secreted by the bone matrix; (E) ALP+Goldner staining: ALP: detection of the osteoblast activity in black (full lines and areas), Masson's trichrome Goldner: detection of the osteoid (unmineralized bone tissue) in black dotted lines, mineralized bone in dark grey lines; (F) tartrate-resistant acid phosphatase (TRAP): detection of the osteoclast activity in dark grey/black.

DETAILED DESCRIPTION

Figure 1A:
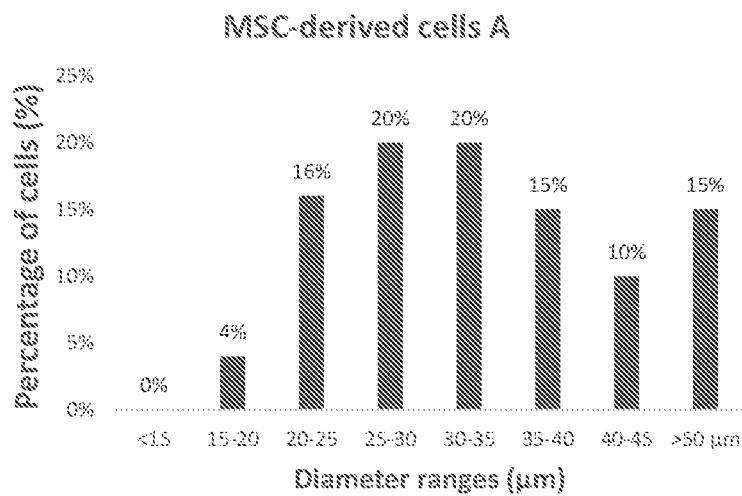
FIG. 1 illustrates the cell size of MSC-derived cells, particularly MSC-derived bone-forming cells, generated with fibroblast growth factor-2 (FGF-2) and transforming growth factor beta 1 (TGFβ1) (A) and MSC-derived bone-forming cells generated with FGF-2, TGFβ1 and heparin (B).

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

As corroborated by the experimental section, which illustrates certain representative embodiments of the invention, the inventors identified a method for obtaining MSC-derived cells or a population of MSC-derived cells with an increased transplantation potential. More particularly, the inventors have surprisingly found that when contacting MSC or MSC-derived cells with a heparin or a derivative or analogue thereof, preferably heparin or a derivative or analogue thereof at a concentration of at least 0.01 IU/ml, a new MSC-derived cell population with a standardized, homogenous, small size, could be obtained. In certain embodiments, MSC or MSC-derived cells are contacted with a combination of FGF-2, TGFβ and heparin or a derivative or analogue thereof, preferably heparin or a derivative or analogue thereof at a concentration of at least 0.01 IU/ml. Such a standardized, homogeneous, small size represents improved transplantation properties such as (i) the potential of parenteral (e.g., intravascular, including intravenous) administration of said MSC-derived cells, (ii) the possibility to deliver in vivo a tunable and high cell concentration with a limited volume, (iii) a good in vivo safety profile and/or (iv) a good syringeability when delivered parenterally. Accordingly, a first aspect provides a method for obtaining MSC-derived cells from MSC comprising contacting MSC in vitro or ex vivo with FGF-2, TGFβ and heparin or a derivative or analogue thereof at a concentration of at least 0.01 IU/ml.

The term "mesenchymal stem cell" or "MSC" as used herein refers to an adult, mesoderm-derived stem cell that is capable of generating cells of mesenchymal lineages, typically of two or more mesenchymal lineages, more typically three or more mesenchymal lineages, e.g., osteochondroblastic (bone and cartilage), osteoblastic (bone), chondroblastic (cartilage), myocytic (muscle), tenocytic (tendon), fibroblastic (connective tissue), adipocytic (fat) and stromogenic (marrow stroma) lineage. MSC may be isolated from a biological sample, preferably a biological sample of a human subject, e.g., bone marrow, trabecular bone, blood, umbilical cord, placenta, foetal yolk sac, skin (dermis), specifically foetal and adolescent skin, periosteum, dental pulp, tendon and adipose tissue. The term "biological sample" or "sample" as used herein refers to a sample obtained from a biological source, e.g., from an organism, such as an animal or human subject, cell culture, tissue sample, etc. A biological sample of an animal or human subject refers to a sample removed from an animal or human subject and comprising cells thereof. The biological sample of an animal or human subject may comprise one or more tissue types and may comprise cells of one or more tissue types. Methods of obtaining biological samples of an animal or human subject are well known in the art, e.g., tissue biopsy or drawing blood. Human MSC, their isolation, in vitro expansion, and differentiation, have been described in, e.g., U.S. Pat. Nos. 5,486,359; 5,811,094; 5,736,396; 5,837,539; or U.S. Pat. No. 5,827,740. Any MSC described in the art and isolated by any method described in the art may be suitable in the present method. In particular, MSC may be defined as displaying the capacity for in vitro trilineage mesenchymal differentiation into osteoblasts, adipocytes, and chondroblasts (Dominici et al., 2006, vol. 8, 315).

The term "MSC" also encompasses the progeny of MSC, e.g., progeny obtained by in vitro or ex vivo proliferation (propagation/expansion) of MSC obtained from a biological sample of an animal or human subject.

The term "stem cell" refers generally to an unspecialized or relatively less specialized and proliferation-competent cell, which is capable of self-renewal, i.e., can proliferate without differentiation, and which or the progeny of which can give rise to at least one relatively more specialized cell type. The term encompasses stem cells capable of substantially unlimited self-renewal, i.e., wherein the progeny of a stem cell or at least part thereof substantially retains the unspecialized or relatively less specialized phenotype, the differentiation potential, and the proliferation capacity of the mother stem cell, as well as stem cells which display limited self-renewal, i.e., wherein the capacity of the progeny or part thereof for further proliferation and/or differentiation is demonstrably reduced compared to the mother cell. By means of example and not limitation, a stem cell may give rise to descendants that can differentiate along one or more lineages to produce increasingly relatively more specialized cells, wherein such descendants and/or increasingly relatively more specialized cells may themselves be stem cells as defined herein, or even to produce terminally differentiated cells, i.e., fully specialized cells, which may be post-mitotic.

The term "adult stem cell" as used herein refers to a stem cell present in or obtained from (such as isolated from) an organism at the foetal stage or preferably after birth (e.g., particularly but without limitation for a human organism, at least one month of age after birth, e.g., at least 2 months, at least 3 months, e.g., at least 4 months, at least 5 months, e.g., at least 6 months of age after birth, such as, for example, 1 year or more, 5 years or more, at least 10 years or more, 15 years or more, 20 years or more, or 25 years or more of age after birth), such as for example after achieving adulthood. By means of example, adult stem cells can be obtained from human subjects which would otherwise be described in the conventional terms "infant", "child", "youth", "adolescent" or "adult".

Preferable MSC have the potential of generating cells of at least the osteochondroblastic lineage, such as, e.g., cells of the osteoblastic lineage, such as, e.g., osteochondroprogenitors and/or osteoprogenitors and/or pre-osteoblasts and/or osteoblasts and/or osteocytes, and/or of the chondroblastic lineage, such as, e.g., osteochondroprogenitors and/or chondroprogenitors and/or pre-chondroblasts and/or chondroblasts and/or chondrocytes.

Further preferable MSC have the potential of generating cells of at least the osteoblastic (bone) lineage, such as, e.g., osteochondroprogenitors and/or osteoprogenitors and/or pre-osteoblasts and/or osteoblasts and/or osteocytes, etc.; or of at least the chondroblastic (cartilage) lineage, such as, e.g., osteochondroprogenitors and/or chondroprogenitors and/or pre-chondroblasts and/or chondroblasts and/or chondrocytes; fibroblastic (connective tissue) lineage, such as, e.g., fibroblasts, fibrocytes; or of at least synoviocytes (synovial fluid); or tenocytes etc.

Except when noted, "subject" or "patient" are used interchangeably and refer to animals, preferably vertebrates, more preferably mammals, and specifically includes human patients and non-human mammals. Preferred patients are human subjects. Animal subjects include prenatal forms of animals, such as, e.g., fetuses. Human subjects may include fetuses, and not embryos.

In an embodiment, MSC may be obtained from a healthy subject, which may help to ensure the functionality of MSC-derived cells obtained from said MSC.

In another embodiment, MSC are obtained from a human subject who is in need of transplantation of MSC-derived cells.

In certain embodiments of the products or the methods as taught herein, the MSC or MSC-derived cells may be allogeneic to the subject to be treated. The terms "allogeneic" or "homologous" with reference to MSC or MSC-derived cells denotes that the MSC or MSC-derived cells are obtained from one or more (pooled) subjects other than the subject to be contacted or treated with the MSC-derived cells.

In certain embodiments of the products or the methods as taught herein, the MSC or MSC-derived cells may be autologous to the subject to be treated. The term "autologous" with reference to MSC or MSC-derived cells denotes that the MSC or MSC-derived cells are obtained from the same subject to be contacted or treated with the MSC-derived cells.

In certain embodiments of the products or the methods as taught herein, the MSC or MSC-derived cells may comprise a mixture of autologous and allogeneic (i.e., homologous) MSC or MSC-derived cells as defined above. Preferably, the MSC or MSC-derived cells are allogeneic to the subject to be treated.

The term "mesenchymal stem cell-derived cells" or "MSC-derived cells" as used herein refer to cells of mesenchymal lineage (e.g., osteochondroblastic (bone and cartilage), osteoblastic (bone), chondroblastic (cartilage), myocytic (muscle), tenocytic (tendon), fibroblastic (connective tissue), adipocytic (fat), or stromogenic (marrow stroma) lineage) obtained by differentiation of MSC, in particular obtained by in vitro (including ex vivo) differentiation of MSC.

Differentiation of MSC may involve culturing MSC under conditions capable of inducing the differentiation of MSC towards the desired cell type, more typically culturing MSC in a medium comprising one or more agents (e.g., growth factors) capable of inducing the differentiation of MSC towards the desired cell type. Protocols for differentiation of MSC are known per se (see, inter alia, WO 2007/093431; and further REGER, R. L. et al. 'Differentiation and Characterization of Human MSCs'. In: Mesenchymal Stem Cells: Methods and Protocols (Methods in Molecular Biology), Edited by D. J. Prockop et al. Humana Press, 2008, Vol. 449, p. 93-107; VERMURI, M. C. et al. (Eds.). Mesenchymal Stem Cell Assays and Applications (Methods in Molecular Biology). Humana Press, 2011, Vol. 698, especially pages 201 to 352).

The term "growth factor" as used herein refers to a biologically active substance which influences proliferation, growth, differentiation, survival and/or migration of various cell types, and may affect developmental, morphological and functional changes in an organism, either alone or when modulated by other substances. A growth factor may typically act by binding, as a ligand, to a receptor (e.g., surface or intracellular receptor) present in cells responsive to the growth factor. A growth factor herein may be particularly a proteinaceous entity comprising one or more polypeptide chains. By means of example and not limitation, the term "growth factor" encompasses the members of the fibroblast growth factor (FGF) family, bone morphogenetic protein (BMP) family, platelet-derived growth factor (PDGF) family, transforming growth factor beta (TGFβ) family, nerve growth factor (NGF) family, epidermal growth factor (EGF) family, insulin-like growth factor (IGF) family, growth differentiation factor (GDF) family, hepatocyte growth factor (HGF) family, hematopoietic growth factors (HeGFs), platelet-derived endothelial cell growth factor (PD-ECGF), angiopoietin, vascular endothelial growth factor (VEGF) family, glucocorticoids, and the like. The skilled person will understand that the growth factor or combination of growth factors may be any growth factor or combination of growth factors known of being capable of inducing differentiation of MSC towards a desired cell type. The skilled person will appreciate that in vitro methods for inducing differentiation of MSC towards a desired cell type (e.g., towards cells of osteochondroblastic, osteoblastic, or chondroblastic lineage) may result in a substantially pure (i.e., composed primarily of) cell population of the desired cell type. Without limitation, so-derived cell population may contain at least 90% (by number) of the desired cell type, such as, e.g., ≥91%, ≥92%, ≥93%, ≥94%, ≥95%, ≥96%, ≥97%, ≥98%, ≥99%, or 100% of the desired cell type.

In particular embodiments, the MSC-derived cells are of osteochondroblastic lineage (bone and cartilage), osteoblastic lineage (bone), such as, e.g., osteochondroprogenitors and/or osteoprogenitors and/or pre-osteoblasts and/or osteoblasts and/or osteocytes, etc.; chondroblastic (cartilage) lineage, such as, e.g., osteochondroprogenitors and/or chondroprogenitors and/or pre-chondroblasts and/or chondroblasts and/or chondrocytes; adipogenic (fat); myogenic (muscle); tenogenic (tenocytes) lineage; fibroblastic (connective tissue) lineage, such as, e.g., fibroblasts, fibrocytes; or synovial (synovial fluid) lineage.

In particular embodiments, the MSC-derived cells are of osteochondroblastic lineage. The recitation "MSC-derived cells of the osteochondroblastic lineage" as used herein may refer to progenitor cells which have the ability to differentiate into cells of the osteoblastic lineage, such as osteochondroprogenitors, osteoprogenitors and/or pre-osteoblasts and/or osteoblasts and/or osteocytes, etc., or into cells of the chondroblastic lineage, such as osteochondroprogenitors, chondroprogenitors and/or pre-chondroblasts and/or chondroblasts and/or chondrocytes. The skilled person will understand that the progenitor cells will either differentiate into cells of the osteoblastic lineage (e.g., pre-osteoblasts or osteoblasts), or into cells of the chondroblastic lineage (e.g., pre-chondroblasts or chondroblasts) depending on conditions they are exposed to, such as physical factors, and/or chemical or biological components, such as growth factors.

In particular embodiments, the MSC-derived cells are MSC-derived cells of the osteoblastic or chondroblastic lineage. In preferred embodiments, the MSC-derived cells are MSC-derived cells of the osteoblastic lineage. In more preferred embodiments, the MSC-derived cells are osteoprogenitors, pre-osteoblasts, osteoblasts, or osteocytes.

In certain particularly preferred embodiments, the recitation "MSC-derived cells of the osteoblastic lineage" or "MSC-derived bone-forming cells" may equally refer to cell types having an osteoblastic phenotype, and that can contribute to, or are capable of developing to cells which can contribute to, the formation of bone material or bone matrix, such as osteochondroprogenitors, osteoprogenitors, pre-osteoblasts, osteoblasts, or osteocytes, or mixtures thereof. As used herein, "osteoprogenitors" may particularly comprise early and late osteoprogenitors. Even more preferably, "MSC-derived cells of the osteoblastic lineage" or "MSC-derived bone-forming cells" may equally refer to osteochondroprogenitors, osteoprogenitors, pre-osteoblasts, or osteoblasts, or mixtures thereof, yet more preferably the phrase may refer to osteochondroprogenitors or pre-osteoblasts or osteoblasts, or mixtures thereof, such as in certain examples the phrase may refer to pre-osteoblasts, or in certain other examples the phrase may refer to osteoblasts. All these terms are well-known per se.

By means of further guidance and not limitation, osteoprogenitors, pre-osteoblasts and osteoblasts, as well as cell populations comprising osteoprogenitors pre-osteoblasts and/or osteoblasts may display the following characteristics:

a) the cells comprise expression of Runt-related transcription factor 2 (Runx2), a multifunctional transcription factor that regulates osteoblast differentiation and the expression of many extracellular matrix protein genes during osteoblast differentiation;

b) the cells comprise expression of at least one of the following: alkaline phosphatase (ALP), more specifically ALP of the bone-liver-kidney type; and more preferably also comprise expression of one or more additional bone markers such as osteocalcin (OCN, BGLAP), procollagen type 1 amino-terminal propeptide (P1NP), osteonectin (ON, SPARC), osteopontin (OPST, SPP1, OPN) and/or bone sialoprotein (BSP), and/or one or more additional bone matrix proteins such as decorin and/or osteoprotegerin (OPG);

c) the cells substantially do not express CD45 (e.g., less than about 10%, preferably less than about 5%, more preferably less than about 2% of the cells may express CD45);

d) the cells show evidence of ability to mineralize the external surroundings, or synthesize calcium-containing extracellular matrix (e.g., when exposed to osteogenic medium; see Jaiswal et al. J Cell Biochem, 1997, vol. 64, 295-312). Calcium accumulation inside cells and deposition into matrix proteins can be conventionally measured for example by culturing in $^{45}Ca^{2+}$, washing and re-culturing, and then determining any radioactivity present inside the cell or deposited into the extracellular matrix (U.S. Pat. No. 5,972,703), or using an alizarin red-based mineralization assay (see, e.g., Gregory et al. Analytical Biochemistry, 2004, vol. 329, 77-84);

e) the cells substantially do not differentiate towards neither of cells of adipocytic lineage (e.g., adipocytes) or chondroblastic lineage (e.g., chondroblasts, chondrocytes). The absence of differentiation towards such cell lineages may be tested using standard differentiation inducing conditions established in the art (e.g., see Pittenger et al. Science, 1999, vol. 284, 143-7), and assaying methods (e.g., when induced, adipocytes typically stain with oil red O showing lipid accumulation; chondrocytes typically stain with alcian blue or safranin-orange). Substantially lacking propensity towards adipogenic and/or chondrogenic differentiation may typically mean that less than 20%, or less than 10%, or less than 5%, or less than 1% of the tested cells would show signs of adipogenic or chondrogenic differentiation when applied to the respective test.

By means of example but without limitation, suitable cell surface markers to evaluate cell identity of MSC-derived cells of osteochondroblastic or osteoblastic lineage may include CD105, CD90, CD73, CD45 and ALP, particularly ALP of the bone-liver-kidney type. These cell surface markers can for instance be detected by commercially available monoclonal antibodies, such as fluorochrome-labelled monoclonal antibodies allowing for cell detection by flow cytometry. In particular, CD105, CD90, and CD73 are mesenchymal markers, and are typically highly expressed by MSC-derived cells of osteoblastic lineage; CD45 is a hematopoietic marker, and is typically substantially absent from MSC-derived cells of osteoblastic lineage; ALP is a marker of pre-osteoblasts and osteoblasts, and is typically expressed by a substantial fraction of MSC-derived cells of osteochondroblastic or osteoblastic lineage.

In certain embodiments, the MSC-derived cells of osteochondroblastic or osteoblastic lineage may have osteoinductive properties.

The terms "osteoinductive properties", "osteoinductive potential" or "osteoinductive activity" as used herein refers to the ability of cells to attract other bone-matrix-secreting cells and/or to induce the (trans)differentiation of other cells into bone-matrix-secreting cells.

For instance, cell potency of MSC-derived cells of osteochondroblastic or osteoblastic lineage can be determined by measuring bone-forming properties of such cells. The ability of MSC-derived cells of osteochondroblastic or osteoblastic lineage to induce bone formation can be measured in vivo for example by evaluating the thickness of newly mineralized bone after administration of the cells to mice by subcutaneous injection over the calvaria. The ability of MSC-derived cells of osteochondroblastic or osteoblastic lineage to induce bone formation can also be measured for example through the alkaline phosphatase (ALP) activity assessment by an ALP substrate staining.

In certain embodiments, the MSC-derived cells of osteochondroblastic or osteoblastic lineage may have osteogenic properties.

For instance, cell potency of MSC-derived cells of osteochondroblastic or osteoblastic lineage can be determined by measuring osteogenic activity of such cells. The osteogenic activity of human MSC-derived cells of osteochondroblastic or osteoblastic lineage can be measured in vivo for example by determining the presence of at least one mineralized nodule of human origin after administration of the cells to mice by subcutaneous injection over the calvaria. The osteogenic activity of MSC-derived cells of human osteochondroblastic or osteoblastic lineage can be measured in vivo for example by evaluating the thickness of newly mineralized nodules of human origin after administration of the cells to mice by subcutaneous injection over the calvaria.

For instance, human MSC-derived cells of osteochondroblastic or osteoblastic lineage, such as of $2.5 \times 10^6$ cells formulated in 100 µl excipient, can be administered to nude mice by a single subcutaneous administration over the calvaria bone. To label bone neo-formation over time, calcium-binding fluorochromes such as alizarin red (red), calcein (green), calcein (blue) and tetracycline (yellow) can be sequentially administered to mice intraperitoneal injection 3 days before and 4, 8, and 12 days after cell administration of the MSC-derived cells, respectively. Mice can be euthanized 2 weeks after cell administration and the calvaria of each mouse can be harvested to assess bone formation properties by histomorphometry (e.g., quantification of bone formation). The initial and final thicknesses of the calvaria can be used to calculate the percentage of neo-bone formation following administration of the cells. Furthermore, bone formation properties can also be assessed by immunofluorescence (e.g., murine or human origin of the bone formation). Osteoblastic activity can be assessed on calvaria sections using ALP enzymatic activity detection method. Osteoclastic activity can be assessed on calvaria sections using TRAP enzymatic activity detection methods. The status of mineralization of the neo-formed bone can be assessed using Masson Trichrome Goldner staining on the calvaria sections stained with ALP for instance using commercially available kits (e.g., Bio-Optica®). Cartilage formation can be assessed using safranin-orange staining on calvaria sagittal paraffin sections.

The term "osteogenic potential" as used herein refers to the ability of cells to (trans)differentiate into bone-matrix-secreting cells or to the ability of cells to secrete bone matrix (i.e., without the need of a (trans)differentiation step), in vivo, and optionally in vitro. The term encompasses the ability of cells to form bone tissue by intramembranous ossification or endochondral ossification. The ability of the cells to form bone tissue by intramembranous ossification typically represents the ability of the cells to form bone tissue without the need of a calcified cartilage matrix as a template. The ability of the cells to form bone tissue by endochondral ossification typically represents the ability of the cells to form bone tissue by first forming a calcified cartilage matrix and subsequently using said calcified cartilage matrix as a template for bone tissue formation. The term does not encompass the osteoinductive potential of cells, which represents the ability of cells to attract other bone-matrix-secreting cells and/or to induce the (trans) differentiation of other cells into bone-matrix-secreting cells. The skilled person will understand that the MSC-derived cells of osteochondroblastic or osteoblastic lineage as intended herein may have both osteogenic and osteoinductive potential.

In certain embodiments, the MSC-derived cells of osteochondroblastic or osteoblastic lineage may have both osteoinductive and osteogenic properties. Advantageously, the MSC-derived cells of osteochondroblastic or osteoblastic lineage as taught herein, upon transplantation into a subject in need thereof, allow bone neo-formation which exceeds bone neo-formation as compared to transplantation with MSCs or MSC-derived cells obtained by prior art methods.

By means of example but without limitation, suitable cell surface markers to evaluate cell identity of MSC-derived cells of osteochondroblastic or osteoblastic lineage may include CD73, CD105, CD10, and CD44. These cell surface markers can for instance be detected by commercially available monoclonal antibodies, such as fluorochrome-labelled monoclonal antibodies allowing for cell detection by flow cytometry. In particular, CD73 and CD105 are mesenchymal markers; CD44 is an adhesion marker; and CD10 is an osteochondroblastic marker which are typically expressed by a high fraction of MSC-derived cells of osteochondroblastic or osteoblastic lineage. The quantity of CD73 on the cell surface of MSC-derived cells of osteochondroblastic or osteoblastic lineage is typically high; the quantity of CD105 on the cell surface of MSC-derived cells of osteochondroblastic or osteoblastic lineage is typically low; and the quantity of CD44 on the cell surface of MSC-derived cells of osteochondroblastic or osteoblastic lineage is typically high.

In particular embodiments, substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage are positive for CD73, CD63 and CD166; substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage are negative for CD45.

In particular embodiments, substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage obtained by the methods for obtaining MSC-derived cells osteochondroblastic or osteoblastic lineage from MSC are positive for CD90, CD105, CD73, CD63 and CD166.

In particular embodiments, substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage obtained by the methods for obtaining MSC-derived cells osteochondroblastic or osteoblastic lineage from MSC are positive for CD90, CD105, CD73, CD63 and CD166; substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage are negative for CD45, CD14 and CD19.

In particular embodiments, substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage are negative for CD45, CD14 and CD19.

In particular embodiments, substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage are negative for CD45, CD34 and CD3.

In particular embodiments, substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage are negative for CD45, CD34, CD3, CD14 and CD19.

In particular embodiments, substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage obtained by the methods for obtaining MSC-derived cells osteochondroblastic or osteoblastic lineage from MSC are positive for any one or more, such as one, two, three or all, of CD73, CD105, CD10 or CD44 (i.e., express any one or more, such as one, two, three or all, of CD73, CD105, CD10 or CD44 on the cell surface). Preferably, substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage obtained by the methods for obtaining MSC-derived cells osteochondroblastic or osteoblastic lineage from MSC are positive for CD73, CD105, CD10 and CD44 (i.e., express CD73, CD105, CD10 and CD44 on the cell surface).

In particular embodiments, the MSC-derived cells of osteochondroblastic or osteoblastic lineage obtained by the methods for obtaining MSC-derived cells osteochondroblastic or osteoblastic lineage from MSC have any one or more of a normalized Median of Fluorescence Intensity (nMFI) for CD73 ($nMFI_{CD73}$) of at least 500, a nMFI for CD44 ($nMFI_{CD44}$) of at least 100 or a nMFI for CD105 ($nMFI_{CD105}$) of at most 150. For instance, the MSC-derived cells of osteochondroblastic or osteoblastic lineage have any one or more of a $nMFI_{CD73}$ of at least 550, at least 600, at least 650, at least 700, at least 750, at least 800, at least 850 or at least 900; a $nMFI_{CD44}$ of at least 110, at least 120, at least 130, at least 140, at least 150, at least 200, at least 250, at least 300 or at least 350; or a $nMFI_{CD105}$ of at most 180, at most 170, at most 160, at most 150, at most 140, at most 130, at most 120, at most 110 or at most 100. Preferably, the MSC-derived cells of osteochondroblastic or osteoblastic lineage obtained by the methods for obtaining MSC-derived cells osteochondroblastic or osteoblastic lineage from MSC have a $nMFI_{CD73}$ of at least 500, a $nMFI_{CD44}$ of at least 100, and a $nMFI_{CD105}$ of at most 150.

In particular embodiments, substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage obtained by the methods for obtaining MSC-derived cells osteochondroblastic or osteoblastic lineage from MSC are positive for any one or more, such as one, two, three or all, of CD73, CD105, CD10 or CD44 (i.e., express any one or more, such as one, two, three or all, of CD73, CD105, CD10 or CD44 on the cell surface), and the MSC-derived cells of osteochondroblastic or osteoblastic lineage obtained by the methods for obtaining MSC-derived cells osteochondroblastic or osteoblastic lineage from MSC have any one or more of a $nMFI_{CD73}$ of at least 500, a $nMFI_{CD44}$ of at least 100 or a $nMFI_{CD105}$ of at most 150. Preferably, substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage obtained by the methods for obtaining MSC-derived cells osteochondroblastic or osteoblastic lineage from MSC are positive for CD73, CD105, CD10 and CD44 (i.e., express CD73, CD105, CD10 and CD44 on the cell surface), and the MSC-derived cells of osteochondroblastic or osteoblastic lineage obtained by the methods for obtaining MSC-derived cells osteochondroblastic or osteoblastic lineage from MSC have a $nMFI_{CD73}$ of at least 500, a $nMFI_{CD44}$ of at least 100, and a $nMFI_{CD105}$ of at most 150.

The "normalized Median of Fluorescence Intensity" or "nMFI" as used herein refers to the ratio of the MFI of the whole analyzed cell population labeled with one or more fluorochrome-conjugated antibodies ($MFI_{marker\_channel}$) to the MFI of the cell population labeled with one or more fluorochrome-conjugated isotype control antibodies ($MFI_{isotype\_channel}$), such as immunoglobulin G (IgG) control conjugated with a fluorochrome such as fluorescein isothiocyanate (FITC), allophycocyanin (APC) or phycoerythrin (PE). nMFI results are proportional to the quantity of markers present on cell surface of a population of interest. The (n)MFI is typically linked to the wavelength at which the emission of the fluorescent signal is measured.

The recitations "a nMFI for CD73" or "$nMFI_{CD73}$" as used herein refers to the ratio of the MFI of the whole analyzed cell population labeled with an APC-conjugated antibody against CD73 (e.g., BD Biosciences®, Cat No.: 560847) to the MFI of the cell population labeled with IgG control conjugated with APC (e.g., BD Biosciences®, Cat No.: 555751). Preferably, the $nMFI_{CD73}$ is measured with an excitation wavelength of 633 nm and an emission wavelength of 660 nm for APC.

The recitations "a nMFI for CD44" or "$nMFI_{CD44}$" as used herein refers to the ratio of the MFI of the whole analyzed cell population labeled with PE-conjugated antibody against CD44 (e.g., BD Biosciences®, Cat No.: 550989) to the MFI of the cell population labeled with IgG control conjugated with PE (e.g., BD Biosciences®, Cat No.: 556650). Preferably, the $nMFI_{CD44}$ is measured with an excitation wavelength of 488 nm and an emission wavelength of 580 nm for PE.

The recitation "a nMFI for CD105" or "$nMFI_{CD105}$" as used herein refers to the ratio of the MFI of the whole analyzed cell population labeled with APC-conjugated antibodies against CD105 (e.g., BD Biosciences®, Cat No.: 562408) to the MFI of the cell population labeled with IgG control conjugated with APC (e.g., BD Biosciences®, Cat N: 555751). Preferably, the $nMFI_{105}$ is measured with an excitation wavelength of 633 nm and an emission wavelength of 660 nm for APC.

In certain embodiments, the MSC-derived cells of osteochondroblastic or osteoblastic lineage may comprise one or more of:

increased expression of a gene encoding an osteochondroblastic marker selected from the group consisting of RUNX2, SOX9, ZNF521, ALPL, BMP2, OPG, POSTN, CHI3L1, MMP13, CADM1, CX43, CD10, and WISP1;

increased expression of a gene encoding a bone or cartilage matrix protein selected from DCN or SPON1;

decreased expression of the gene DKK1 encoding an osteochondrogenesis inhibitor; and/or decreased expression of a gene encoding a proliferation marker selected from K67 or PCNA, as compared to the expression of the respective gene in MSC.

In certain embodiments, the expression of a gene encoding an apoptosis-related marker selected from BCL2 or BAX may be similar for MSC-derived cells of osteochondroblastic or osteoblastic lineage and MSC.

In certain embodiments, the MSC-derived cells of osteochondroblastic or osteoblastic lineage comprise one or more of:
increased expression of the gene PPARG encoding a protein involved in adipogenesis;
increased expression of a gene encoding an osteochondroblastic protein selected from CD73 or BMP2; and/or
decreased expression of a gene encoding an osteochondroblastic protein selected from the group consisting of COL1A1, BGN, SPARC, ALPL, and BCL2,
as compared to the expression of the respective gene in bone-forming cells generated by a method which is substantially the same in substantially all parameters than the method as taught herein for obtaining MSC-derived cells from MSC, other than the presence vs. absence of heparin or its analogue or derivative.

In certain embodiments, the expression of a gene encoding a protein in the MSC-derived cells of osteochondroblastic or osteoblastic lineage may be increased (i.e., enhanced) by at least about 1% relative to (i.e., compared with) (i.e., the expression of a gene encoding a protein in the MSC-derived cells of osteochondroblastic or osteoblastic lineage may be at least about 1.01-fold) the expression of said gene in a corresponding control cell as defined herein. For example, the expression of a gene encoding a protein in the MSC-derived cells of osteochondroblastic or osteoblastic lineage may be increased by (i.e., enhanced by) at least about 2% (i.e., 1.02-fold), at least about 5% (i.e., 1.05-fold), at least about 10% (i.e., 1.10-fold), at least about 15% (i.e., 1.15-fold), at least about 20% (i.e., 1.20-fold), at least about 25% (i.e., 1.25-fold), at least about 30% (i.e., 1.30-fold), at least about 35% (i.e., 1.35-fold), at least about 40% (i.e., 1.40-fold), at least about 45% (i.e., 1.45-fold), at least about 50% (i.e., 1.50-fold), at least about 55% (i.e., 1.55-fold), at least about 60% (i.e., 1.60-fold), at least about 65% (i.e., 1.65-fold), at least about 70% (i.e., 1.70-fold), at least about 75% (i.e., 1.75-fold), at least about 80% (i.e., 1.80-fold), at least about 85% (i.e., 1.85-fold), at least about 90% (i.e., 1.90-fold), at least about 95% (i.e., 1.95-fold), or at least about 100% relative to (i.e., compared with) (i.e., 2-fold) the expression of said gene in a corresponding control cell as defined herein.

In certain embodiments, the expression of a gene encoding a protein in the MSC-derived cells of osteochondroblastic or osteoblastic lineage may be at least about 2-fold, at least about 5-fold, at least about 10-fold, at least about 20-fold, at least about 30-fold, at least about 40-fold, at least about 40-fold, at least about 50-fold, at least about 100-fold, at least about 500-fold, at least about 1000-fold, at least about 2000-fold, at least about 3000-fold, or at least about 5000-fold, the expression of a control gene in a corresponding control cell as defined herein.

In certain embodiments, the expression of a gene encoding a protein in the MSC-derived cells of osteochondroblastic or osteoblastic lineage may be decreased (i.e., reduced) by at least about 1% relative to (i.e., compared with) (i.e., the expression of a gene encoding a protein in the MSC-derived cells of osteochondroblastic or osteoblastic lineage may be at least about 0.99-fold) the expression of said gene in a corresponding control cell as defined herein. For example, the expression of a gene encoding a protein in the MSC-derived cells of osteochondroblastic or osteoblastic lineage may be decreased by (i.e., reduced by) at least about 2% (i.e., 0.98-fold), at least about 5% (i.e., 0.95-fold), at least about 10% (i.e., 0.90-fold), at least about 15% (i.e., 0.85-fold), at least about 20% (i.e., 0.80-fold), at least about 25% (i.e., 0.75-fold), at least about 30% (i.e., 0.70-fold), at least about 35% (i.e., 0.65-fold), at least about 40% (i.e., 0.60-fold), at least about 45% (i.e., 0.55-fold), at least about 50% (i.e., 0.50-fold), at least about 55% (i.e., 0.45-fold), at least about 60% (i.e., 0.40-fold), at least about 65% (i.e., 0.35-fold), at least about 70% (i.e., 0.30-fold), at least about 75% (i.e., 0.25-fold), at least about 80% (i.e., 0.20-fold), at least about 85% (i.e., 0.15-fold), at least about 90% (i.e., 0.10-fold), at least about 95% (i.e., 0.05-fold), or at least about 99% relative to (i.e., compared with) (i.e., 0.01-fold) the expression of said gene in a corresponding control cell as defined herein.

In certain embodiments, the expression of a gene encoding a protein in the MSC-derived cells of osteochondroblastic or osteoblastic lineage may be at least about 0.005-fold, at least about 0.001-fold, at least about 0.0005-fold, or at least about 0.0001-fold, the expression of a control gene in a corresponding control cell as defined herein.

In certain embodiments, the control cells as taught herein may be MSC or may be bone-forming cells generated by a method which is substantially the same in substantially all parameters than the method as taught herein for obtaining MSC-derived cells from MSC, other than the presence vs. absence of heparin or its analogue or derivative.

In certain embodiments, the MSC-derived cells of osteochondroblastic or osteoblastic lineage secrete higher amounts of proteins involved in osteochondrogenesis selected from CHI3L1 or MMP13, as compared to MSC or bone-forming cells generated by a method which is substantially the same in substantially all parameters than the method as taught herein for obtaining MSC-derived cells from MSC, other than the presence vs. absence of heparin or its analogue or derivative. In certain embodiments, the MSC-derived cells of osteochondroblastic or osteoblastic lineage secrete lower amounts of DKK1 proteins involved in the inhibition of osteogenesis as compared to MSC or bone-forming cells generated by a method which is substantially the same in substantially all parameters than the method as taught herein for obtaining MSC-derived cells from MSC, other than the presence vs. absence of heparin or its analogue or derivative.

As described earlier, the above detailed methods can yield MSC-derived cells of osteochondroblastic or osteoblastic lineage, or populations of such MSC-derived cells, with superior characteristics, such as in particular (i) high expression of ALP, which represents the cell's commitment towards the osteochondroblastic or osteoblastic lineage, and (ii) low HLA-DR expression, which represents the limited immunogenicity of the MSC-derived cells of osteochondroblastic or osteoblastic lineage, indicating that the cells are more suitable for cell transplantation, for instance to allogeneic subjects.

Accordingly, in particular embodiments, at least 70% (by number) of the MSC-derived cells of osteochondroblastic or osteoblastic lineage are positive for alkaline phosphatase (ALP); and less than 10% (by number) of the MSC-derived cells of osteochondroblastic or osteoblastic lineage are positive for HLA-DR.

In particular embodiments, substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage obtained by the methods for obtaining MSC-derived cells of osteochondroblastic or osteoblastic lineage from MSC are positive for CD73, CD63 and CD166; substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage are negative for CD45; at least 70% of the MSC-derived cells of osteochondroblastic or osteoblastic lineage are positive for alkaline phosphatase (ALP); and less than 10% of the MSC-derived cells of osteochondroblastic or osteoblastic lineage are positive for HLA-DR.

In particular embodiments, substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic lineage obtained by the methods for obtaining MSC-derived cells of osteochondroblastic or osteoblastic lineage from MSC are positive for CD90, CD105, CD73, CD63 and CD166; substantially all (e.g., at least 90% (by number), such as, e.g., ≥91%, ≥92%, ≥93%, ≥94%, ≥95%, ≥96%, ≥97%, ≥98%, ≥99%, or 100%) MSC-derived cells of osteochondroblastic or osteoblastic are negative for CD45, CD14 and CD19; at least 70% of the MSC-derived cells of osteochondroblastic or osteoblastic lineage are positive for alkaline phosphatase (ALP); and less than 10% of the MSC-derived cells of osteochondroblastic or osteoblastic lineage are positive for HLA-DR.

In certain particularly preferred embodiments, the recitation "MSC-derived cells of the chondroblastic (cartilage) lineage" may refer to cell types having a chondroblastic phenotype, and that can contribute to, or are capable of developing to cells which can contribute to, the formation of cartilage or cartilaginous matrix. As used herein, "chondroprogenitors" may particularly comprise early and late chondroprogenitors. Even more preferably, "MSC-derived cells of the chondroblastic (cartilage) lineage" may refer to osteochondroprogenitors, chondroprogenitors, pre-chondroblasts, or chondroblasts, or mixtures thereof, yet more preferably the phrase may refer to pre-chondroblasts or chondroblasts, or mixtures thereof, such as in certain examples the phrase may refer to pre-chondroblasts, or in certain other examples the phrase may refer to chondroblasts. All these terms are well-known per se.

By means of further guidance and not limitation, cells of osteochondroblastic and/or chondroblastic lineage, such as osteochondroprogenitors, chondroprogenitors, pre-chondroblasts and chondroblasts, as well as cell populations comprising osteochondroprogenitors, chondroprogenitors, pre-chondroblasts and/or chondroblasts may display the following characteristics:

a) the cells comprise expression of SOX9, a transcription factor that plays a central role during chondroblast differentiation and cartilage formation;

b) the cells comprise expression of at least one of the following: aggrecan (ACAN), type-II collagen, or CD90;

c) the cells substantially do not express CD45 (e.g., less than about 10%, preferably less than about 5%, more preferably less than about 2% of the cells may express CD45);

d) the cells show evidence of ability to produce high level of collagen types II, IX, and XI and proteoglycans, the main constituents of the hyaline extracellular matrix (ECM) in situ. Cartilage formation can be conventionally measured for example by using a safranin-orange/fast green assay to stain proteoglycans and non-collagenous protein, respectively (see, e.g., Lee et al. Tissue Engineering, 2011, vol. 18, 484-98);

e) human articular chondrocytes may display cell expression characteristics as summarised in Diaz-Romero et al. 2005 (J Cell Physiol, vol. 202(3), 731-42), e.g., they may express integrins and other adhesion molecules (CD49a, CD49b, CD49c, CD49e, CD49f, CD51/61, CD54, CD106, CD166, CD58, CD44), tetraspanins (CD9, CD63, CD81, CD82, CD151), receptors (CD105, CD119, CD130, CD140a, CD221, CD95, CD120a, CD71, CD14), ectoenzymes (CD10, CD26), and other surface molecules (CD90, CD99). During monolayer culture, chondrocytes may up-regulate certain markers regarded as distinctive for mesenchymal stem cells (CD10, CD90, CD105, CD166). Such markers may thus also be expressed by the less mature pre-chondroblasts or chondroblasts.

f) the cells substantially do not differentiate towards neither of cells of adipocytic lineage (e.g., adipocytes) or osteoblastic lineage (e.g., osteoblasts, osteocytes). The absence of differentiation towards such cell lineages may be tested using standard differentiation inducing conditions established in the art (e.g., see Pittenger et al. Science, 1999, vol. 284, 143-7), and assaying methods (e.g., when induced, adipocytes typically stain with oil red O showing lipid accumulation; pre-osteoblasts and osteoblasts typically stain for ALP). Substantially lacking propensity towards adipogenic and/or osteoblastic differentiation may typically mean that less than 20%, or less than 10%, or less than 5%, or less than 1% of the tested cells would show signs of adipogenic or osteoblastic differentiation when applied to the respective test.

As known in the art, cells of fibroblastic lineage can contribute to, or are capable of developing to cells which can contribute to, the formation of connective tissue.

By means of further guidance and not limitation, fibroblastic cells may display the following characteristics:

a) the cells comprise expression of FSP1 (fibroblast specific protein 1);

b) the cells comprise expression of at least one of the following: collagen, vimentin, desmin or CD90;

c) the cells substantially do not express CD45 (e.g., less than about 10%, preferably less than about 5%, more preferably less than about 2% of the cells may express CD45);

d) the cells show evidence of ability to produce collagen, glycosaminoglycan, reticular and elastic fibers, glycoproteins to form the extracellular matrix of the connective tissues. Fibroblasts, contribute to the structural integrity of ligaments and tendons and have a tissue repair function.

Collagen deposition can be visualized using trichrome staining (Li et al. World J Gastroenterol, 2014 vol. 20(16), 4648-61). Collagen type I (Chondres, Redmond, Wash.) and tenascin-C(Tn-C; IBL-America, Mineapolis, Minn.) are two markers for ligament fibroblasts, and can be assayed by ELISA (Brissett et al. Arthritis Rheum, 2012, vol. 64(1), 272-80).

As known in the art, cells of tendinocytic lineage can contribute the formation of tendon material or tendon matrix. Tendon is constituted by large fiber bundles that comprise a network of collagen fibrils and different types of cells, including synovial cells, endothelial cells, tenoblasts, and tenocytes lying longitudinally as row in collagen molecules. Tenoblasts are immature form of tendon cells that differentiate toward tenocytes as they age with decreased metabolic activity.

By means of further guidance and not limitation, tenocytes may display the following characteristics:

a) the cells comprise expression of scleraxis (SCX), a member of basic helix-loop-helix family of transcription factor involved in cellular differentiation and extracellular matrix organization in tendons;

b) the cells comprise expression of at least one of the following: tenomodulin (TNMD) and Tenascin-C(TNC);

c) the cells substantially express CD44, CD73, CD90 and CD 105 but do not express CD34, CD45, CD146, or stro-1;

d) the cells show evidence of ability to produce extracellular component of tendon that consist of type I, III and V collagens, proteoglycans, fibronectin, and elastic fibrils for tendon tissue regeneration (Gungormus et al. Connect Tissue Res, 2008, vol. 53(6), 485-91);

e) the cells substantially do not differentiate towards neither of cells of adipocytic lineage (e.g., adipocytes), chondroblastic lineage (e.g., chondroblasts, chondrocytes) or osteoblastic lineage (e.g., osteoblasts, osteocytes).

As known in the art, cells of synoviocyte (synovial fluid) lineage typically encompass type A or macrophage-like synovial cells and type B or fibroblasts like synoviocytes (FLC), and that can contribute to the formation of synovial membrane and synovial liquid. All these terms are well-known perse. The term "synoviocyte" as used herein thus refers to any one, as well as collectively all, such cell types.

By means of further guidance and not limitation, synoviocytes may display the following characteristics:

a) the cells show evidence of ability to secrete proteoglycan 4 (PRG4) and are the major source of surface-active phospholipids (SAPL) as well as hyaluronan (HA) present in the synovial fluid (Tamer et al. Interdiscip Toxicol, 2013, vol. 6(1), 111-125);

b) the type A or macrophage-like synovial cells comprise expression of hematopoietic origin markers including CD11b, CD86, CD14, CD163, DR antigen and Fc receptor. The type B or fibroblasts like synoviocytes are mesenchymal cells that display many characteristics of fibroblasts, including expression of type IV and V collagens, vimentin, and CD90. In addition, the type B cells have some unique properties in situ that distinguishes from many other fibroblast lineages, including sublining resident fibroblasts. For instance, cadherin-11 (specific adhesion molecule that play a key role in homotypic aggregation of FLS), CD55 (decay accelerating factor), VCAM-1 (vascular adhesion molecule 1) and ICAM-1 (intercellular adhesion molecule 1) (Bartok et al. Immunol Rev, 2011, vol. 233(1), 233-255);

c) the cells substantially do not express CD45 (e.g., less than about 10%, preferably less than about 5%, more preferably less than about 2% of the cells may express CD45);

d) the cells substantially do not differentiate towards neither of cells of adipocytic lineage (e.g., adipocytes), chondroblastic lineage (e.g., chondroblasts, chondrocytes) or osteoblastic lineage (e.g., osteoblasts, osteocytes).

Wherein a cell is said to be positive for (or to express or comprise expression of) a particular marker, this means that a skilled person will conclude the presence or evidence of a distinct signal, e.g., antibody-detectable or detection by reverse transcription polymerase chain reaction, for that marker when carrying out the appropriate measurement, compared to suitable controls. Where the method allows for quantitative assessment of the marker, positive cells may on average generate a signal that is significantly different from the control, e.g., but without limitation, at least 1.5-fold higher than such signal generated by control cells, e.g., at least 2-fold, at least 4-fold, at least 10-fold, at least 20-fold, at least 30-fold, at least 40-fold, at least 50-fold higher or even higher.

The expression of the above cell-specific markers can be detected using any suitable immunological technique known in the art, such as immunohitochemistry or affinity adsorption, Western blot analysis, flow cytometry, ELISA, etc., or by any suitable biochemical assay of enzyme activity (e.g., for ALP), or by any suitable technique of measuring the quantity of the marker mRNA, e.g., Northern blot, semi-quantitative or quantitative RT-PCR, etc. Sequence data for markers listed in this disclosure are known and can be obtained from public databases such as GenBank (http://www.ncbi.nlm.nih.gov/).

In certain embodiments of the methods, as taught herein, the MSC or MSC-derived cells may be animal cells, preferably warm-blooded animal cells, more preferably mammalian cells, such as human cells or non-human mammalian cells, and most preferably human cells.

MSC or MSC-derived cells as intended herein are preferably adherent, i.e., require a surface for growth, and typically grow as an adherent monolayer on said surface (i.e., adherent cell culture), rather than as free-floating cells in a culture medium (suspension culture). Adhesion of cells to a surface, such as the surface of a tissue culture plastic vessel, can be readily examined by visual inspection under inverted microscope. Cells grown in adherent culture require periodic passaging, wherein the cells may be removed from the surface enzymatically (e.g., using trypsin), suspended in growth medium, and re-plated into new culture vessel(s). In general, a surface or substrate which allows adherence of cells thereto may be any substantially hydrophilic substrate. As known in the art, tissue culture vessels, e.g., culture flasks, well plates, dishes, or the like, may be usually made of a large variety of polymeric materials, suitably surface treated or coated after moulding in order to provide for hydrophilic substrate surfaces. The term "contacting" as used herein means bringing together, either directly or indirectly, one or more molecules, components or materials with another, thereby facilitating interactions there between. Typically, one or more agents capable of inducing expansion and/or differentiation of MSC or MSC-derived cells may be contacted with MSC or MSC-derived cells by means of their inclusion in the media, in which the MSC or MSC-derived cells are cultured.

The term "in vitro" as used herein is to denote outside, or external to, animal or human body. The term "in vitro" as used herein should be understood to include "ex vivo". The term "ex vivo" typically refers to tissues or cells removed from an animal or human body and maintained or propagated outside the body, e.g., in a culture vessel. The term "fibroblast growth factor 2 (FGF-2)", "basic FGF", "FGF-b", "FGFB", "BFGF", "heparin-binding growth factor 2 (HBGF-2)", or "prostatropin", can be used interchangeably and refers to so-known member of the fibroblast growth factor family. The inventors have realised that FGF-2 is particularly effective in the method of the present invention.

The term "transforming growth factor beta (TGFβ)", "TGFB" or "TGFbeta" as used herein refers to a member of the transforming growth factor beta (TGFβ) family. The inventors have realized that TGFβ is particularly effective in the method of the present invention. In a further embodiment, the said member of the TGFβ family is chosen from the group consisting of TGF-beta-1, TGF-beta-2, TGF-beta-3, TGF-beta-4, GDF1 (Growth differentiation factor 1), GDF-2, GDF-3, GDF-5, GDF-6, GDF-7, GDF-8, GDF-9, GDF-11, GDF-15, INHA (inhibin alpha chain), INHBA (inhibin beta A chain), INHBB (inhibin beta B chain), INHBC (inhibin beta C chain), INHBE (inhibin beta E chain), MIS (Muellerian-inhibiting factor), and further of members of GDNF subfamily, including GDNF (glial cell line-derived neurotrophic factor), NRTN (neurturin), PSPN (persephin), and mixtures thereof.

In a particular embodiment, TGFβ is selected from the group consisting of TGFβ1, TGFβ2, TGFβ, and mixtures thereof. In a particular embodiment, TGFβ is TGFβ1. By means of example, TGFβ1 may be used in the present methods as the sole TGFB cytokine.

In a further embodiment, MSC or MSC-derived cells may be—in addition to FGF-2 and TGFβ-contacted with one or more additional, exogenously added growth factors other than FGF-2 and TGFβ. In another embodiment, FGF-2 and TGFβ may be the sole exogenous growth factors with which the MSC or MSC-derived cells are contacted.

In a preferred embodiment, the growth factor used in the present method is a human growth factor. As used herein, the term "human growth factor" refers to a growth factor substantially the same as a naturally occurring human growth factor. For example, where the growth factor is a proteinaceous entity, the constituent peptide(s) or polypeptide(s) thereof may have primary amino acid sequence identical to a naturally occurring human growth factor. The use of human growth factors in the present method is preferred, as such growth factors are expected to elicit a desirable effect on cellular function.

The term "naturally occurring" is used to describe an object or entity that can be found in nature as distinct from being artificially produced by man. For example, a polypeptide sequence present in an organism, which can be isolated from a source in nature and which has not been intentionally modified by man in the laboratory, is naturally occurring. When referring to a particular entity, e.g., to a polypeptide or protein, the term encompasses all forms and variants thereof which occur in nature, e.g., due to a normal variation between individuals. For example, when referring to a proteinaceous growth factor, the term "naturally occurring" encompasses growth factors having differences in the primary sequence of their constituent peptide(s) or polypeptide(s) due to normal allelic variation between individuals.

The present method may employ a biologically active variant or fragment of a growth factor. In the method of the invention, "biologically active" variants or fragment of a growth factor achieve at least about the same degree of obtaining MSC-derived cells from MSCs as the respective growth factor, when other conditions are substantially the same.

A "variant" of a polypeptide has an amino acid sequence which is substantially identical (i.e., largely but not wholly identical) to the amino acid sequence of the polypeptide. Herein, "substantially identical" refers to at least 85% identical, e.g., at least 90% identical, preferably at least 95% identical, e.g., least 99% identical. Sequence differences may result from insertion (addition), deletion and/or substitution of one of more amino acids.

In another embodiment, the growth factors used in the present method, namely at least FGF-2 and TGFβ, may be non-human animal growth factors, and particularly non-human mammal growth factors, or biologically active variants or derivatives thereof. As used herein, the terms "non-human animal growth factor" and "non-human mammal growth factor" refer to a growth factor substantially the same as, respectively, a naturally occurring non-human animal or non-human mammal growth factor. For example, where the growth factor is a proteinaceous entity, the constituent peptide(s) or polypeptide(s) thereof may have primary amino acid sequence identical to a naturally occurring non-human animal or non-human mammal growth factor. A skilled person will understand that non-human animal or non-human mammal growth factors may be applicable in the present method, albeit to a lesser extent than human animal growth factors, since the latter are of the same origin as the MSC cells. In particular, non-human animal or non-human mammal growth factors may be used if they elicit the desired effect, e.g., an effect similar to an (analogous) human growth factor.

In a preferred embodiment, the growth factors or a biologically active variants or derivatives thereof are recombinant, i.e., produced by a host organism through the expression of a recombinant nucleic acid molecule, which has been introduced into the host organism or an ancestor thereof, and which comprises a sequence encoding said polypeptide. The term "recombinant nucleic acid molecule" as used herein refers to a nucleic acid molecule (e.g., a DNA or cDNA molecule) which is comprised of segments joined together using recombinant DNA technology.

In particular embodiments, the MSC or MSC-derived cells are additionally contacted with, such as wherein the medium additionally comprises one or more of plasma, serum or a substitute thereof.

The term "plasma" is as conventionally defined and comprises fresh plasma, thawed frozen plasma, solvent/detergent-treated plasma, processed plasma (e.g., PRP), or a mixture of any two or more thereof. Plasma is usually obtained from a sample of whole blood, provided or contacted with an anticoagulant, (e.g., heparin (at very low concentrations, typically about $15 \times 10^{-5}$ IU/ml, citrate, oxalate or EDTA). Subsequently, cellular components of the blood sample are separated from the liquid component (plasma) by an appropriate technique, typically by centrifugation. By means of a specific example but not limitation, to obtain plasma suitable for use in the present invention, a blood sample may be drawn into a vacutainer tube containing the anticoagulant EDTA (ethylenediaminetetraacetic acid) (e.g., BD Vacutainer plastic EDTA tube, 10 ml, 1.8 mg/mL). The sample is gently shaken and then centrifuged during 10 min at room temperature at 1,000-2,000 g to separate the plasma from red blood cells. The supernatant (plasma) is collected, optionally pooled (if a plurality of blood samples is used), and aliquoted into cryovials, which are stored at −80° C. until use. The term "plasma" refers to a composition which does not form part of a human or animal body. The term "plasma" may in certain embodiments specifically include processed plasma, i.e., plasma subjected after its separation from whole blood to one or more processing steps which alter its composition, specifically its chemical, biochemical, or cellular composition. Accordingly, the term "plasma" as intended herein may include platelet-rich plasma (PRP), i.e., plasma that has been enriched with platelets. Typically, PRP may contain about $1.0 \times 10^6$ platelets/μl, whereas platelet concentration in whole blood may be about $1.5 \times 10^5$ to $3.5 \times 10^5$/μL.

Plasma may be solvent/detergent-treated. The terms "solvent/detergent-treated plasma", "S/D-treated plasma", or "S/D plasma" generally refer to decellularized plasma obtainable or obtained by a method comprising the steps of: (a) treating plasma with a solvent and a detergent and (b) filtering the solvent/detergent-treated plasma. Solvents suitable for such treatment are solvents such as di- or trialkylphosphates and detergents which are described in U.S. Pat. No. 4,764,369. The detergent used for preparing S/D plasma preferably is a non-toxic detergent (e.g., Tween® 20 or Tween® 80).

The term "serum" is as conventionally defined and comprises fresh serum, thawed frozen serum or serum prepared from plasma, or a mixture of any two or more thereof. Serum can be usually obtained from a sample of whole blood by first allowing clotting to take place in the sample and subsequently separating the so formed clot and cellular components of the blood sample from the liquid component (serum) by an appropriate technique, typically by centrifugation. Clotting can be facilitated by an inert catalyst, e.g., glass beads or powder. Alternatively, serum can be obtained from plasma by removing the anticoagulant and fibrin. By means of a specific example but not limitation, to obtain serum suitable for use in the present invention, a blood sample may be drawn into a vacutainer tube containing no anticoagulant (e.g., BD Vacutainer Plus plastic serum tube, 10 ml) and incubated for 30 to 45 min at room temperature to allow clotting. The tube is then centrifuged for 15 min at room temperature at 1,000-2,000 g to separate the serum from red blood cells. The supernatant (serum) is collected, optionally pooled (if a plurality of blood samples is used) and aliquoted into cryovials which are stored at −80° C. until use. The term "serum" hence refers to an acellular composition which does not form part of a human or animal body. The serum as intended herein is human serum, i.e., obtained from a single human subject or from a plurality of human subjects (e.g., serum mixed pool). The serum may be unprocessed serum, i.e., serum derived by separation from whole blood and not subjected to downstream processing steps which alter its chemical, biochemical, or cellular composition, other than optional heat inactivation, storage (cryogenic or non-cryogenic), sterilisation, freeze-drying and/or filtration. In certain embodiments, the serum may be obtained from solvent/detergent-treated plasma.

The isolated plasma, serum or substitute thereof can be used directly in the method of the present invention. They can also be appropriately stored for later use (e.g., for shorter time periods, e.g., up to about 1-2 weeks, at a temperature above the respective freezing points of plasma, serum or substitute thereof, but below ambient temperature, this temperature will usually be about 4° C. to 5° C.; or for longer times by freeze storage, usually at between about −70° C. and about −80° C.).

The isolated plasma, serum or substitute thereof can be heat inactivated as known in the art, particularly to remove the complement. Where the present method employs plasma, serum, or substitute thereof autologous to the cells cultured in the presence thereof, it may be unnecessary to heat inactivate the plasma, serum or substitute thereof. Where the plasma, serum or substitute thereof is at least partly allogeneic to the cultured cells, it may be advantageous to heat inactivate the plasma, serum or substitute thereof. Optionally, the plasma, serum or substitute thereof may also be sterilized prior to storage or use, using conventional microbiological filters, preferably with pore size of 0.2 μm or smaller.

In an embodiment, the present method may employ human plasma, serum or substitute thereof which is autologous to human MSC or MSC-derived cells contacted therewith. The term "autologous" with reference to plasma, serum or substitute thereof denotes that the plasma, serum or substitute thereof is obtained from the same subject as are MSC or MSC-derived cells to be contacted with the said plasma, serum or substitute thereof. The use of autologous plasma, serum or substitute thereof may ensure optimal acceptance of the cells by the subject and/or avoid accidental transmission of infectious agents from, e.g., other sera.

In another embodiment, the method may employ human plasma, serum or substitute thereof which is "homologous" or "allogeneic" to human MSC or MSC-derived cells contacted therewith, i.e., obtained from one or more (pooled) human subjects other than the subject from which the MSC are obtained.

In a further embodiment, the method may employ a mixture of autologous and allogeneic (i.e., homologous) plasma, sera or substitute thereof as defined above. The phrase "substitute of serum or plasma" as used herein, refers to a natural or artificial non-toxic composition having one or more of the functions of plasma and/or serum, such as compositions capable of inducing growth and/or expansion of MSC or MSC-derived cells. Non-limiting examples of substitutes of serum or plasma include platelet lysate and compositions for cell culture comprising one or more fractionated components of plasma or serum, such as human serum albumin. A skilled person appreciates that human plasma, serum and substitutes thereof are complex biological compositions, which may comprise one or more growth factors, cytokines or hormones.

It is intended that growth factors FGF-2 and TGFβ or their respective biologically active variants or derivatives are provided in addition to, i.e., exogenously to or in supplement to, one or more of plasma, serum or a substitute thereof.

The term "heparin" as used herein refers to a polymer of the glycosaminoglycan family of carbohydrates with a molecular weight ranging from 3 to 30 kDa characterized by its anticoagulating effects. The potency of heparin or a derivative or analogue thereof may be determined in vitro by a biological assay wherein the concentration of heparin necessary to prevent the clotting of sheep or goat or human plasma is compared to the concentration of an internationally accepted reference standard an international accepted reference standard based on units of heparin activity per milligram. One mg of heparin is typically equal to 140-180 international units (IU).

The term "IU" or "international units" is a standard measure of the quantity of a biological substance expressed as the biological activity or effect of said biological substance. For every substance to which this unit is assigned, there is an internationally accepted biological activity or effect expected with a dose of 1 IU when tested according to an internationally accepted biological procedure.

In particular embodiments, the heparin or heparin derivative or analogue is selected from the group consisting of unfractionated heparin (UFH); low molecular weight heparin (LMWH), such as enoxaparin, dalteparin, nadroparin, tinzaparin, certoparin, reviparin, ardeparin, parnaparin, bemiparin, or mixtures thereof; a heparinoid, such as heparan sulfate, dermatan sulfate, chondroitin sulfate, acharan sulfate, keratan sulfate, or mixtures thereof, such as danaparoid; a heparin salt; a heparinoid salt; a heparin fragment; a heparinoid fragment; and mixtures thereof. Preferably, the heparin or heparin derivative or analogue is selected from the group consisting of UFH, dalteparin, danaparoide and heparan sulfate.

In particular embodiments, said FGF-2, said TGFβ, said heparin or a derivative or analogue thereof, and optionally one or more of plasma, serum or substitute thereof, are included in a medium, commonly a liquid cell culture medium. Typically, the medium will comprise a basal medium formulation as known in the art. Many basal media formulations (available, e.g., from the American Type Culture Collection, ATCC; or from Invitrogen, Carlsbad, Calif.) can be used to culture the cells herein, including but not limited to Eagle's Minimum Essential Medium (MEM), Dulbecco's Modified Eagle's Medium (DMEM), alpha modified Minimum Essential Medium (alpha-MEM), Basal Medium Essential (BME), BGJb, F-12 Nutrient Mixture (Ham), Iscove's Modified Dulbecco's Medium (IMDM), or X-VIVO™ serum free medium (clinical grade), available from Invitrogen or Cambrex (New Jersey), and modifications and/or combinations thereof. Compositions of the above basal media are generally known in the art and it is within the skill of one in the art to modify or modulate concentrations of media and/or media supplements as necessary for the cells cultured. Such basal media formulations contain ingredients necessary for mammal cell development, which are known per se. By means of illustration and not limitation, these ingredients may include inorganic salts (in particular salts containing Na, K, Mg, Ca, Cl, P and possibly Cu, Fe, Se and Zn), physiological buffers (e.g., HEPES, bicarbonate), nucleotides, nucleosides and/or nucleic acid bases, ribose, deoxyribose, amino acids, vitamins, antioxidants (e.g., glutathione) and sources of carbon (e.g., glucose, sodium pyruvate, sodium acetate), etc.

For use in culture, basal media can be supplied with one or more further components. For example, additional supplements can be used to supply the cells with the necessary trace elements and substances for optimal growth and expansion. Such supplements include insulin, transferrin, selenium salts, and combinations thereof. These components can be included in a salt solution such as, but not limited to, Hanks' Balanced Salt Solution (HBSS), Earle's Salt Solution. Further antioxidant supplements may be added, e.g., β-mercaptoethanol. While many basal media already contain amino acids, some amino acids may be supplemented later, e.g., L-glutamine, which is known to be less stable when in solution. A medium may be further supplied with antibiotic and/or antimycotic compounds, such as, typically, mixtures of penicillin and streptomycin, and/or other compounds, exemplified but not limited to, amphotericin, ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin. Lipids and lipid carriers can also be used to supplement cell culture media.

Such lipids and carriers can include, but are not limited to cyclodextrin, cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulations.

In particular embodiments, one or more of human plasma, serum or a substitute thereof may be comprised in said media at a proportion (volume of one or more of plasma, serum, or a substitute thereof/volume of medium) between about 0.5% and about 30%, preferably between about 1% and about 15%, more preferably between 2% and 10%. The present methods may perform satisfactorily with relatively low amounts of one or more of plasma, serum or a substitute thereof, e.g., about 5 or 10 volume % or below, e.g., about 1, about 2, about 3 or about 4 volume %, allowing to decrease the volume of one or more of plasma, serum or a substitute thereof that needs to be obtained in order to culture the MSC or MSC-derived cells.

In yet further embodiments, one or more of concentrated plasma products (e.g., plasma concentrates such as concentrates from frozen plasma), concentrated serum products or products of a concentrated substitute of plasma or serum may be employed. Such concentrated products may be included in the composition at a concentration lower than the desired concentration of one or more of plasma, serum or a substitute thereof, such as to offset (counterbalance, compensate for) the concentration factor.

In particular embodiments, combinations or mixtures of any two or more of human plasma, serum and/or a substitute thereof may be used.

In particular embodiments, FGF-2 and TGFβ are comprised in said medium at concentrations sufficient to induce differentiation towards a desired cell-type.

In particular embodiments, FGF-2 and TGFβ are comprised in said medium at concentrations sufficient to induce differentiation of MSC into MSC-derived cells of an osteochondroblastic or osteoblastic lineage. Typically, FGF-2 or a biologically active variant or fragment thereof can be included in the media at a concentration of between 0.1 and 100 ng/ml, preferably between 0.5 and 20 ng/ml, e.g., at about 19, 18, 17, 16, 15, 14, 13, 12, 11, 10, 9, 8, 7 or 6 ng/ml, or at about 5 ng/ml or less, e.g., at about 4, 3, 2, 1 or 0.5 ng/ml. Typically, TGFβ, such as TGFβ1, or a biologically active variant or fragments thereof can be included in the media at a concentration of between 0.1 and 100 ng/ml, preferably between 0.25 and 20 ng/ml, e.g., at about 19, 18, 17, 16, 15, 14, 13, 12, 11, 10, 9, 8, 7 or 6 ng/ml, or at about 5 ng/ml or less, e.g., at about 4, 3, 2, 1 or 0.5 ng/ml. Said values are intended to refer to concentrations of the respective growth factors or a biologically active variants or fragments thereof, as exogenously supplemented to the media.

In particular embodiments, heparin or a derivative or analogue thereof is comprised in said medium at a concentration of at least 0.01 IU/ml, at least 0.02 IU/ml, at least 0.03 IU/ml, at least 0.04 IU/ml, at least 0.05 IU/ml, at least 0.06 IU/ml, at least 0.07 IU/ml, at least 0.08 IU/ml, at least 0.09 IU/ml, at least 0.1 IU/ml, at least 0.5 IU/ml, at least 1 IU/ml, at least 5 IU/ml, at least 10 IU/ml, at least 20 IU/ml, at least 30 IU/ml, at least 40 IU/ml, at least 50 IU/ml, at least 60 IU/ml, at least 70 IU/ml, at least 80 IU/ml, at least 90 IU/ml, or at least 100 IU/ml. In particular embodiments, heparin or a derivative or analogue thereof is comprised in said medium at a concentration of at least 0.10 IU/ml. In certain preferred embodiments, heparin or a derivative or analogue thereof is comprised in said medium at a concentration of about 0.1 IU/ml. In certain embodiments, heparin or a derivative or analogue thereof may be comprised in said medium at a concentration of about 0.10 IU/ml, 0.20 IU/ml, 0.30 IU/ml, 0.40 IU/ml, 0.50 IU/ml, 0.60 IU/ml, 0.70 IU/ml, 0.80 IU/ml, 0.90 IU/ml or 1.0 IU/ml.

In particular embodiments, the concentration of heparin or derivative or analogue thereof is at least 0.05 IU/ml, preferably about 0.1 IU/ml.

In an embodiment, the above concentrations may refer to the total concentration of growth factors or biologically active variants or fragments thereof or of said heparin or derivative or analogue thereof in the medium, i.e., to the sum concentration of said growth factors or biologically active variants or fragments thereof or of said heparin or derivative or analogue thereof as contributed by the plasma, serum or substitute thereof and as provided in addition thereto.

In another embodiment, the above concentrations may refer to the concentration of said growth factors or biologically active variants or fragments thereof or of said heparin or derivative or analogue thereof as provided in addition to that already contributed by the plasma or serum. Understandably, if the growth factors or heparin or derivative or analogue thereof to-be-added is normally not present (not detectable) in the plasma, serum or substitute thereof, the total and added concentration of the growth factors or heparin or derivative or analogue thereof will be (substantially) the same.

In particular embodiments, the method for obtaining MSC-derived cells from MSC as described herein comprises the steps of (a) culturing MSC recovered from a biological sample of a subject in a medium comprising FGF-2, TGFβ and heparin or derivative or analogue thereof at a concentration of at least 0.01 IU/ml;

(b) removing non-adherent matter and further culturing adherent cells in the medium comprising FGF-2, TGFβ and heparin or a derivative or analogue thereof at a concentration of at least 0.01 IU/ml, thereby obtaining the MSC-derived cells. In a preferred embodiment, MSC recovered from a biological sample of a subject as defined elsewhere herein are cultured in a culture vessel. The culture vessel may provide for a plastic surface to enable cell adherence. In another embodiment, the surface may be a glass surface. In yet another embodiment, the surface may be coated with an appropriate material enable adherence and growth of cells, e.g., Matrigel, laminin or collagen.

In particular embodiments, the MSC may be recovered from bone marrow (or other sources) by selecting those (mononuclear) cells which can adhere to a substrate surface, e.g., plastic surface.

In particular embodiments, cells may be allowed to attach for about 1 and 8 days, more typically between about 2 and 6 days, more typically about 4 days before removing the non-adherent matter in step (b). Otherwise, step (b) is performed at most 8 days, at most 6 days, at most 4 days, preferably at most 4 days, after initiating step (a).

In particular embodiments the cells can be cultured in steps (a) and (b) taken together for a period of between about 7 and about 35 days, usually between about 10 and about 28 days, and more preferably for about 12-21 days. Otherwise, the cells may be cultured in steps (a) and (b) taken together until their confluence reaches about 60% or more, or about 80% or more, or about 90% or more, or even up to 100%.

In an embodiment, following step (b) the method may comprise collecting the so-obtained cells or cell population.

In an embodiment, following step (b) the method may comprise detaching, replating and culturing the MSC-derived cells in the medium comprising FGF-2, TGFβ and heparin or a derivative or analogue thereof, preferably at a concentration of at least 0.01 IU/ml.

In an embodiment, following step (b) the method may comprise detaching, replating and culturing the MSC-derived cells in an osteogenic or chondrogenic differentiation medium.

Osteogenic and chondrogenic differentiation media are known in the art. Without limitation, osteogenic differentiation media may include basal media supplied with ascorbic acid, 3-glycerophosphate, and dexamethasone. Without limitation, chondrogenic differentiation media may include basal media supplied with insulin, transferrin, sodium selenite, ascorbic acid, TGFβ-1, sodium pyruvate and dexamethasone.

The detaching, replating and culturing the MSC-derived cells after step (b) may be performed one or more times, such as one time, two times, three times, four times, five times, six times, seven times, eight times, nine times or ten times. The skilled person will understand that this may generate cell cultures of passage 1 (P1), passage 2 (P2), passage 3 (P3), passage 4 (P4), passage 5 (P5), passage 6 (P6), passage 7 (P7), passage 8 (P8), passage 9 (P9) or passage 10 (P10), respectively. Passage 0 (P0) may refer to MSC or MSC-derived cells which have not been detached and/or replated.

Differentiation of MSC, such as in particular osteogenic differentiation of MSC, typically results in MSC-derived cells which have a larger cell size than the MSC from which they are derived. The inventors found that this increase in cell size does not occur or is reduced or minimised when MSC-derived cells are obtained from MSC by contacting MSC or MSC-derived cells in vitro or ex vivo with heparin or a derivative or analogue thereof at a concentration of at least 0.01 IU/ml. Such smaller MSC-derived cells have advantageously improved transplantation properties, as described elsewhere herein.

Accordingly, a further aspect provides a method for obtaining MSC-derived cells with improved transplantation properties from MSC, the method comprising a size reduction step, wherein said size reduction step is characterized by contacting MSC or MSC-derived cells in vitro or ex vivo with heparin or a derivative or analogue thereof at a concentration of at least 0.01 IU/ml. The term "size reduction" as used herein refers to (i) reduced physical dimensions or size of MSC-derived cells (e.g., as measured by average size, diameter or volume, or a suitable cell size indication variable, such as $D_{60}$, $D_{65}$, $D_{70}$, or $D_{75}$) obtained by a method comprising the size reduction step compared to MSC-derived cells obtained by an otherwise identical method not comprising the size reduction step. The size reduction may be a decrease in average cell size of at least 30%, at least 25%, at least 20%, preferably at least 30%, of MSC-derived cells obtained with the size reduction step compared to the average cell size of MSC-derived cells obtained without the size reduction step.

In particular embodiments, the method for obtaining MSC-derived cells from MSC with improved transplantation properties as described herein comprises a step of cultivating MSC in vitro or ex vivo in an appropriate supplemented culture medium to reach a high proliferation rate with late and early stage differentiation features, wherein said step is performed simultaneously with or before the size reduction step.

In particular embodiments, the method may comprise contacting MSC with one or more agents capable of inducing expansion and/or differentiation of MSC simultaneously with or prior to contacting the cells with heparin or a derivative or analogue thereof at a concentration of at least 0.01 IU/ml.

The term "agent" broadly refers to any chemical (e.g., inorganic or organic), biochemical or biological substance, molecule or macromolecule (e.g., biological macromolecule), a combination or mixture thereof, a sample of undetermined composition, or an extract made from biological materials such as bacteria, plants, fungi, or animal cells or tissues. Non-limiting examples of agents capable of inducing expansion and/or differentiation of MSC are growth factors, such as FGF-2 and TGFβ, and plasma or serum or a substitute thereof. The skilled person will understand that the growth factor or combination of growth factors may be any growth factor or combination of growth factors known of being capable of inducing differentiation of MSC towards a desired cell type.

In particular embodiments, the method for obtaining MSC-derived cells from MSC with improved transplantation properties as described herein further comprises a step of contacting MSC or MSC-derived cells in vitro or ex vivo with FGF-2 and TGFβ. Contacting of said MSC or MSC-derived cells in vitro or ex vivo with FGF-2, TGFβ and heparin or a derivative or analogue thereof at a concentration of at least 0.01 IU/ml is preferably performed simultaneously.

In particular embodiments, the MSC or MSC-derived cells are additionally contacted with, such as wherein the medium additionally comprises, one or more of plasma, serum or a substitute thereof.

As described earlier, the above detailed methods yield MSC-derived cells, or populations comprising such, with superior characteristics, such as in particular a smaller and more homogeneous size than MSC-derived cells described earlier. The smaller and more homogeneous size of the MSC-derived cells obtainable by the methods as described herein makes the cells having improved transplantation properties. More particularly, the smaller and more homogeneous size of the MSC-derived cells obtainable by the methods as described herein makes the cells suited for all routes of administration and in particular intravascular administration, inter alia, by reducing or eliminating the risk at pulmonary embolism and infarction, by offering a good in vivo safety profile and/or syringability. Furthermore, the MSC-derived cells obtainable by the methods as described herein allow a tunable and high cell concentration to be delivered at site with a limited volume administered.

In view hereof, the method of the invention can be further defined by the size, characterized by the diameter and/or the volume of a cell, of the MSC-derived cells resulting from contacting MSC with FGF-2, TGFβ and heparin or a derivative or analogue thereof.

In particular embodiments, the average diameter of the MSC-derived cells in suspension is less than 30 μm, less than 29 μm, less than 28 μm, less than 27 μm, less than 26 μm, less than 25 μm, or less than 24 μm. Preferably, the average diameter of the MSC-derived cells in suspension is less than 24 μm.

The terms "suspension" and "cell suspension" generally refers to MSC-derived cells, particularly viable MSC-derived cells, dispersed in a liquid phase.

In particular embodiments, the average diameter of the MSC-derived cells in suspension is more than 10 μm, more than 11 μm, more than 12 μm, more than 13 μm, more than 14 μm, more than 15 μm, more than 16 μm, more than 17 μm or more than 18 μm.

In particular embodiments, the average diameter of the MSC-derived cells in suspension is between 16 μm and 26 μm, preferably between 20 μm and 25 μm.

In particular embodiments, at least 60% of the MSC-derived cells in suspension have a diameter equal to or less than 25 μm ($D_{60} \leq 25$ μm), equal to or less than 24 μm ($D_{60} \leq 24$ μm), equal to or less than 23 μm ($D_{60} \leq 23$ μm), equal to or less than 22 μm ($D_{60} \leq 22$ μm), equal to or less than 21 μm ($D_{60} \leq 21$ μm), or equal to or less than 20 μm ($D_{60} \leq 20$ μm), preferably equal to or less than 25 μm ($D_{60} \leq 25$ μm).

In particular embodiments, at least 65% of the MSC-derived cells in suspension have a diameter equal to or less than 25 μm ($D_{65} \leq 25$ μm), equal to or less than 24 μm ($D_{65} \leq 24$ μm), equal to or less than 23 μm ($D_{65} \leq 23$ μm), equal to or less than 22 μm ($D_{65} \leq 22$ μm), equal to or less than 21 μm ($D_{65} \leq 21$ μm), or equal to or less than 20 μm ($D_{65} \leq 20$ μm), preferably equal to or less than 25 μm ($D_{65} \leq 25$ μm).

In particular embodiments, at least 70% of the MSC-derived cells in suspension have a diameter equal to or less than 25 μm ($D_{70} \leq 25$ μm), equal to or less than 24 μm ($D_{70} \leq 24$ μm), equal to or less than 23 μm ($D_{70} \leq 23$ μm), equal to or less than 22 μm ($D_{70} \leq 22$ μm), equal to or less than 21 μm ($D_{70} \leq 21$ μm), or equal to or less than 20 μm ($D_{70} \leq 20$ μm), preferably equal to or less than 25 μm ($D_{70} \leq 25$ μm).

In particular embodiments, at least 75% of the MSC-derived cells in suspension ($D_{75} \leq 25$ μm) have a diameter equal to or less than 25 μm, equal to or less than 24 μm ($D_{75} \leq 24$ μm), equal to or less than 23 μm ($D_{75} \leq 23$ μm), equal to or less than 22 μm ($D_{75} \leq 22$ μm), equal to or less than 21 μm ($D_{75} \leq 21$ μm), or equal to or less than 20 μm ($D_{75} \leq 20$ μm), preferably equal to or less than 25 μm ($D_{75} \leq 25$ μm).

In particular embodiments, the MSC-derived cells in suspension exhibit a $D_{60}$ equal to or less than 25 μm ($D_{60} \leq 25$ μm) and at most 5% of the MSC-derived cells in suspension have a diameter of more than 35 μm. In particular embodiments, the MSC-derived cells in suspension exhibit a $D_{65}$ equal to or less than 25 μm ($D_{65} \leq 25$ μm) and at most 5% of the MSC-derived cells in suspension have a diameter of more than 35 μm.

In particular embodiments, the MSC-derived cells in suspension exhibit a $D_{70}$ equal to or less than 25 μm ($D_{70} \leq 25$ μm) and at most 5% of the MSC-derived cells in suspension have a diameter of more than 35 μm.

In particular embodiments, the MSC-derived cells in suspension exhibit a $D_{75}$ equal to or less than 25 μm ($D_{75} \leq 25$ μm) and at most 5% of the MSC-derived cells in suspension have a diameter of more than 35 μm.

In particular embodiments, the MSC-derived cells in suspension exhibit a $D_{60}$ between about 25 μm and about 10 μm (10 μm$\leq D_{60} \leq$25 μm), between about 24 μm and about 10 μm (10 μm$\leq D_{60} \leq$24 μm), between about 23 μm and about 10 μm (10 μm$\leq D_{60} \leq$23 μm), between about 22 μm and about 10 μm (10 μm$\leq D_{60} \leq$22 μm), between about 21 μm and about 10 μm (10 μm$\leq D_{60} \leq$21 μm) or between about 20 μm and about 10 μm (10 μm$\leq D_{60} \leq$20 μm), preferably between about 25 μm and about 10 μm (10 μm$\leq D_{60} \leq$25 μm).

In particular embodiments, the MSC-derived cells in suspension exhibit a $D_{65}$ between about 25 μm and about 10 μm (10 μm$\leq D_{65} \leq$25 μm), between about 24 μm and about 10 μm (10 μm$\leq D_{65} \leq$24 μm), between about 23 μm and about 10 μm (10 μm$\leq D_{65} \leq$23 μm), between about 22 μm and about 10 μm (10 μm$\leq D_{65} \leq$22 μm), between about 21 μm and about 10 μm (10 μm$\leq D_{65} \leq$21 μm) or between about 20 μm and about 10 μm (10 μm$\leq D_{65} \leq$20 μm), preferably between about 25 μm and about 10 μm (10 μm$\leq D_{65} \leq$25 μm).

In particular embodiments, the MSC-derived cells in suspension exhibit a $D_{70}$ between about 25 μm and about 10 μm (10 μm$\leq D_{70} \leq$25 μm), between about 24 μm and about 10 μm (10 μm$\leq D_{70} \leq$24 μm), between about 23 μm and about 10 μm (10 μm$\leq D_{65} \leq$23 μm), between about 22 μm and about 10 μm (10 μm$\leq D_{70} \leq$22 μm), between about 21 μm and about 10 μm (10 μm$\leq D_{70} \leq$21 μm) or between about 20 μm and about 10 μm (10 μm$\leq D_{70} \leq$20 μm), preferably between about 25 μm and about 10 μm (10 μm$\leq D_{70} \leq$25 μm).

In particular embodiments, the MSC-derived cells in suspension exhibit a $D_{75}$ between about 25 μm and about 10 μm (10 μm$\leq D_{75} \leq$25 μm), between about 24 μm and about 10 μm (10 μm$\leq D_{75} \leq$24 μm), between about 23 μm and about 10 μm (10 μm$\leq D_{75} \leq$23 μm), between about 22 μm and about 10 μm (10 μm$\leq D_{75} \leq$22 μm), between about 21 μm and about 10 μm (10 μm$\leq D_{75} \leq$21 μm) or between about 20 μm and about 10 μm (10 μm$\leq D_{75} \leq$20 μm), preferably between about 25 μm and about 10 μm (10 μm$\leq D_{75} \leq$25 μm).

In particular embodiments, at least 90% of the MSC-derived cells in suspension have a diameter equal to or less than 30 μm ($D_{90} \leq 30$ μm), equal to or less than 29 μm ($D_{90} \leq 29$ μm), equal to or less than 28 μm ($D_{90} \leq 28$ μm), equal to or less than 27 μm ($D_{90} \leq 27$ μm), equal to or less than 26 μm ($D_{90} \leq 26$ μm) or equal to or less than 25 μm ($D_{90} \leq 25$ μm), preferably equal to or less than 30 μm ($D_{90} \leq 30$ μm).

In particular embodiments, the MSC-derived cells in suspension exhibit a Do equal to or less than 30 μm ($D_{90} \leq 30$ μm) and at most 5% of the MSC-derived cells in suspension have a diameter of more than 35 μm.

In particular embodiments, the MSC-derived cells in suspension exhibit a Do between about 30 μm and about 10 μm (10 μm$\leq$0 Do s 30 μm).

In particular embodiments, the diameter of each MSC-derived cell in suspension is more than 10 μm, more than 11 μm, more than 12 μm, more than 13 μm, more than 14 μm or more than 15 μm, preferably more than 10 μm.

The diameter of a cell may be determined by any method known in the art, for example by a digital microscope and accompanying software for image analysis (e.g., Motic Image Plus 2.02). The average cell diameter as referred to herein should be determined based on the diameter of the cells in a free-floating, non-attached state, hence of the cells in suspension. The cells are preferably suspended in a solution comprising a transparent, non-toxic, isotonic buffer, such as PBS, and optionally a dye to differentiate living and dead cells, such as trypan blue. Preferably, at least hundred cells should be measured to consider the analysis statistically significant.

In particular embodiments, the diameter of each MSC-derived cell in suspension is less than 38 μm, less than 37 μm, less than 36 μm, less than 35 μm, preferably less than 35 μm.

In particular embodiments, the standard deviation of the average diameter of the MSC-derived cells in suspension is less than 7.0 μm, less than 6.5 μm, less than 6.0 μm, less than 5.5 μm, less than 5 μm, less than 4.5 μm, less than 4 μm or less than 3.5 μm. Preferably, the standard deviation of the average diameter of the MSC-derived cells in suspension is less than 4.0 μm, such as between 3.0 and 3.5 μm.

The inventors found that the cell size distribution of MSC-derived cells obtained by the methods as described herein is stable. Accordingly, the diameter and/or volume of the MSC-derived cells obtained by the methods as described herein may be determined at any time point and at any confluency during in vitro culture. In preferred embodiments, the diameter and/or volume of the MSC-derived cells is determined when the cells reach a confluency of between 30% and 80%, preferably of between 40% and 70%, such as 40%, 45%, 50%, 55%, 60%, 65% or 70%.

A further aspect provides a method for obtaining MSC-derived cells from MSC comprising contacting MSC in vitro or ex vivo with FGF-2, TGFβ and heparin or a derivative or analogue thereof, wherein average diameter of the MSC-derived cells in suspension is less than 25 μm, such as less than 24 μm or such as between 20 μm and 25 μm.

A further aspect provides a method for obtaining MSC-derived cells from MSC comprising contacting MSC in vitro or ex vivo with FGF-2, TGFβ and heparin or a derivative or analogue thereof, whereby at least 60% of the MSC-derived cells in suspension have a diameter equal to or less than 25 μm ($D_{60} \leq 25$ μm), preferably at least 70% of the MSC-derived cells in suspension have a diameter equal to or less than 25 μm ($D_{70} \leq 25$ μm), and at most 5% of the cell population have a diameter of more than 35 μm.

It will be clear to the skilled person that all embodiments described earlier, including those embodiments relating to the average diameter of the MSC-derived cells, maximal individual diameter of the MSC-derived cells, average volume of the MSC-derived cells, $D_{60}$, $D_{65}$, $D_{70}$, $D_{75}$, $D_{90}$, concentration of heparin or derivative or analogue thereof, lineage of MSC-derived cells and agents capable of inducing expansion and/or differentiation of MSC, apply to all methods for obtaining MSC-derived cells as taught herein.

A further aspect provides a population of MSC-derived cells obtainable by in vitro or ex vivo expansion of MSC, wherein average diameter of the MSC-derived cells in suspension is less than 30 μm, less than 29 μm, less than 28 μm, less than 27 μm, less than 26 μm, less than 25 μm or less than 24 μm. Preferably, the average diameter of the MSC-derived cells in suspension is less than 24 μm.

A further aspect provides a population of MSC-derived cells obtainable by in vitro or ex vivo expansion of MSC, whereby at least 60% of the MSC-derived cells in suspension have a diameter equal to or less than 25 μm ($D_{60} \leq 25$ μm), preferably at least 70% of the MSC-derived cells in suspension have a diameter equal to or less than 25 μm ($D_{70} \leq 25$ μm), and at most 5% of the cell population have a diameter of more than 35 μm. The term "population" as used herein refers to a substantially pure (i.e., composed primarily of) and homogeneous group of cells of a desired MSC-derived cell type.

In particular embodiments, the diameter of each MSC-derived cell in suspension is less than 38 μm, less than 37 μm, less than 36 μm, preferably less than 35 μm.

In particular embodiments, the standard deviation of the average diameter of the MSC-derived cells in suspension is less than 6.0 μm, less than 5.5 μm, less than 5.0 μm, less than 4.5 μm, less than 4.0 μm or less than 3.5 μm. Preferably, the standard deviation of the average diameter of the MSC-derived cells in suspension is less than 4.0 μm, such as between 3.0 and 3.5 μm.

In particular embodiments, the population of MSC-derived cells is obtainable by the methods for obtaining MSC-derived cells from MSC as taught herein.

It will be clear to the skilled person that all embodiments described earlier, including those embodiments relating to the average diameter of the MSC-derived cells, maximal individual diameter of the MSC-derived cells, average volume of the MSC-derived cells, $D_{60}$, $D_{65}$, $D_{70}$, $D_{75}$, $D_{90}$, concentration of heparin or derivative or analogue thereof, lineage of MSC-derived cells and agents capable of inducing expansion and/or differentiation of MSC, apply to all methods for obtaining MSC-derived cells from MSC as taught herein, and hence, also to MSC-derived cells and a population of MSC-derived cells obtainable by said methods as taught herein.

Accordingly, a further aspect relates to a composition comprising the MSC-derived cells or the population of MSC-derived cells as defined herein. Also provided are compositions comprising the herein taught MSC-derived cells or the population of MSC-derived cells and further comprising one or more other components. For example, components may be included that can maintain or enhance the viability of cells. By means of example and without limitation, such components may include salts to ensure substantially isotonic conditions, pH stabilisers such as buffer system(s) (e.g., to ensure substantially neutral pH, such as phosphate or carbonate buffer system), carrier proteins such as for example albumin, media including basal media and/or media supplements, serum or plasma, nutrients, carbohydrate sources, preservatives, stabilisers, antioxidants or other materials well known to those skilled in the art. Also disclosed are methods of producing said compositions by admixing the respective MSC-derived cells or population of MSC-derived cells with said one or more additional components as above. The compositions may be for example liquid or may be semi-solid or solid (e.g., may be frozen compositions or may exist as gel or may exist on solid support or scaffold, etc.). Cryopreservatives such as inter alia dimethyl sulfoxide (DMSO) are well known in the art.

The terms "composition", "formulation", or "preparation" may be used interchangeably herein.

In particular embodiments, the composition is a pharmaceutical composition comprising the MSC-derived cells or the population of MSC-derived cells as defined herein, and optionally one or more pharmaceutically acceptable excipients.

The term "pharmaceutically acceptable" as used herein is consistent with the art and means compatible with the other ingredients of a pharmaceutical composition and not deleterious to the recipient thereof.

As used herein, "carrier" or "excipient" includes any and all solvents, diluents, buffers (e.g., neutral buffered saline or phosphate buffered saline), solubilizers, colloids, dispersion media, vehicles, fillers, chelating agents (e.g., EDTA or glutathione), amino acids (e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for pharmaceutical active substances is well known in the art. Such materials should be non-toxic and should not interfere with the activity of the cells.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of its environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregeletanized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants. For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g., by impregnating said support with a liquid suspension containing said cells. The impregnated supports obtained in this way can be implanted in a subject. Such impregnated supports can also be re-cultured by immersing them in a liquid culture medium, prior to being finally implanted. The three-dimensional solid support needs to be biocompatible so as to enable it to be implanted in a human. It may be biodegradable or non-biodegradable.

The cells or cell populations can be administered in a manner that permits them to survive, grow, propagate and/or differentiate towards desired cell types such as, e.g., hepatocytes. The cells or cell populations may be grafted to or may migrate to and engraft within the intended organ, such as, e.g., liver. Engraftment of the cells or cell populations in other places, tissues or organs such as liver, spleen, pancreas, kidney capsule, peritoneum or omentum may be envisaged.

In an embodiment, the pharmaceutical cell preparation as defined above may be administered in a form of liquid composition. In embodiments, the cells or pharmaceutical composition comprising such can be administered systemically, topically, within an organ, at a site of organ dysfunction or lesion or at a site of tissue lesion.

Preferably, the pharmaceutical compositions may comprise a therapeutically effective amount of the desired cells. The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated. Appropriate therapeutically effective amounts may be determined by a qualified physician with due regard to the nature of the desired cells, the disease condition and severity, and the age, size and condition of the subject.

Also provided are methods of producing said pharmaceutical compositions by admixing the cells of the invention with one or more additional components as described above as well as with one or more pharmaceutical excipients as described above.

Also disclosed is an arrangement or kit of parts comprising a surgical instrument or device for administration of the MSC-derived cells or the population of MSC-derived cells as taught herein or the pharmaceutical compositions as defined herein to a subject, such as for example systemically, for example, by injection, and further comprising the MSC-derived cells or the population of MSC-derived cells as taught herein or the pharmaceutical compositions as defined herein.

In an embodiment, the pharmaceutical composition as define above may be administered in a form of liquid or viscous composition.

In related aspects, the invention provides the above defined MSC-derived cells or MSC-derived cell populations or the pharmaceutical composition comprising said MSC-derived cells or MSC-derived cell population for use as a medicament. In related aspects, the invention provides the above defined MSC-derived cells or MSC-derived cell populations or the pharmaceutical composition comprising said MSC-derived cells or MSC-derived cell population for use in the treatment of a subject in need of transplantation of MSC-derived cells. In related aspects, the invention provides a method of treating a subject in need of transplantation of MSC-derived cells comprising administering to said subject a therapeutically effective amount of the above defined MSC-derived cells or MSC-derived cell populations or the pharmaceutical composition comprising said MSC-derived cells or MSC-derived cell population to the subject. In related aspects, the invention provides the use of the above defined MSC-derived cells or a MSC-derived cell population or composition comprising said MSC-derived cells or a MSC-derived cell population for the manufacture of a medicament for treatment of a subject in need of transplantation of MSC-derived cells.

As used herein, the terms "treat" or "treatment" refer to both therapeutic treatment and prophylactic or preventative measures, wherein the object is to prevent or slow down (lessen) an undesired physiological change or disorder. Beneficial or desired clinical results include, but are not limited to, alleviation of symptoms, diminishment of extent of disease, stabilised (i.e., not worsening) state of disease, delay or slowing of disease progression and occurrence of complications, amelioration or palliation of the disease state. "Treatment" can also mean prolonging survival as compared to expected survival if not receiving treatment.

The term "subject in need of transplantation of MSC-derived cells" as used herein, includes subjects, such as mammalian or human subjects, that would benefit from treatment of a given condition, preferably a condition or disease as above. Such subjects will typically include, without limitation, those that have been diagnosed with the condition, those prone to have or develop the said condition and/or those in whom the condition is to be prevented.

The term "transplantation" or "cell transplantation" carries its normal meaning and particularly refers to the administration of cells to a subject. The term "cell transplantation" can be used interchangeably with "cell therapy". Cell transplantation may be performed by any technique known in the art. By means of example, and without limitation, cells may be transplanted by infusion into a subject. Typically, cell infusion may be performed parenterally, e.g., intravascularly, subcutaneously, intradermally, or intramuscularly, preferably intravascularly. Cells may be administered for instance, and without limitation, systemically, topically or at the site of a lesion.

It may be clear that, depending on the specific application, targeted tissues, therapeutic purpose or cell type, adjustment may be made accordingly in respect of routes of administration, as well as formulations, concentrations, etc.

The homogeneous and small cell size of the MSC-derived cells as taught herein leads to a reduced or abrogated acute toxicity upon intravenous administration of said cells to a subject.

Therefore, the MSC-derived cells as taught herein are particular suitable for intravascular or percutaneous administration.

Therefore, in particular embodiments, the above defined MSC-derived cells or population of MSC-derived cells or the pharmaceutical composition may be administered to said subject in need of transplantation of MSC-derived cells percutaneous or intravascular.

Furthermore, the inventors found that MSC-derived cells of osteochondroblastic lineage or osteoblastic lineage would be obtained by the methods as taught herein which have more potent bone-forming properties.

Accordingly, in a particular embodiment, said condition or disease is a musculoskeletal disease.

The term "musculoskeletal disease", as used herein, refers to any type of bone disease, muscle disease, joint disease, or chondrodystrophy, the treatment of which may benefit from the administration of the present pharmaceutical formulation to a subject having the disease. In particular, such disease may be characterized, e.g., by decreased bone and/or cartilage formation or excessive bone and/or cartilage resorption, by decreased number, viability or function of osteoblasts or osteocytes present in the bone and/or chondroblasts or chondrocytes present in the cartilage, decreased bone mass and/or cartilage mass in a subject, thinning of bone, compromised bone strength or elasticity, etc.

Non-limiting examples of musculoskeletal diseases may include local or systemic disorders, such as, any type of osteoporosis or osteopenia, e.g., primary, postmenopausal, senile, corticoid-induced, bisphosphonates-induced, and radiotherapy-induced; any secondary, mono- or multisite osteonecrosis; any type of fracture, e.g., non-union, malunion, delayed union fractures or compression, maxillofacial fractures; conditions requiring bone fusion (e.g., spinal fusions and rebuilding); congenital bone defect; bone reconstruction, e.g., after traumatic injury or cancer surgery, and cranio-facial bone reconstruction; traumatic arthritis, focal cartilage and/or joint defect, focal degenerative arthritis; osteoarthritis, degenerative arthritis, gonarthrosis, and coxarthrosis; osteogenesis imperfecta; osteolytic bone cancer; Paget's Disease; endocrinological disorders; hypophosphatemia; hypocalcemia; renal osteodystrophy; osteomalacia; adynamic bone disease, hyperparathyroidism, primary hyperparathyroidism, secondary hyperparathyroidism; periodontal disease; Gorham-Stout disease and McCune-Albright syndrome; rheumatoid arthritis; spondyloarthropathies, including ankylosing spondylitis, psoriatic arthritis, enteropathic arthropathy, and undifferentiated spondyloarthritis and reactive arthritis; systemic lupus erythematosus and related syndromes; scleroderma and related disorders; Sjogren's Syndrome; systemic vasculitis, including Giant cell arteritis (Horton's disease), Takayasu's arteritis, polymyalgia rheumatica, ANCA-associated vasculitis (such as Wegener's granulomatosis, microscopic polyangiitis, and Churg-Strauss Syndrome), Behcet's Syndrome, and other polyarteritis and related disorders (such as polyarteritis nodosa, Cogan's Syndrome, and Buerger's disease); arthritis accompanying other systemic inflammatory diseases, including amyloidosis and sarcoidosis; crystal arthropathies, including gout, calcium pyrophosphate dihydrate disease, disorders or syndromes associated with articular deposition of calcium phosphate or calcium oxalate crystals; chondrocalcinosis and neuropathic arthropathy; Felty's Syndrome and Reiter's Syndrome; Lyme disease and rheumatic fever.

In a particular embodiment, said condition or disease is a bone-related disorder.

Accordingly, the term "bone-related disorder" as used herein refers to any type of bone disease, the treatment of which may benefit from the transplantation of cells with bone-forming properties, e.g., osteochondroprogenitors, osteoprogenitors, pre-osteoblasts, osteoblasts or osteoblast phenotype cells to a subject having the disorder. In particular, such disorders may be characterized, e.g., by decreased bone formation or excessive bone resorption, by decreased number, viability or function of osteoblasts or osteocytes present in the bone, decreased bone mass in a subject, thinning of bone, compromised bone strength or elasticity, etc.

By way of example, but not limitation, bone-related disorders which can benefit from transplantation of MSC-derived cells with bone-forming properties (e.g. cells of osteoblastic lineage) obtained by the method of the present invention may include local or systemic disorders, such as, any type of osteoporosis or osteopenia, e.g., primary, post-menopausal, senile, corticoid-induced, any secondary, mono- or multisite osteonecrosis, any type of fracture, e.g., non-union, mal-union, delayed union fractures or compression, conditions requiring bone fusion (e.g., spinal fusions and rebuilding), maxillo-facial fractures, bone reconstruction, e.g., after traumatic injury or cancer surgery, craniofacial bone reconstruction, osteogenesis imperfecta, osteolytic bone cancer, Paget's Disease, endocrinological disorders, hypophosphatemia, hypocalcemia, renal osteodystrophy, osteomalacia, adynamic bone disease, rheumatoid arthritis, hyperparathyroidism, primary hyperparathyroidism, secondary hyperparathyroidism, periodontal disease, Gorham-Stout disease and McCune-Albright syndrome.

The MSC-derived cells, the population of MSC-derived cells and pharmaceutical compositions described herein may be used alone or in combination with any of the known therapies or active compounds for the respective disorders. The administration may be simultaneous or sequential in any order, as described elsewhere.

If the cells are derived from heterologous (i.e., non-autologous, non-homologous or non-allogeneic) source, concomitant immunosuppression therapy may be typically administered, e.g., using immunosuppressive agents, such as cyclosporine or tacrolimus (FK506).

The quantity of cells to be administered will vary for the subject being treated. In a preferred embodiment, the quantity of cells to be administered is between $10^2$ to $10^{10}$ or between $10^2$ to $10^9$, or between $10^3$ to $10^{10}$ or between $10^3$ to $10^9$, or between $10^4$ to $10^{10}$ or between $10^4$ to $10^9$, such as between $10^4$ and $10^8$, or between $10^5$ and $10^7$, e.g., about $1\times10^5$, about $5\times10^5$, about $1\times10^6$, about $5\times10^6$, about $1\times10^7$, about $5\times10^7$, about $1\times10^8$, about $5\times10^8$, about $1\times10^9$, about $2\times10^9$, about $3\times10^9$, about $4\times10^9$, about $5\times10^9$, about $6\times10^9$, about $7\times10^9$, about $8\times10^9$, about $9\times10^9$ or about $1\times10^{10}$ cells can be administered to a human subject. In further embodiments, between 10 to $10^8$ cells per kg body weight or between $1\times10^7$ to $9\times10^7$ cells per kg body weight, e.g., about $1\times10^7$, about $2\times10^7$, about $3\times10^7$, about $4\times10^7$, about $5\times10^7$, about $6\times10^7$, about $7\times10^7$, about $8\times10^7$, about $9\times10^7$ or about $1\times10^8$ cells per kg body weight can be administered to a human subject. For example, such number of cells or such number of cells per kg body weight may particularly refer to the total number of cells to be administered to a subject, which administration may be suitably distributed over one or more doses (e.g., distributed over 2, 3, 4, 5, 6, 7, 8 9 or 10 or more doses) administered over one or more days (e.g., over 1, 2, 3, 4 or 5 or more days).

However, the precise determination of a therapeutically effective dose may be based on factors individual to each patient, including their size, age, size tissue damage, and amount of time since the damage occurred, and can be readily ascertained by those skilled in the art from this disclosure and the knowledge in the art.

Suitably, in a composition to be administered, cells may be present at a concentration between about $10^4$/ml to about $10^9$/ml, preferably between about $10^5$/ml and about $10^8$/ml, yet more preferably between about $1\times10^6$/ml and about $1\times10^8$/ml, yet more preferably between about $1\times10^7$/ml and about $1\times10^8$/ml, such as, e.g., about $7.5\times10^7$/ml. The reduced cell size of the MSC-derived cells as taught herein allows a tunable and/or high cell concentration. Accordingly, if the composition is a liquid composition, the volume of the composition comprising MSC-derived cells obtained by the method as taught herein to be administered to the subject in need of transplantation of MSC-derived cells is smaller than the volume of the composition comprising MSC-derived cells obtained by other methods.

Aspects and embodiments of the present invention hence encompass, and the present specification describes, subject-matter as set forth in any one and all of the following Statements:

Statement 1. A method for obtaining mesenchymal stem cell-derived cells from mesenchymal stem cells (MSC) comprising contacting MSC in vitro or ex vivo with FGF-2, TGFβ and heparin or a derivative or analogue thereof at a concentration of at least 0.01 IU/ml.

Statement 2. The method according to statement 1, comprising the steps of:
(a) culturing MSC recovered from a biological sample of a subject in a medium comprising FGF-2, TGFβ and heparin or derivative or analogue thereof at a concentration of at least 0.01 IU/ml;
(b) removing non-adherent matter and further culturing adherent cells in the medium comprising FGF-2, TGFβ and heparin or a derivative or analogue thereof at a concentration of at least 0.01 IU/ml, thereby obtaining the MSC-derived cells.

Statement 3. The method according to statement 1 or 2, wherein TGFβ is selected from the group consisting of TGFβ1, TGFβ2, TGFβ3, and mixtures thereof; preferably wherein TGFβ is TGFβ1.

Statement 4. A method for obtaining MSC-derived cells with improved transplantation properties from MSC, the method comprising a size reduction step, wherein said size reduction step is characterized by contacting MSC or MSC-derived cells in vitro or ex vivo with heparin or a derivative or analogue thereof at a concentration of at least 0.01 IU/ml.

Statement 5. The method according to any one of statements 1 to 4, wherein the concentration of heparin or derivative or analogue thereof is at least 0.05 IU/ml, preferably about 0.1 IU/ml.

Statement 6. The method according to any one of statements 1 to 5, wherein heparin or heparin derivative or analogue is selected from the group consisting of unfractionated heparin (UFH); low molecular weight heparin (LMWH), such as enoxaparin, dalteparin, nadroparin, tinzaparin, certoparin, reviparin, ardeparin, parnaparin, bemiparin, or mixtures thereof; a heparinoid, such as heparan sulfate, dermatan sulfate, chondroitin sulfate, acharan sulfate, keratan sulfate, or mixtures thereof, such as danaparoid; a heparin salt; a heparinoid salt; a heparin fragment; a heparinoid fragment; and mixtures thereof.

Statement 7. The method according to any one of statements 1 to 6, wherein average diameter of the MSC-derived cells in suspension is less than 25 µm, such as less than 24 µm, such as between 20 µm and 25 µm.

Statement 8. The method according to any one of statements 1 to 7, wherein the diameter of each MSC-derived cell in suspension is less than 35 µm.

Statement 9. The method according to any one of statements 1 to 8, whereby at least 60% of the MSC-derived cells in suspension have a diameter equal to or less than 25 µm ($D_{60} \leq 25$ µm) and wherein at most 5% of the MSC-derived cells in suspension have a diameter of more than 35 µm.

Statement 10. The method according to any one of statements 1 to 9, wherein the MSC-derived cells are of osteochondroblastic lineage.

Statement 11. The method according to any one of statements 1 to 10, wherein the MSC-derived cells are of osteoblastic or chondroblastic lineage, preferably of osteoblastic lineage.

Statement 12. The method according to any one of statements 1 to 11, wherein the MSC are additionally contacted with, such as wherein the medium additionally comprises one or more of, plasma, serum or a substitute thereof.

Statement 13. A method for obtaining MSC-derived cells from MSC comprising contacting MSC in vitro or ex vivo with FGF-2, TGFβ, and heparin or a derivative or analogue thereof, wherein average diameter of the MSC-derived cells in suspension is less than 25 µm, such as less than 24 µm, such as between 20 µm and 25 µm.

Statement 14. The method according to statement 13, wherein the diameter of each MSC-derived cell in suspension is less than 35 µm.

Statement 15. A method for obtaining MSC-derived cells from MSC comprising contacting MSC in vitro or ex vivo with FGF-2, TGFβ, and heparin or a derivative or analogue thereof, whereby at least 60% of the MSC-derived cells in suspension have a diameter equal to or less than 25 µm ($D_{60} \leq 25$ µm) and wherein at most 5% of the MSC-derived cells in suspension have a diameter of more than 35 µm.

Statement 16. The method according to any one of statements 13 to 15, wherein MSC are contacted with heparin or derivative or analogue thereof at a concentration of at least 0.01 IU/ml.

Statement 17. The method according to any one of statements 13 to 16, wherein TGFβ is selected from the group consisting of TGFβ1, TGFβ2, TGFβ3, and mixtures thereof; preferably wherein TGFβ is TGFβ1.

Statement 18. A population of MSC-derived cells obtainable by in vitro or ex vivo expansion of MSC, wherein average diameter of the MSC-derived cells in suspension is less than 25 µm, such as less than 24 µm, such as between 20 µm and 25 µm.

Statement 19. The population of MSC-derived cells according to statement 18, wherein the diameter of each MSC-derived cell in suspension is less than 35 µm.

Statement 20. A population of MSC-derived cells obtainable by in vitro or ex vivo expansion of MSC, whereby at least 60% of the MSC-derived cells in suspension have a diameter equal to or less than 25 µm ($D_{60} \leq 25$ µm) and wherein at most 5% of the MSC-derived cells in suspension have a diameter of more than 35 µm.

Statement 21. The population of MSC-derived cells according to any one of statements 18 to 20, wherein the MSC-derived cells are obtainable by a method comprising contacting MSC in vitro or ex vivo with FGF-2, TGFβ, and heparin or a derivative or analogue thereof.

Statement 22. The population of MSC-derived cells according to statement 21, wherein MSC are contacted with heparin or derivative or analogue thereof at a concentration of at least 0.01 IU/ml.

Statement 23. The population of MSC-derived cells according to any one of statements 18 to 22, wherein the MSC-derived cells are of osteochondroblastic lineage.

Statement 24. The population of MSC-derived cells according to any one of statements 18 to 23, wherein the MSC-derived cells are of osteoblastic or chondroblastic lineage, preferably of osteoblastic lineage.

Statement 25 The population of MSC-derived cells according to any one of statements 18 to 24, wherein the MSC are additionally contacted with one or more of plasma, serum or a substitute thereof.

Statement 26. The population of MSC-derived cells according to any one of statements 18 to 25, wherein TGFβ is selected from the group consisting of TGFβ1, TGFβ2, TGFβ3, and mixtures thereof; preferably wherein TGFβ is TGFβ1.

Statement 27. The population of MSC-derived cells of osteochondroblastic lineage according to any one of statements 23 to 27, wherein substantially all MSC-derived cells of osteochondroblastic lineage are positive for CD90, CD105, CD73, CD63 and CD166; substantially all MSC-derived cells of osteochondroblastic lineage are negative for CD45, CD14 and CD19; at least 70% of the MSC-derived cells of osteochondroblastic lineage are positive for alkaline phosphatase (ALP); and less than 10% of the MSC-derived cells of osteochondroblastic lineage are positive for HLA-DR.

Statement 28. A pharmaceutical composition comprising the population of MSC-derived cells as defined in any one of statements 18 to 27.

Statement 29. The population of MSC-derived cells according to any one of statements 18 to 27 or the pharmaceutical composition according to statement 28 for use as a medicament.

Statement 30. The population of MSC-derived cells for use according to statement 29, wherein the population of MSC-derived cells is present at a concentration between about $1 \times 10^7$/ml and about $1 \times 10^8$/ml, preferably $7.5 \times 10^7$ cells/ml.

Statement 31. The population of MSC-derived cells according to any one of statements 18 to 27 or the pharmaceutical composition according to statement 28 for use in treating a subject in need of transplantation of MSC-derived cells.

Statement 32. The population of MSC-derived cells for use according to any one of statements 29 to 31, wherein the population of MSC-derived cells or the pharmaceutical composition is suitable for percutaneous or intravascular administration.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The above aspects and embodiments are further supported by the following non-limiting examples.

EXAMPLES

Example 1: Method for Obtaining Small Sized MSC-Derived Bone-Forming Cells

1. Experimental Procedures 1.1 Human Bone Marrow Harvesting and Human BM-MSC Cultures 20 to 60 ml of human bone marrow (BM) aspirates was obtained from the iliac crest of 8 healthy volunteer donors. After harvesting, bone marrow white blood cells were counted, seeded at a density of 50,000 cells/cm$^2$ in conventional culture medium containing 1% penicillin-streptomycin and incubated at 37° C. in a humidified atmosphere containing 5% $CO_2$. After 24 hours, non-adherent cells were removed by rinsing with Phosphate Buffered Saline (PBS) (Lonza BioWhittaker®) and fresh medium was added. Culture medium was replaced every 2-3 days. Colonies of adherent cells were cultured until 80% of cell confluency were reached. Cells were then detached with trypsin-EDTA (TrypZean® EDTA, Lonza BioWhittaker®). Trypsin activity was neutralized by Dulbecco's Phosphate Buffered Saline (DPBS). Cells were counted and re-plated for an additional culture. Culture medium was replaced every 2-3 days until 80% of cell confluency were reached. Mesenchymal stem cells (MSC) were detached as described above.

1.2 MSC-Derived Bone-Forming Cells and Cell Culture and Plasma Preparation

As described above, 20 to 60 ml of heparinized bone marrow (BM) was obtained from iliac crest of 8 healthy human volunteers. After harvesting, bone marrow was seeded into culture flasks at a fixed white blood cell density (50000 cells/cm$^2$) and cultured either in to obtain MSC-derived bone-forming cells B: a conventional culture medium supplemented with 5% v/v solvent/detergent-treated (S/D) plasma (Octaplas®, Octapharma AG, human origin), 0.1 IU/ml heparin (Heparin LEO, LEO Pharma SA, Belgium, lot A17605), basic fibroblast growth factor (FGF-2) and transforming growth factor beta (TGFβ1);

to obtain MSC-derived bone-forming cells Z: a conventional culture medium supplemented with 5% v/v solvent/detergent-treated (S/D) plasma (Octaplas®, Octapharma AG, human origin) and basic fibroblast growth factor (FGF-2); or to obtain MSC-derived bone-forming cells A: a conventional culture medium supplemented with 5% v/v solvent/detergent-treated (S/D) plasma (Octaplas®, Octapharma AG, human origin), basic fibroblast growth factor (FGF-2) and transforming growth factor beta (TGFβ1).

Cells were cultured in a 37° C. humidified atmosphere containing 5% $CO_2$. MSC were allowed to attach prior to an initial medium change. Medium was changed each 3 or 4 days. At the end of primary culture, cells were detached, using trypsin/EDTA solution for 1-5 min at 37° C., counted and re-plated for secondary culture in culture flasks in the same medium. At the end of secondary culture, the MSC-derived bone-forming cells were harvested and washed with PBS.

1.3 In Vitro Cell Characterization 1.3.1. Cell Counting and Viability Cell density and viability were determined using a trypan blue exclusion assay. After harvesting, cells were diluted 1:2 with Trypan Blue (0.4%, Lonza BioWhittaker®) and cell viability was analysed using a Burker chamber (Sigma-Aldrich®) and an inverted microscope (AE31, Motic®). Cell viability was also analysed by flow cytometry using Amino-Actinomycin D (7-AAD, BD Biosciences®), the BD FACSCanto II™ and the BD FACS-Diva™ softwares (Becton Dickinson®). After harvesting, 50,000 cells were incubated in the dark for 10 min at room temperature in PBS-1% Bovine Serum Albumin (BSA) (Lonza BioWhittaker®) with 2.5 µl of 7-AAD.

1.3.2 Marker Expression 1.3.2.1 Flow Cytometry Analysis

MSC-derived bone-forming cells obtained after secondary culture, as described in Section 1.1 above, were harvested and cell surface markers were analysed by flow cytometry (BD FACSCanto II™ and the BD FACSDiva™ softwares; Becton Dickinson, USA). Cells were incubated with the following conjugated monoclonal antibodies: anti-CD73, anti-CD90, anti-CD105 and anti-CD166 (which are mesenchymal markers, and should be highly expressed by the MSC or MSC-derived cells), anti-CD3, anti-CD34 and anti-CD45 (which are hematopoietic markers, and should be substantially absent from the MSC or MSC-derived cells), anti-CD44, anti-CD 51/61, anti-CD49a-e, anti-CD29 (which are adhesion markers), anti-CD40, anti-CD86 and anti-HLA-DR (which are immunogenicity markers), and anti-alkaline phosphatase (ALP) for 15 min at room temperature, and then washed with phosphate-buffered saline (PBS) before centrifugation and re-suspension in 0.3 ml PBS.

For the characterization of cell surface markers CD105, CD73, CD10 and CD44, 50 000 cells at a concentration of 1×10$^6$ cells/ml in PBS—1% BSA were incubated 10 min in the dark with 5 µl of antibodies. After this incubation time, cells were washed once with PBS. The different antibodies used for extracellular staining are the following: allophycocyanin (APC)-conjugated antibodies against CD105 (BD Biosciences®, Cat No.: 562408), CD73 (BD Biosciences®, Cat No.:560847), Phycoerythrin (PE)-conjugated antibodies against CD10 (BD Biosciences®, Cat No.: 555375), CD44 (BD Biosciences®, Cat No.: 550989). Nonspecific staining was determined by incubating cells with immunoglobulin G (IgG) control conjugated with FITC, APC and PE (all BD Biosciences®, Cat No.: 556649; 555751; 556650 respectively). Before analysis, gating of singulets and population of interest were performed. The flow cytometry analysis was done on 10 000 events of the gated population using FACS CantoII (BD Biosciences®) and FACS Diva® 8.0 software (BD Biosciences®). Settings parameters used for the analysis were performed automatically with beads (BD Comp-Beads Plus®, Cat No. 560497). For each conjugate, the positivity cut-off was fixed at 1% of positivity of the control isotype antibody and the positivity of each marker was determined. The median of fluorescence intensity (MFI) of the whole analysed population was also determined and divided by the MFI of the corresponding isotype control antibody to obtain the normalized MFI (nMFI).

TABLE 1

Overview vendors and catalogue numbers of antibodies used in examples

| Anti-body | Supplier | Catalogue number |
|---|---|---|
| Anti-ALP | BD Biosciences | 561433 |
| Anti-CD166 | BD Biosciences | 560903 |
| Anti-CD3 | BD Biosciences | 555340 |
| Anti-CD34 | BD Biosciences | 555824 |
| Anti-CD40 | BD Biosciences | 555588 |
| Anti-CD44 | BD Biosciences | 550989 |
| Anti-CD45 | BD Biosciences | 555485 |
| Anti-CD49a | BD Biosciences | 559596 |
| Anti-CD49b | BD Biosciences | 555669 |

TABLE 1-continued

Overview vendors and catalogue numbers of antibodies used in examples

| Anti-body | Supplier | Catalogue number |
| --- | --- | --- |
| Anti-CD49c | BD Biosciences | 556025 |
| Anti-CD49d | BD Biosciences | 555503 |
| Anti-CD49e | BD Biosciences | 555617 |
| Anti-CD51/61 | BD Biosciences | 550037 |
| Anti-CD73 | BD Biosciences | 561254 |
| Anti-CD29 | BD Biosciences | 556048 |
| Anti-CD86 | BD Biosciences | 555660 |
| Anti-CD90 | R&D System | FAB7335P |
| Anti-HLA-DR | BD Biosciences | 555558 |
| Anti-CD105 | BD Biosciences | 562408 |
| Anti-CD10 | BD Biosciences | 555375 |
| Anti-HLA-DR-DP-DQ | BD Biosciences | 555558 |
| Anti-HLA-ABC | BD Biosciences | 555552 |

1.3.2.2. ALP Staining

Cells are plated at the end of manufacturing process at 60.000 cells/cm² in their respective culture medium and placed in humidified incubator (37° C.-5% $CO_2$). The ALP staining is performed after 24 hrs on adherent cells. Cells are fixed with citrated buffered acetone and incubated with ALP staining solution composed of 4% v/v naphtol AS-MX phosphate alkaline (Sigma; ref: 855) and 96% v/v fast blue RR salt solution (Sigma; ref: FBS25) for 30 min in the dark.

1.3.2.3. ALP Enzymatic Activity Measurement

ALP enzymatic activity was measured by a biochemical assay based on the hydrolysis of p-nitrophenyl phosphate (pNPP). After being dephosphorylated by ALP, the pNPP become yellow and can be detected by a spectrophotometer at 410 nm. The ALP enzymatic activity of the cells is determined with respect to a standard curve based on purified calf intestinal alkaline phosphatase activity. The ALP activity is reported in Unit of ALP/mg of protein. One unit of ALP hydrolyzes 1 µmol of pNPP in 1 min at 37° C.

1.3.3. Reverse Transcription-Quantitative Polymerase Chain Reaction (RT-gPCR)

After harvesting, cells were stored at −80° C. as dry pellets (500,000 cells) until RNA extraction. Total RNAs were extracted using RNeasy® Mini kit (Qiagen®) according to manufacturer's instructions. RNA concentration was measured using DropSense® 16 (Trinean®). RT were performed from 1 µg of total RNA extracts, using PrimeScript® RT reagent Kit (Takara®) according to manufacturer's instructions. qPCRs were performed using Premix Ex Taq® (Takara®) from 2 µl of cDNA following manufacturer's instructions. The expression levels of the following genes of interest were quantified: The expression levels of the following genes of interest were quantified: RUNX2 (Forward: GGTTCCAGCAGGTAGCTGAG (SEQ ID NO: 1), Reverse:AGACACCAAACTCCACAGCC (SEQ ID NO: 2)), SOX9 (F:TAAAGGCAACTCGTACCCAA (SEQ ID NO: 3), R: ATTCTCCATCATCCTCCACG (SEQ ID NO: 4), BMP2 (F:GGAACGGACATTCGGTCCTT (SEQ ID NO: 5), R:CACCATGGTCGACCTTTAGGA (SEQ ID NO: 6)), ALPL (F:ACCATTCCCACGTCTTCACATTTG (SEQ ID NO: 7), R: AGACATTCTCTCGTTCACCGCC (SEQ ID NO: 8)), MMP13 (F:TGGAATTAAGGAGCATGGCGA (SEQ ID NO: 9), R: AACTCATGCGCAGCAACAAG (SEQ ID NO: 10)), CHI3L1(F:TGGGTCTCAAAGAT-TTTCCAAGA (SEQ ID NO: 11), R: GCTGTTTGTCTCTCCGTCCA (SEQ ID NO: 12)), DCN (F:AAAATGCCCAAAACTCTTCAGG (SEQ ID NO: 13), R:GCCCCATTTTCAATTCCTGAG (SEQ ID NO: 14)), OCN (F:AAGGTGCAGCCTTTGTGT (SEQ ID NO: 15), R:GCTCCCAGCCATTGATACAG (SEQ ID NO: 16)), SPON1 (F:CCTGCGGAACTGCCAAGTA(SEQ ID NO: 17), R:CACGGGTGAGCCCAATTCT (SEQ ID NO: 18)), POSTN (F:TTTGGGCACCAAAAAGAAAT (SEQ ID NO: 19), R:TTCTCATATAACCAGGGCAACA (SEQ ID NO: 20)). qPCRs were run in duplicates using a LightCycler® 480 (Roche®). Normalization was performed using the geometric mean obtained from three housekeeping genes: RPL13A (F:CATAGGAAGCTGGGAGCAAG (SEQ ID NO: 21), R:GCCCTCCAATCAGTCTTCTG (SEQ ID NO: 22)), TBP (F:AACAACAGCCTGCCACCTTA (SEQ ID NO: 23), R:GCCATAAGGCATCATTGGAC (SEQ ID NO: 24)), HPRT (F:CCCTGGCGTCGTGATTAGT (SEQ ID NO: 25), R: GTGATGGCCTCCCATCTCCTT (SEQ ID NO: 26)). Comparison between the different MSC-derived cells products from the same donors were performed by calculating the gene expression (fold change) using the 2-ΔΔCt method for each gene of interest (Schmittgen and Livak, 2008, 3(6), 1101-8; *Nature Protocols*, 3(6), 1101-1108).

Statistical analysis was performed using JMP® (13.1.0) software. RT-qPCR data expressed in fold change were log transformed and Student tests (with α=0.05) were performed to evaluate the statistical significance of differences observed between cell types.

Statistical significance was graphically represented depending on the p-value (p) obtained: * for p<0.05,  for p<0.01, and * for p<0.001.

1.3.4. Multiplex Assay

After harvesting, cells were plated at a density of 50,000 cells/cm². After 48 hours of incubation at 37° C. in a humidified atmosphere containing 5% $CO_2$, cell culture supernatants were harvested, centrifuged (5 min at 1500 rpm at room temperature) and stored at −80° C. Supernatants were analysed by Luminex® assay using Human Magnetic Luminex® Assays (R&D System®). The premixed Multiplex was custom-made (R&D System®). The following secreted factors were investigated: BMP-2, COL1A1, MMP13, OPN, OPG, SPARC, RANKL, CHI3L1. The assay was performed following manufacturer's instructions and the analyses were performed using MAGPIX® (R&D System®) and the Bio-Plex Manager 5.0™ Software (Bio-Rad®).

1.4 Cell Size Measurement

The MSC-derived bone-forming cells obtained after secondary culture as described in Section 1.1 above were harvested and suspended in PBS with 0.4% trypan blue at a cell density of 12.5×10⁶ cells per ml. 10 µl of the cell suspension were placed on a graduated slide (Motic®) and then protected by a coverslip to be placed under an inverted microscope at magnification 40× (AE31; Motic). Images taken with a camera (Moticam) placed on the microscope were analysed by Motic Image Plus 2.02 software in order to measure cell diameters. At least hundred cells were measured to consider the analysis statistically significant.

The size of MSC-derived bone-forming cells obtained at different times of the ex vivo culture was also analysed by flow cytometry (BD FACS Canto II™ and the BD FACS Diva™ softwares; Becton Dickinson SA). Briefly, at day 21, 23, 26 and 28 after initiation of the ex vivo cell culture as described in Section 1.1, cells were harvested, suspended in phosphate-buffered saline (PBS) at a cell density of $1.10^6$ cells per ml and analysed with the flow cytometer for forward scatter (FSC) measurement (expressed in relative fluorescence unit). Forward scatter measures scattered light in the direction of the laser path, and therefore gives a relative size for the cells passing through the flow chamber.

2. Results

2.1 Cell Marker Expression Profile

Flow cytometry analysis revealed that the cell identities based on the cell surface marker expression profiles of bone-forming cells A (generated with FGF-2 and TGFβ-1) and bone-forming cells B (generated with FGF2, TGFβ1 and heparin; embodiment of present invention) were comparable.

Both bone-forming cells A and B populations expressed the mesenchymal markers CD73, CD90, CD105, CD63, CD166 and do not express the haematopoietic markers CD45, CD34 and CD3 (less than 5% of the cell population expressed these markers) (Tables 2 and 3). Bone-forming cells B (i) continued to express low levels of MHC class II cell surface receptor such as the HLA-DR and (ii) highly expressed ALP. Weak immunogenicity represented by weak expression of HLA-DR advantageously allows cell transplantation for instance to allogeneic subjects (Table 5). In addition, bone-forming cells A and bone-forming cells B highly expressed the adhesion markers CD49e, CD44 and the enzyme ALP on their surface compared to undifferentiated MSCs (Tables 3 and 4). The high expression of this last marker (ALP) highlights the commitment toward the osteoblastic lineage of bone-forming cells. Furthermore, the high expression of ALP evidences bone-forming cells B's commitment towards the osteoblastic lineage (vs. undifferentiated MSCs). Table 6 also shows that ALP expression was higher for cells cultured in presence of heparin (bone-forming cells B) than for cells cultured in absence of heparin (bone-forming cells A).

TABLE 2

Marker expression profile of MSC and MSC-derived bone-forming cell populations.

| % Marker expression (Mean ± SD) | MSCs | Bone-forming cells Z generated with FGF-2 | Bone-forming cells A generated with FGF-2 and TGFβ1 | Bone-forming cells B generated with FGF-2, TGFβ1 and heparin |
|---|---|---|---|---|
| CD44-FITC | 98 ± 2 (N = 3) | 100 ± 1 (N = 16) | 100 ± 1 (N = 11) | 100 ± 1 (N = 16) |
| CD51/61 | 19 ± 18 (N = 10) | 50 ± 17 (N = 8) | 13 ± 12 (N = 8) | 32 ± 31 (N = 8) |
| CD34-FITC | 3 ± 2 (N = 3) | 1 ± 1 (N = 3) | ND | ND |
| CD34-APC | 2 ± 1 (N = 6) | 3 ± 1 (N = 5) | ND | ND |
| CD49-FITC | 8 ± 8 (N = 10) | 44 ± 14 (N = 7) | 25 ± 13 (N = 7) | 42 ± 18 (N = 6) |
| CD45-FITC | 2 ± 1 (N = 6) | 2 ± 1 (N = 11) | 1 ± 1 (N = 11) | 2 ± 1 (N = 6) |
| CD166-PE | 97 ± 3 (N = 10) | 98 ± 2 (N = 8) | 97 ± 3 (N = 9) | 96 ± 6 (N = 8) |
| CD73-PE | 99 ± 1 (N = 6) | 100 ± 1 (N = 12) | 100 ± 1 (N = 11) | 100 ± 1 (N = 8) |
| CD29-APC | 100 ± 1 (N = 8) | 100 ± 1 (N = 7) | 100 ± 1 (N = 10)/ | 100 ± 1 (N = 8) |
| ALP-PE | 20 ± 7 (N = 13) | 70 ± 19 (N = 17) | 69 ± 18 (N = 16) | 91 ± 8 (N = 10) |
| ALP intra-PE | 19 ± 13 (N = 11) | 63 ± 22 (N = 10) | 59 ± 22 (N = 10) | 80 ± 13 (N = 8) |
| HLA-DR | NA | 63 ± 20 (N = 10) | 6 ± 6 (N = 22) | 3 ± 2 (N = 8) |

Abbreviations:
ALP: alkaline phosphatase;
APC: allophycocyanin;
FGF-2: fibroblast growth factor 2;
FITC: fluorescein isothiocyanate;
HLA-DR: human leukocyte antigen - DR isotype;
MSC: mesenchymal stem cells;
NA: not available;
ND: not determined;
PE: phycoerythrin;
SD: standard deviation;
TGFβ1: transforming growth factor beta 1

TABLE 3

Cell surface marker expression profile of MSC and MSC-derived bone-forming cell populations

| Marker expression (in %) | Statistics | MSCs | Bone-forming cells A | Bone-forming cells B |
|---|---|---|---|---|
| CD73-APC | Mean | 100.0 | 100.0 | 100.0 |
|  | SD | 0.0 | 0.0 | 0.0 |
|  | N | 6 | 11 | 22 |
| CD90-PE | Mean | 100.0 | 99.9 | 99.9 |
|  | SD | 0.1 | 0.2 | 0.2 |
|  | N | 8 | 12 | 22 |
| CD105-APC | Mean | 100.0 | 99.8 | 100.0 |
|  | SD | 0.0 | 0.5 | 0.1 |
|  | N | 8 | 12 | 20 |
| CD45-APC | Mean | 0.4 | 0.3 | 1.0 |
|  | SD | 0.2 | 0.2 | 2.9 |
|  | N | 8 | 12 | 19 |
| CD34-APC | Mean | 0.6 | 1.0 | 1.6 |
|  | SD | 0.4 | 0.6 | 1.8 |
|  | N | 8 | 12 | 22 |
| CD3-PE | Mean | 0.2 | 0.1 | 0.2 |
|  | SD | 0.1 | 0.1 | 0.1 |
|  | N | 6 | 10 | 17 |
| HLA-DR-PE | Mean | 0.7 | 1.0 | 1.8 |
|  | SD | 1.2 | 0.6 | 2.0 |
|  | N | 8 | 12 | 22 |
| HLA-DR/DP/DQ-FITC | Mean | 1.0 | 1.6 | 1.6 |
|  | SD | 0.4 | 1.1 | 1.1 |
|  | N | 8 | 12 | 22 |

TABLE 3-continued

Cell surface marker expression profile of MSC and MSC-derived bone-forming cell populations

| Marker expression (in %) | Statistics | MSCs | Bone-forming cells A | Bone-forming cells B |
|---|---|---|---|---|
| ALP-PE | Mean | 40.7 | 88.7 | 94.8 |
|  | SD | ND | 5.6 | 6.6 |
|  | N | 1 | 5 | 10 |
| CD49e-PE | Mean | 92.7 | 99.6 | 99.8 |
|  | SD | 20.5 | 1.1 | 0.5 |
|  | N | 8 | 12 | 19 |
| CD44-PE | Mean | 99.9 | 99.7 | 100.0 |
|  | SD | 0.2 | 0.5 | 0.0 |
|  | N | 8 | 12 | 22 |
| CD10 | Mean | 19.6 | 99.6 | 98.8 |
|  | Std Dev | 14 | 0.4 | 1.5 |
|  | N | 10 | 12 | 25 |

Abbreviations: ALP: alkaline phosphatase; APC: allophycocyanin; FITC: fluorescein isothiocyanate; HLA-DR: human leukocyte antigen - DR isotype; HLA-DR/DP/DQ: Human Leukocyte Antigen DR/DP/DQ isotypes; MSC: mesenchymal stem cells; ND: not determined; PE: phycoerythrin; SD: standard deviation

TABLE 4

ALP expression levels of MSC and MSC-derived bone-forming cell population assessed by different methods

|  | Statistics | MSCs | Bone-forming cells A | Bone-forming cells B |
|---|---|---|---|---|
| ALP-PE population positivity (%) | Mean | 40.7 | 88.7 | 94.8 |
|  | SD | ND | 5.6 | 6.6 |
|  | N | 1 | 5 | 10 |
| ALP-PE cell surface expression level (nMFI) | Mean | 2.4 | 19.8 | 56.1 |
|  | SD | ND | 10.8 | 27.4 |
|  | N | 1 | 5 | 10 |
| ALP enzymatic activity (mU/mg of total protein) | Mean | 176.3 | 671.9 | 874.7 |
|  | SD | 252.9 | 305.8 | 772.9 |
|  | N | 3 | 9 | 26 |

Abbreviations: ALP: alkaline phosphatase; MSC: mesenchymal stem cells; ND: not determined, nMFI: normalized median of fluorescence intensity; PE: phycoerythrin; SD: standard deviation

TABLE 5

Comparisons of the expression of the immunogenicity HLA-DR surface marker (FACS) on MSC-derived bone-forming cells using different culture conditions

| Cell population | HLA-DR (%) mean ± SD |
|---|---|
| Bone-forming cells Z generated with FGF2 | 63 ± 20 (N = 10) |
| Bone-forming cells A generated with FGF-2 and TGFβ1 | 6 ± 6 (N = 22) |
| Bone-forming cells B generated with FGF-2, TGFβ1 and heparin | 3 ± 2 (N = 8) |
| Bone-forming cells A generated with FGF-2 and TGFβ1 | 1.0 ± 0.6 (N = 12) |
| Bone-forming cells B generated with FGF-2, TGFβ1 and heparin | 1.8 ± 2.0 (N = 22) |

Abbreviations: FGF-2: fibroblast growth factor 2; HLA-DR: human leukocyte antigen - antigen D related; MSC: mesenchymal stem cells; SD: standard deviation; TGFβ1: transforming growth factor beta 1

TABLE 6

ALP expression levels of MSC and bone-forming cell populations generated in different culture conditions.

| Cell population | % of ALP$^+$ cells (flow cytometry) | % of ALP intra$^+$ cells (flow cytometry) | ALP enz. (mIU/mg total protein) | ALP staining |
|---|---|---|---|---|
| MSCs (control) | 20 ± 7 (N = 13) | 19 ± 13 (N = 11) | 108 ± 86 (N = 2) | NA |
| Bone-forming cell Z generated with FGF2 | 70 ± 19 (N = 17) | 63 ± 22 (N = 10) | 877 ± 680 (N = 6) | 1.8 ± 0.4 (N = 23) |
| Bone-forming cells A generated with FGF-2 and TGFβ1 | 69 ± 18 (N = 16) | 59 ± 22 (N = 10) | 495 ± 466 (N = 17) | 1.2 ± 0.4 (N = 13) |
| Bone-forming cells B generated with FGF-2, TGFβ1 and heparin | 91 ± 8 (N = 10) | 80 ± 13 (N = 8) | 1,016 ± 685 (N = 14) | 2.0 ± 0.0 (N = 22) |

Abbreviations: ALP: alkaline phosphatase; FGF-2: fibroblast growth factor 2; MSC: mesenchymal stem cells; NA: not available; TGFβ1: transforming growth factor beta 1

The cell surface marker expression profile was not only characterized by the presence of markers on cell surface (population positivity percentage) but also by analysing the quantity of markers expressed on cell surface (population normalized median of fluorescence) of different markers. These analyses highlighted some differences between the different MSC-derived bone-forming cells.

Bone-forming cells B cultured in presence of heparin expressed higher level of ALP than MSCs and bone-forming cells A cultured in absence of heparin (Table 7,ALP-PE nMFI results) confirming the commitment toward the osteoblastic lineage of bone-forming cells.

The expression of the mesenchymal markers CD73 and CD105 on cell surface are also dependent on the cell types. Bone-forming cells generated in presence of heparin (bone-forming cells B) expressed higher level of CD73 and CD105 than bone forming cells A (Table 7).

TABLE 7

Additional cell surface marker expression results of MSC and MSC-derived bone-forming cell populations

| Marker expression (in nMFI) | Statistics | MSCs | Bone-forming cells A | Bone-forming cells B |
|---|---|---|---|---|
| ALP-PE | Mean | 2.4 | 19.8 | 56.1 |
|  | SD | — | 10.8 | 27.4 |
|  | N | 1 | 5 | 10 |
| CD73-APC | Mean | 234.8 | 130.7 | 646.3 |
|  | SD | 84.3 | 80.1 | 138.8 |
|  | N | 6 | 11 | 22 |
| CD105-APC | Mean | 207.7 | 26.6 | 59.1 |
|  | SD | 67.6 | 15.2 | 13.1 |
|  | N | 8 | 12 | 20 |
| CD44-PE | Mean | 139.8 | 62.0 | 156.6 |
|  | SD | 57.5 | 19.1 | 40.7 |
|  | N | 8 | 12 | 22 |
| CD49e-PE | Mean | 81.0 | 22.5 | 33.5 |
|  | SD | 51.4 | 9.9 | 11.0 |
|  | N | 8 | 12 | 19 |
| HLA-ABC-FITC | Mean | 26.1 | 21.6 | 80.2 |
|  | SD | — | 5.2 | 17.4 |
|  | N | 1 | 4 | 8 |
| CD10-PE | Mean | 0.8 | 36.2 | 32.2 |
|  | SD | 1.1 | 16.4 | 16.8 |
|  | N | 8 | 12 | 22 |

Abbreviations: ALP: alkaline phosphatase; APC: Allophycocyanin; FGF-2: fibroblast growth factor 2; FITC: Fluorescein isothiocyanate; HLA-ABC: Human Leukocyte Antigen ABC; MSC: mesenchymal stem cells; NA: not available; ND: not determined; PE: phycoerythrin; SD: standard deviation; TGFβ1: transforming growth factor beta 1

2.2 RT-gPCR and Multiplex Assay

The analysis revealed that, genes RUNX2, SOX9, ZNF521, ALPL, BMP2, OPG, POSTN, CHI3L1, MMP13, CADM1, CX43, CD10, WISP1 encoding osteochondroblastic markers, and genes DCN, SPON1 encoding bone and cartilage matrix proteins were significantly overexpressed in bone-forming cells A and B as compared to MSCs (Table 8). Consistently, the gene expression of DKK1 encoding an osteochondrogenesis inhibitor was significantly down-regulated in bone-forming cells A and B compared to MSCs (Table 8).

The expression of genes K167 and PCNA encoding proliferation markers were significantly down-regulated in both bone-forming cells A and B compared to MSCs, and the gene expression of apoptosis-related markers BCL2 and BAX was equivalent in all cell types (Table 8).

When compared to bone forming cells A, the bone-forming cells B (statistical significance graphically represented depending on the p-value (p) obtained: * for p<0.05,  for p<0.01 and * for p<0.001):
- expressed higher levels of gene PPARG (***) (encoding a protein involved in the adipogenesis);
- expressed higher levels of genes CD73 (*), BMP2 (*) (encoding osteochondroblastic proteins);
- expressed lower levels of genes COL1A1 (*), BGN (*), SPARC (***), ALPL (*), BCL2 (***) (encoding osteochondroblastic proteins).

Regarding the genes which were overexpressed in bone-forming cells B compared to bone-forming cells A, PPARG, MMP13, BMP2 were also significantly over expressed in bone-forming cells B compared to MSCs, while CD73 had the same expression level in Bone-forming cells B and in MSC.

Regarding the genes that were downregulated in bone-forming cells B compared to bone-forming cells A (i.e., COL1A1, BGN, SPARC, BCL2), all of them had the same expression level in bone-forming cells B than in MSC except ALPL that was still overexpressed in bone-forming cells B compared to MSC.

TABLE 8

Gene expression profile of MSC and MSC-derived bone-forming cell populations (expressed in fold change relative to mean MSCs values - statistical significance is graphically represented depending on the p-value (p) obtained; * for p < 0.05;  for p < 0.01; * for p < 0.001; NS: not statistically significant)

| | Gene expression (fold change relative to mean MSC values) | Statistics | MSCs | Bone-forming cells A | Bone-forming cells B |
|---|---|---|---|---|---|
| Mesenchymal markers | CD73 | Mean | 1.00 | 0.36** | 1.12 (NS) |
| | | SD | NA | 0.01 | 0.24 |
| | | N | 1 | 3 | 6 |
| | CD105 | Mean | 1.00 | 0.55 (NS) | 0.48* |
| | | SD | NA | 0.10 | 0.12 |
| | | N | 1 | 3 | 6 |
| Differentiation master genes | RUNX2 | Mean | 1.04 | 1.47*** | 1.64*** |
| | | SD | 0.27 | 0.27 | 0.43 |
| | | N | 7 | 9 | 29 |
| | SOX9 | Mean | 1.16 | 2.95*** | 2.03** |
| | | SD | 0.73 | 1.42 | 0.87 |
| | | N | 7 | 9 | 29 |
| | PPARG | Mean | 1.17 | 6.93*** | 3.05*** |
| | | SD | 0.75 | 2.16 | 1.83 |
| | | N | 7 | 9 | 29 |
| | ZNF521 | Mean | 1.45 | 49.85*** | 63.88*** |
| | | SD | 1.18 | 29.10 | 23.11 |
| | | N | 7 | 9 | 29 |

TABLE 8-continued

Gene expression profile of MSC and MSC-derived bone-forming cell populations (expressed in fold change relative to mean MSCs values - statistical significance is graphically represented depending on the p-value (p) obtained; * for p < 0.05;  for p < 0.01; * for p < 0.001; NS: not statistically significant)

| | Gene expression (fold change relative to mean MSC values) | Statistics | MSCs | Bone-forming cells A | Bone-forming cells B |
|---|---|---|---|---|---|
| | DKK1 | Mean | 1.00 | 0.02*** | 0.01*** |
| | | SD | NA | 0.01 | 0.01 |
| | | N | 1 | 3 | 6 |
| Extracellular matrix-related markers | SPON1 | Mean | 1.09 | 576.25*** | 539.25*** |
| | | SD | 0.45 | 397.77 | 339.77 |
| | | N | 6 | 9 | 29 |
| | COL1A1 | Mean | 1.03 | 2.09*** | 0.88 (NS) |
| | | SD | 0.27 | 0.41 | 0.41 |
| | | N | 7 | 9 | 29 |
| | BGN | Mean | 1.00 | 2.18*** | 1.26 (NS) |
| | | SD | 0.05 | 0.37 | 0.36 |
| | | N | 7 | 9 | 29 |
| | DCN | Mean | 1.08 | 9.80*** | 7.31*** |
| | | SD | 0.42 | 3.30 | 3.22 |
| | | N | 6 | 9 | 29 |
| | SPARC | Mean | 1.01 | 2.21*** | 0.91 (NS) |
| | | SD | 0.15 | 0.59 | 0.33 |
| | | N | 7 | 9 | 29 |
| | IBSP | Mean | 1.11 | 8.24 (NS) | 14.34** |
| | | SD | 0.46 | 11.29 | 15.38 |
| | | N | 7 | 9 | 28 |
| | OCN | Mean | 1.02 | 1.29 (NS) | 1.50** |
| | | SD | 0.22 | 0.33 | 0.58 |
| | | N | 7 | 9 | 29 |
| Osteochondrogenic markers | ALPL | Mean | 1.49 | 13.83*** | 8.91*** |
| | | SD | 1.61 | 5.98 | 6.73 |
| | | N | 7 | 9 | 29 |
| | MMP13 | Mean | 1.32 | 216.27*** | 2739.98*** |
| | | SD | 1.26 | 254.24 | 2886.30 |
| | | N | 7 | 9 | 29 |
| | CX43 | Mean | 1.06 | 3.20*** | 2.74*** |
| | | SD | 0.38 | 0.98 | 0.96 |
| | | N | 7 | 9 | 29 |
| | OPN | Mean | 1.70 | 6.32 (NS) | 4.47 (NS) |
| | | SD | 1.71 | 6.60 | 11.23 |
| | | N | 7 | 9 | 29 |
| | OPG | Mean | 1.12 | 2.79* | 1.48 (NS) |
| | | SD | 0.53 | 2.43 | 0.78 |
| | | N | 7 | 9 | 29 |
| | BMP2 | Mean | 1.04 | 10.76*** | 32.69*** |
| | | SD | 0.29 | 6.19 | 25.88 |
| | | N | 7 | 9 | 29 |
| | POSTN | Mean | 1.14 | 5.70*** | 3.70*** |
| | | SD | 0.71 | 1.42 | 1.81 |
| | | N | 7 | 9 | 29 |
| | WISP1 | Mean | 1.11 | 3.16*** | 2.13** |
| | | SD | 0.53 | 1.21 | 0.92 |
| | | N | 7 | 9 | 29 |
| | CADM1 | Mean | 1.70 | 43.28*** | 19.55*** |
| | | SD | 1.87 | 27.53 | 22.12 |
| | | N | 7 | 9 | 29 |
| | CHI3L1 | Mean | 1.84 | 430.19*** | 775.23*** |
| | | SD | 2.21 | 309.05 | 462.38 |
| | | N | 7 | 9 | 29 |
| | CD10 | Mean | 1.00 | 62.65*** | 57.96*** |
| | | SD | NA | 14.43 | 30.91 |
| | | N | 1 | 3 | 6 |
| Proliferation markers | KI67 | Mean | 1.27 | 0.13*** | 0.14*** |
| | | SD | 1.13 | 0.26 | 0.13 |
| | | N | 7 | 9 | 29 |
| | PCNA | Mean | 1.09 | 0.63** | 0.62*** |
| | | SD | 0.50 | 0.06 | 0.23 |
| | | N | 7 | 9 | 29 |

TABLE 8-continued

Gene expression profile of MSC and MSC-derived bone-forming cell populations (expressed in fold change relative to mean MSCs values - statistical significance is graphically represented depending on the p-value (p) obtained; * for p < 0.05;  for p < 0.01; * for p < 0.001; NS: not statistically significant)

| Gene expression (fold change relative to mean MSC values) | | Statistics | MSCs | Bone-forming cells A | Bone-forming cells B |
|---|---|---|---|---|---|
| Apoptotis-associated markers | BCL2 | Mean | 1.08 | 3.43*** | 0.97 (NS) |
| | | SD | 0.46 | 0.97 | 0.46 |
| | | N | 7 | 8 | 29 |
| | BAX | Mean | 1.01 | 1.65* | 1.92** |
| | | SD | 0.15 | 0.18 | 2.43 |
| | | N | 7 | 9 | 29 |

Cell secretion analysis showed that bone-forming cells B secreted higher amounts of proteins CHI3L1 and MMP13 involved in osteochondrogenesis, than bone-forming cells A and MSCs (Table 9) and secreted lower amount of DKK1 involved in the inhibition of osteogenesis, than bone-forming cells A and MSC. No significant difference was observed among cell types for the quantity of secreted COL1A1 (Table 9).

TABLE 9

Secretion profile of MSC and MSC-derived bone-forming cell populations (expressed in fold change relative to mean MSCs values- statistical significance is graphically represented depending on the p-value (p) obtained; * for p < 0.05;  for p < 0.01; * for p < 0.001; NS: not statistically significant)

| Protein secretion (pg/ml) | Statistics | MSCs | Bone-forming cells A | Bone-forming cells B |
|---|---|---|---|---|
| COL1A1 | Mean | 57347 | 79822 (NS) | 79216 (NS) |
| | SD | 32288 | 48969 | 41636 |
| | N | 5 | 6 | 11 |
| CHI3L1 | Mean | 64533 | 123800 (NS) | 303436** |
| | SD | 32242 | 70909 | 232874 |
| | N | 5 | 6 | 11 |
| DKK1 | Mean | 3679 | 4979 (NS) | 1609*** |
| | SD | 1287 | 1913 | 850 |
| | N | 5 | 6 | 11 |
| MMP13 | Mean | 180 | 294 | 693*** |
| | SD | 54 | 80 (NS) | 545 |
| | N | 5 | 6 | 11 |

2.3 Cell Size

Figure 1B:
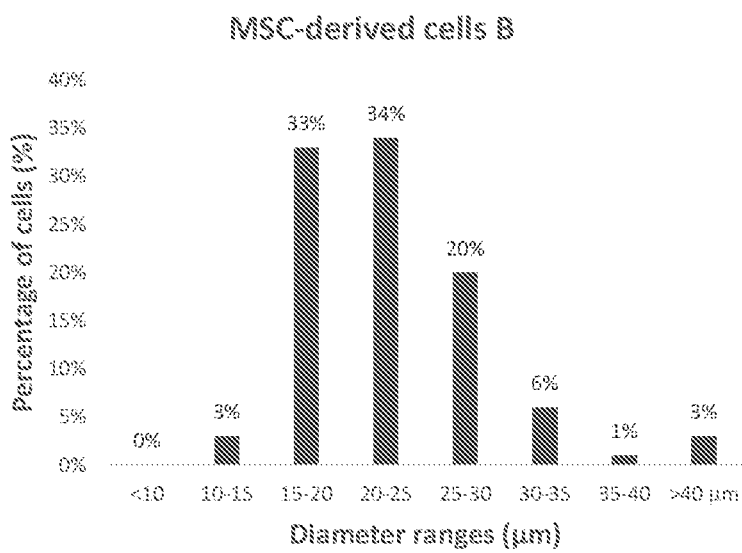
Figure 11A:
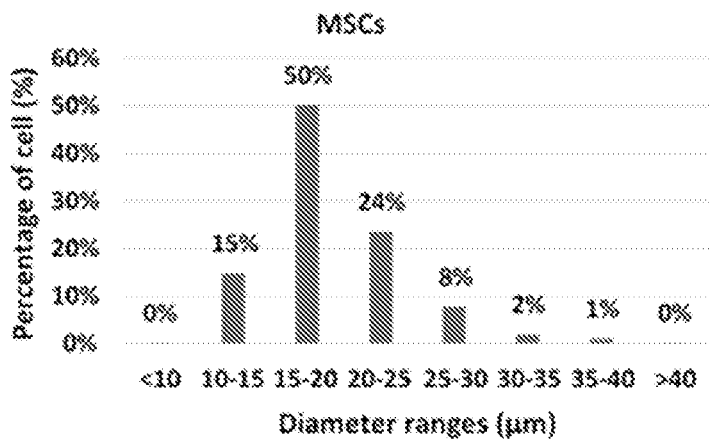
FIG. 11 illustrates the cell size of (A) MSCs, (B) MSC-derived bone-forming cells A (generated with FGF-2 and TGFβ1), and (C) MSC-derived bone-forming cells B (generated with FGF-2, TGFβ1 and heparin).
Figure 11B:
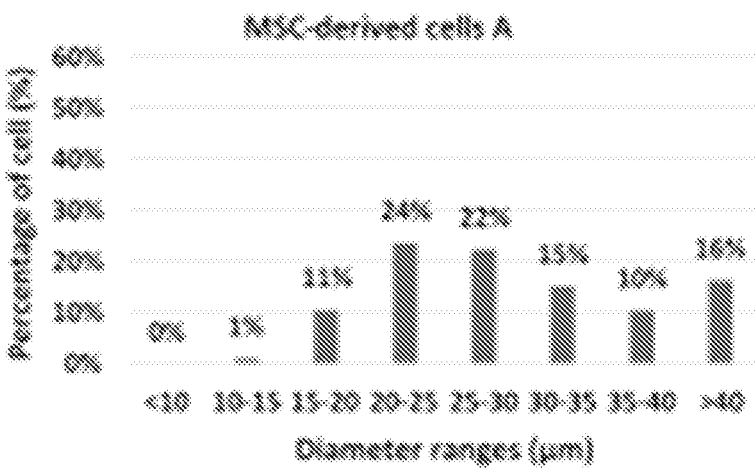
Figure 11C:
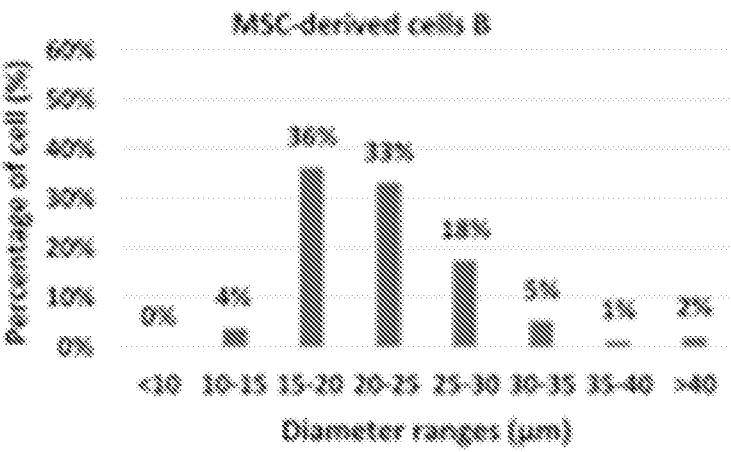

The cell size measurements using (i) Motic Image Plus 2.0/3.0 software and (ii) flow cytometry FSC analysis confirmed that the MSC-derived bone-forming cells generated with FGF-2, TGFβ1 and heparin (bone-forming cells B) are smaller and more homogeneous than MSC-derived bone-forming cells generated with FGF-2 and TGFβ1—without heparin (e.g., bone-forming cells A) (Tables 10 and 11, FIGS. 1 and 11).

Very interestingly, the large majority of bone-forming cells B (70%) does not exceed 25 μm diameter and ≤5% of them exceed 35 μm diameter (Tables 8 and 9). In contrast, the bone-forming cell population obtained without heparin supply (bone-forming cells A) includes only 20% of cells which do not exceed 25 μm diameter and 41% of cells with a diameter higher than 35 μm (FIG. 1 and Table 10). As detailed further in Example 3, such large diameter cells could prove detrimental upon the subject implantation.

TABLE 10

Distribution of cell sizes of bone-forming cells A and B

| Cell % with a diameter | ≤25 μm | >35 μm |
|---|---|---|
| Bone-forming cells A generated with FGF-2 and TGFβ-1 | 20% | 41% |
| Bone-forming cells B generated with FGF-2, TGFβ-1 and heparin | 70% | 5% |

Abbreviations: FGF-2: fibroblast growth factor 2; TGFβ1: transforming growth factor beta 1

TABLE 11

Distribution of cell size of MSCs and MSC-derived bone-forming cells

| Cell % with a diameter | ≤25 μm | >35 μm |
|---|---|---|
| MSCs | 89.9% | 1.3% |
| Bone-forming cells A | 35.4% | 26.9% |
| Bone-forming cells B | 73.7% | 3.3% |

Abbreviations: MSC: mesenchymal stem cells

TABLE 12

Diameter of MSC and MSC-derived bone-forming cells

| Cell diameter (μm) | Mean ± SD (N) | Min-max |
|---|---|---|
| MSC (control) | 22.4 ± 4.9 (N = 101) | 13.6-38.0 |
| Bone-forming cells A generated with FGF-2 and TGFβ1 | 34.1 ± 9.9 (N = 699) | 15.9-67 |
| Bone-forming cells B generated with FGF-2, TGFβ1 and heparin | 23.3 ± 6.8 (N = 1170) | 12.1-74.5 |
| Ratio (Bone-forming cells B/ Bone-forming cells A) | 0.68 | |

Abbreviations: FGF-2: fibroblast growth factor 2; MSC: mesenchymal stem cells; SD: standard deviation; TGFβ1: transforming growth factor beta 1

TABLE 13

Diameter of MSCs and MSC-derived bone-forming cells

| Cell diameter (μm) | Mean ± SD | Min-max | N |
|---|---|---|---|
| MSCs | 19.2 ± 4.8 | 9.8-41.8 | 450 |
| Bone-forming cells A | 30.2 ± 9.9 | 11.4-67 | 1205 |
| Bone-forming cells B | 22.4 ± 6.4 | 7.9-74.5 | 1744 |

Abbreviations: MSC: mesenchymal stem cells; SD: standard deviation

Flow cytometry FSC experiments were used to assess the relative mean cell size of bone-forming cells B generated with FGF-2, TGFβ1 and heparin at different time points over the in vitro culture, and therefore at different cell confluences, namely 45%, 70%, 90% and 100% confluency. Table 14 shows that the cell size of bone-forming cells B is stable and eventually increases with the cell culture confluence. In other words, Table 14 shows that the mean size of bone-forming cells B from a more confluent cell flask is higher than that from a less confluent culture flask. It should be noted that flow cytometry FSC experiments allow to compare the mean cell size of different sample without however giving information on the absolute values of the mean cell size.

TABLE 14

Flow cytometry FSC value of bone-forming
cells B harvested at different time
points and confluence during in vitro culture

| Total duration of cell culture | Confluence | Relative mean fluorescence unit |
|---|---|---|
| D21 | 45% | 69.307 |
| D23 | 70% | 65.228 |
| D26 | 90% | 77.349 |
| D28 | 100% | 91.124 |

Example 2: Specificity of the Method for Preparing MSC-Derived Cells of Example 1

1. Experimental Procedures
1.1 Cell Culture and Plasma Preparation

Cell culture and plasma preparation were performed as described in Example 1.

For the experiments relating to the comparison between heparin and analogues thereof, the conventional culture medium was supplemented with (i) 5% v/v S/D plasma; (ii) basic FGF-2; (iii) TGFβ1; and (iv) 0.1 IU/ml of unfractionated heparin (UFH), dalteparin, heparan sulfate, or danaparoid.

For the experiments relating to the comparison between heparin and other anticoagulants, the conventional culture medium was supplemented with (i) 5% v/v S/D plasma; (ii) basic FGF-2; (iii) TGFβ; and (iv) 1 IU/ml heparin (Heparin LEO, LEO Pharma SA, Belgium, lot A17605), 100 IU/ml heparin, 2 mg/ml of ethylenediaminetetraacetic acid (EDTA) or 0.1 mg/ml Actilyse®.

For the experiments relating to the comparison between S/D plasma and serum, the conventional culture medium was supplemented with (i) 5% v/v S/D plasma or 5% serum; (ii) basic FGF-2; (iii) TGFβ; and (iv) 0.1 IU/ml of heparin.

For the experiments relating to the comparison between the presence or absence of S/D plasma or serum, the conventional culture medium was supplemented with (i) 5% v/v S/D plasma, 5% v/v serum, or 0% S/D plasma and 0% serum; (ii) basic FGF-2; (iii) TGFβ; and (iv) 0.1 IU/ml of heparin.

2. Results
2.1 Heparin Vs. Analogues Thereof

Figure 2:
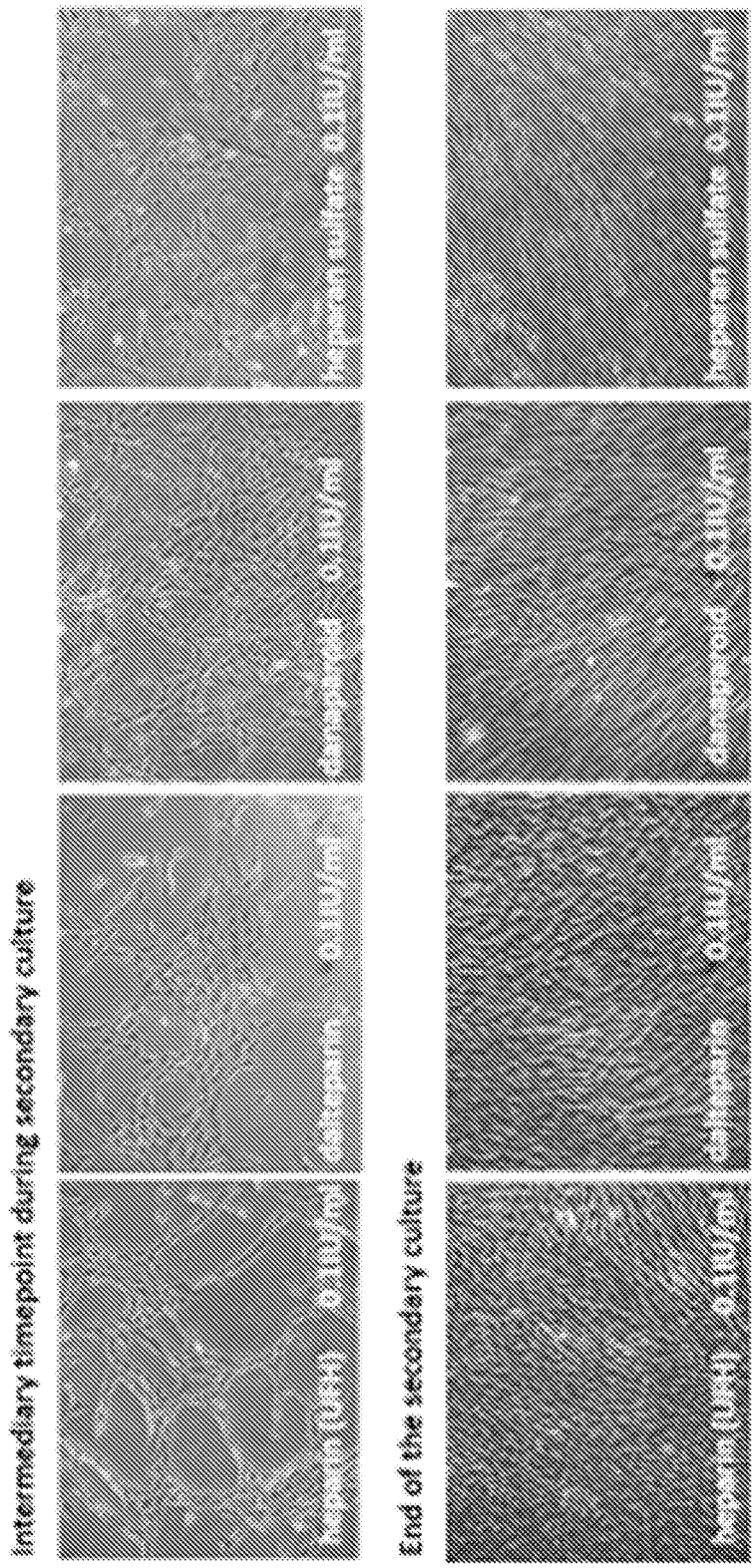
FIG. 2 illustrates the generation of MSC-derived cells, particularly MSC-derived bone-forming cells, with different heparinoids: unfractionated heparin (UFH), dalteparin, danaparoid and heparan sulfate; used at 0.1 IU/ml.

FIG. 2 and Table 15 show that the heparin present in the culture medium can be substituted by derivatives thereof (heparinoid compounds), namely by dalteparin, heparan sulfate, or glycosaminoglycans mixture such as danaparoid which includes heparan sulfate. The 4 heparin derivatives have the same effects on cell viability and marker expression profile as heparin (Table 15).

TABLE 15

Generated MSC-derived bone-forming cells using different heparinoids:
UFH, dalteparin, danaparoid and heparan sulfate; used at 0.1 IU/ml.

| | Viability | MSC | | Hematopoietic | | | Immuno | | | Osteo |
|---|---|---|---|---|---|---|---|---|---|---|
| | | CD73 | CD90 | CD3 | CD34 | CD45 | HLA-DR | CD40 | CD86 | ALP |
| Heparin | 97 ± 2 | 99 ± 1 | 98 ± 1 | 0 ± 1 | 1 ± 1 | 4 ± 3 | 2 ± 1 | 0 ± 1 | 2 ± 2 | 88 ± 16 |
| | (N = 4) | (N = 4) | (N = 4) | (N = 4) | (N = 4) | (N = 4) | (N = 3) | (N = 4) | (N = 4) | (N = 4) |
| Dalteparin | 98 ± 2 | 98 ± 1 | 98 ± 1 | 0 ± 1 | 0 ± 1 | 4 ± 4 | 3 ± 3 | 0 ± 1 | 1 ± 2 | 94 ± 3 |
| | (N = 3) | (N = 3) | (N = 3) | (N = 3) | (N = 3) | (N = 3) | (N = 3) | (N = 3) | (N = 3) | (N = 3) |
| Danaparoid | 97 ± 2 | 99 ± 1 | 98 ± 1 | 0 ± 1 | 2 ± 3 | 5 ± 4 | 4 ± 2 | 0 ± 1 | 3 ± 2 | 89 ± 15 |
| | (N = 4) | (N = 4) | (N = 4) | (N = 4) | (N = 4) | (N = 4) | (N = 3) | (N = 4) | (N = 4) | (N = 4) |
| Heparan sulfate | 97 ± 2 | 99 ± 1 | 99 ± 1 | 2 ± 3 | 1 ± 1 | 4 ± 1 | 4 ± 2 | 1 ± 2 | 4 ± 4 | 92 ± 11 |
| | (N = 4) | (N = 4) | (N = 4) | (N = 4) | (N = 4) | (N = 4) | (N = 3) | (N = 4) | (N = 4) | (N = 4) |

| | Adhesion | | | | | | | | |
|---|---|---|---|---|---|---|---|---|---|
| | CD29 | CD44 | CD49a | CD49b | CD49d | CD49e | CD51/CD61 | CD54 | CD166 |
| Heparin | 99 ± 1 | 98 ± 1 | 25 ± 6 | 53 ± 7 | 79 ± 3 | 97 ± 4 | 50 ± 23 | 70 ± 19 | 97 ± 3 |
| | (N = 4) | (N = 4) | (N = 4) | (N = 4) | (N = 4) | (N = 4) | (N = 4) | (N = 4) | (N = 4) |
| Dalteparin | 98 ± 1 | 98 ± 1 | 29 ± 14 | 61 ± 3 | 78 ± 15 | 98 ± 1 | 26 ± 19 | 65 ± 11 | 96 ± 1 |
| | (N = 3) | (N = 3) | (N = 3) | (N = 3) | (N = 3) | (N = 3) | (N = 3) | (N = 3) | (N = 3) |
| Danaparoid | 99 ± 1 | 99 ± 1 | 32 ± 9 | 69 ± 21 | 88 ± 6 | 98 ± 2 | 39 ± 23 | 74 ± 10 | 97 ± 3 |
| | (N = 4) | (N = 4) | (N = 4) | (N = 4) | (N = 4) | (N = 4) | (N = 4) | (N = 4) | (N = 4) |
| Heparan sulfate | 99 ± 1 | 98 ± 1 | 32 ± 8 | 75 ± 15 | 88 ± 3 | 98 ± 2 | 41 ± 18 | 79 ± 10 | 98 ± 2 |
| | (N = 4) | (N = 4) | (N = 4) | (N = 4) | (N = 4) | (N = 4) | (N = 4) | (N = 4) | (N = 4) |

2.2 Heparin Vs. Other Anticoagulants

Figure 3:
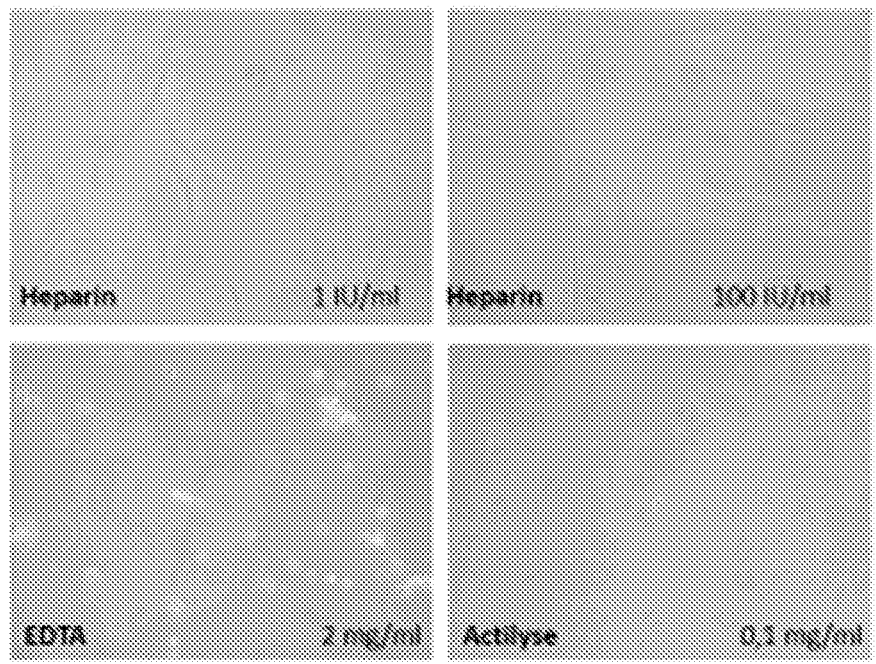
FIG. 3 illustrates a MSC culture with heparin vs. other anticoagulants: EDTA and Actilyse® (alteplase, recombinant tissue plasminogen activator). After 36 hrs of culture, cells contacted with EDTA at 2 mg/ml and Actilyse® at 0.1 mg/ml are in suspension while the cells contacted with heparin 1 or 100 IU/ml are growing and adherent.

FIG. 3 shows that heparin and derivative thereof (at a concentration of 1 IU/ml or 100 IU/ml) cannot be replaced by other anticoagulants such as EDTA 2 mg/ml (E8008, Sigma-Aldrich, lot RNBBB7793), Actilyse® 0.1 mg/ml (Boehringer Ingelheim, lot 001408)

2.3 Plasma Vs. Serum

Figure 4:
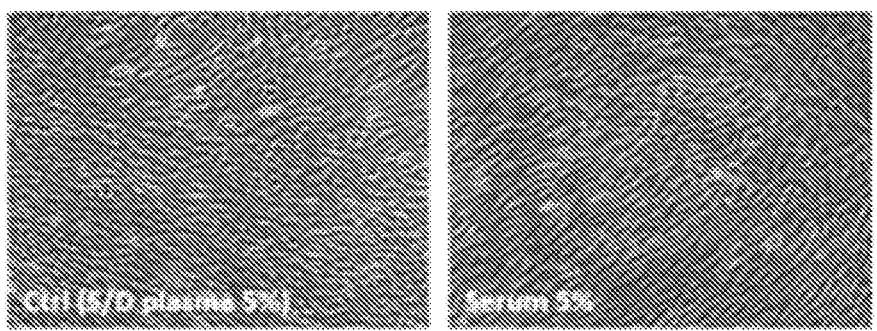
FIG. 4 illustrates MSC-derived cells, particularly MSC-derived bone-forming cells, cultured with an embodiment of the method of the invention where the solvent/detergent-treated (S/D) plasma (5% v/v) has been substituted by serum (5% v/v).

FIG. 4 shows that the S/D plasma can be replaced by serum to generate MSC-derived bone-forming cells according to the invention. In view hereof, it appears that heparin or analogues thereof are key elements in the method for preparing bone-forming cells B.

Example 3: In Vitro Mineralization Ability of MSC-Derived Cells B Obtained by the Method of Example 1

1. Experimental Procedures

The mineralization assay investigates the in vitro cells ability to generate a mineralized matrix by culturing them in osteogenic medium for several weeks. The mineralized matrix will afterwards be stained using an alizarin red S (ARS) staining.

Briefly, the MSC-derived bone-forming B obtained after secondary culture as described in Section 1.1 of Experiment 1 above were harvested and plated in a basic medium α-MEM (Lonza) supplemented with Penicillin-streptomycin (Lonza) and 5% of serum per well at 60,000 cells/cm$^2$ in a 48 well-plate until they reached confluence (1 to 2 days). Subsequently, medium was changed by an osteogenic medium comprising basic medium α-MEM (Lonza) supplemented with Penicillin-streptomycin (Lonza), 5% of serum, $10^{-8}$M dexamethasone (Sigma), 50 µg/ml ascorbic acid (Sigma) and 5 mM β-glycerophosphate (Sigma). Osteogenic medium was changed every 3±2 days by a freshly prepare osteogenic medium.

An ARS staining was performed at day 21 and day 28 after osteogenic induction, as follows: cells were washed with phosphate buffer saline, incubated with formaldehyde 4% at room temperature for 15 minutes, washed with phosphate buffered saline and subsequently washed with demineralized water. Cells were then exposed for 10 minutes at room temperature to an ARS solution (20 g/L) pH 4.2. Cells were washed with demineralized water until the washing solution was clear, and observed macroscopically and microscopically. Wells were placed under an inverted microscope (AE31; Motic). Images taken with a camera (Moticam) placed on the microscope were analysed in order to assess the orange-red staining of calcium deposited in the wells.

2. Results

Figure 5A:
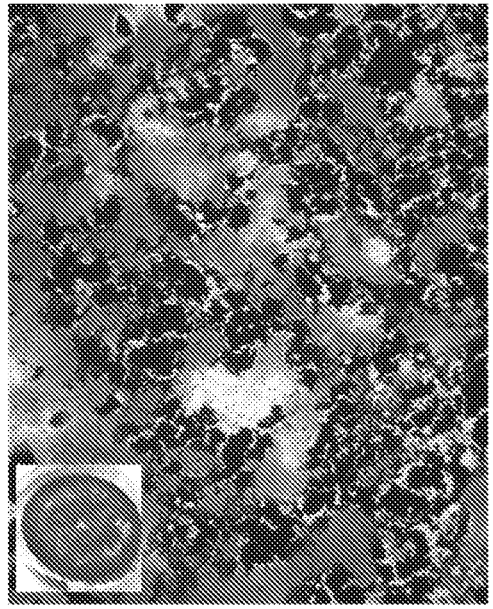
FIG. 5 illustrates in vitro mineralization of MSC-derived cells, assayed by alizarin red staining (ARS). MSC-derived bone-forming cells B (generated with FGF-2, TGFβ1 and heparin) were cultured under osteogenic conditions. An ARS was performed after 21 days (A) and 28 days (B) of culture under osteogenic conditions to stain calcium and phosphate deposites (100× magnification).
Figure 5B:
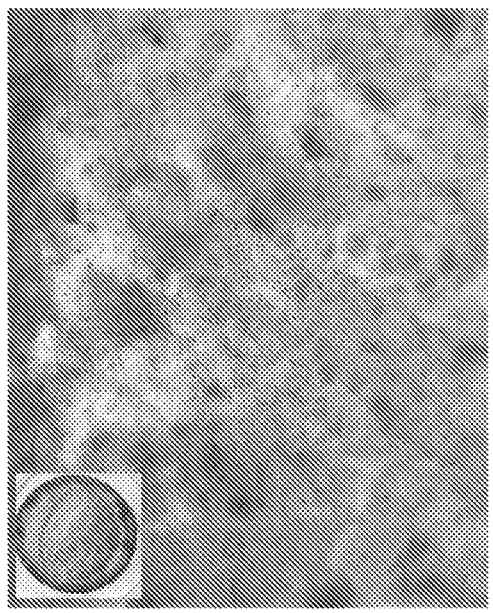

Macroscopic and microscopic observations reveal a positive ARS staining, with an increase in ARS staining from day 21 to day 28, consequently an increase of calcium/phosphate deposition overtime (FIG. 5). These results show that bone-forming cells B generated with FGF-2, TGFβ1 and heparin are able to synthesize bone matrix and mineralize it by deposition of calcium and phosphate. More particularly, these results show that bone-forming cells B display high osteogenic properties.

Example 4: In Vitro Chondrogenesis Ability of MSC-Derived Cells B Obtained by the Method of Example 1

1. Experimental Procedures

Under specific culture conditions, MSC-derived cells obtained by the method of Example 1 can undertake chondrocyte differentiation. These conditions include three-dimensional conformation of the cells in aggregates where high cell density and cell-cell interactions contribute to the mechanism of chondrogenesis. Briefly, the MSC-derived bone-forming cells B obtained after secondary culture as described in Section 1.1 of Example 1 above were harvested and re-suspended in chondrogenic differentiation medium and placed in 96-well plates (non-adherent conic bottom) at a density of 2.5×10$^5$ cells/well. The chondrogenic culture medium consists in Dulbecco's Modified Eagle's Medium (DMEM), High Glucose (4.5 g/1) (DMEM-HG, Lonza) supplemented with 10% human insulin, human transferrin, and sodium selenite (ITS) (ITS+1, Sigma-Aldrich), 1% sodium pyruvate (Lonza), $10^7$M dexamethasone (Sigma), 1 µM ascorbic acid (Sigma) and 10 ng/ml TGFβ1 (HumanZyme). The negative control item consisted in chondrogenic medium without soluble differentiation factors dexamethasone, ascorbic acid and TGFβ1. Multi-well plates were then centrifuged at 200×g for 5 min to form cell aggregates and were then placed at 37° C. in a humidified atmosphere of 95% air and 5% $CO_2$ for 3 weeks. Chondrogenic culture medium were changed each 2 or 3 days. Macroscopic observation 24 hours after aggregates formation showed that cell aggregates were freely floating in the culture media.

Three weeks after chondrogenesis induction, cell aggregates were collected and processed for histological analysis: the collected cell aggregates were fixed in 3.7% formaldehyde and embedded in paraffin wax. Paraffin blocks were cut into 5 µm sections. Sections were stained using (i) hematoxylin and eosin (H&E), (ii) toluidine blue and safranin-orange to stain proteoglycans and (iii) sirius red to stain collagen fibers. The method consisted in standard deparaffinization, staining, dehydration and mounting on a slide glass. Stained sections were qualitatively observed microscopically (cellularity, cells localization and aspect, extracellular matrix aspect and collagen and proteoglycan content).

2. Results

Microscopic observations and aggregate diameter measures indicated that cell aggregates cultured in chondrogenic medium displayed a higher size than cell aggregates cultured in control medium (data not shown). This size increases in chondrogenic medium could be associated with (1) the production and the accumulation of extracellular matrix by cells and/or (2) the cell proliferation in the aggregate.

Figure 6:
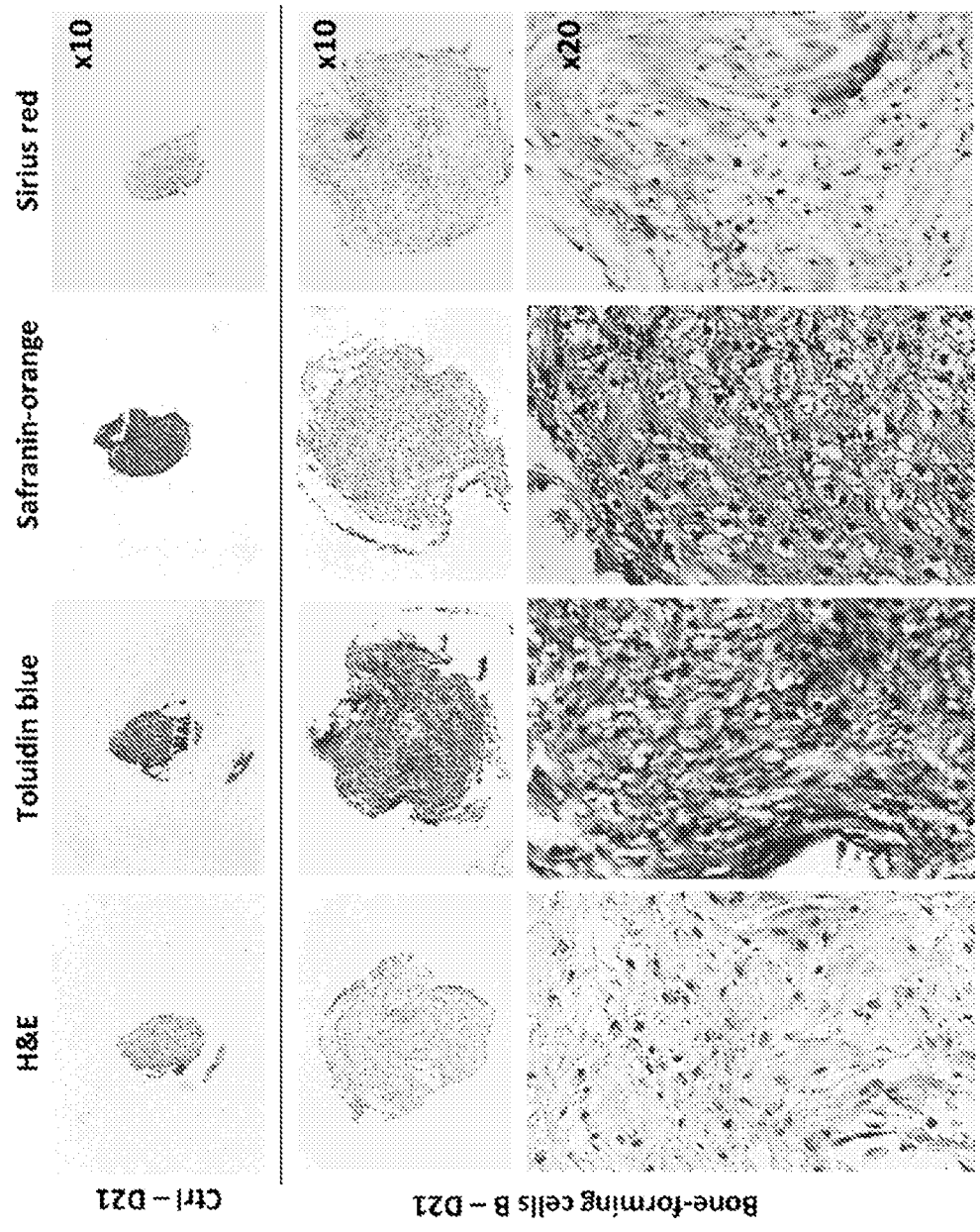
FIG. 6 illustrates hematoxylin and eosin staining and cartilaginous extracellular matrix (proteoglycans and collagen) staining of cell aggregates sections. MSC-derived bone-forming cells B (generated with FGF-2, TGFβ1 and heparin) were centrifuged to form cell aggregates, and the cell aggregates were cultured for 21 days under chondrogenic conditions or control conditions. Toluidine blue stains proteoglycan from the cartilaginous extracellular matrix and cell nuclei. Safranin-orange stains proteoglycan from the cartilaginous extracellular matrix, and sirius red stains collagen.

The qualitative observation of aggregate sections stained with hematoxylin and eosin showed differences in cell morphology between control and chondrogenic medium (H&E staining, FIG. 6). Indeed, in control medium "micronuclei" were observed and it was difficult to observe cell cytoplasm. Whereas in chondrogenic medium, two cell types could be observed, cells with flattened nucleus (at the periphery of the aggregates) and as one moves away from the periphery, cells with rounded nucleus. Chondrogenic differentiation was confirmed through the staining of proteoglycans and collagen of the cartilaginous extracellular matrix. In comparison, control aggregates show no positive staining for all tested stainings (toluidine blue, safranin-orange and sirius red staining, FIG. 6).

These results show that bone-forming cells B generated with FGF-2, TGFβ1 and heparin are able to produce abundant extracellular matrix composed primarily of cartilage-specific molecules such as collagen and proteoglycans, when cultured in a chondrogenic medium.

Example 5: In Vivo Safety of Bone-Forming Cells A and B Obtained by the Method of Example 1

1. Experimental Procedures
1.1 Cell Culture and Plasma Preparation

Cell culture and plasma preparation were performed as described in Example 1.

Before administration, bone-forming cells A and B were tested for viability, cell size, identity (including expression of surface antigens by flow cytometry analysis, ALP enzymatic activity and ALP staining assay) and sterility.

1.2 Mice Toxicity Study

Twelve weeks-old male and female NMRI-nude mice were injected intravenously with one of the following test items: (i) bone-forming cells A (5 million cells suspended in 200 µl of excipient), (ii) bone-forming cells A (5 million cells suspended in 200 µl of excipient) with heparin (Heparin LEO 100 UI/ml, LEO Pharma SA, lot A17605; 4 units) or (iii) bone-forming cells B (5 million cells suspended in 200 µl of excipient). Control item consisted in 200 µl of excipient (alone). Control and test items administration was performed as a slow bolus, by intravenous injection into lateral vein of the tail. The duration of the injection was at least 60 seconds. The quantity of cells and the volume administered per animal were constant.

The animals were observed for up to 6 months period, and several following parameters were monitored and/or assessed during the follow-up, amongst others: mortality and morbidity, animal body weight, clinical observations/physical examination, hematological and chemical blood analysis, and organs collection for histopathological analysis after animal euthanaia.

1.3. Histopathological Analysis

Mice lungs were collected for histopathological analysis. The collected mice lungs were processed for a histopathological analysis: samples were dehydrated and embedded in paraffin wax. Sections were cut 3-5 µm thick (transversal sections) and stained for hematoxilin and eosin. The slides were submitted to a senior pathologist to determine the cause(s) of acute mortality.

2. Results 2.1 Acute Toxicity

A toxicity study was conducted to evaluate the possible adverse effects of the intravenous injection of bone-forming cells A (generated with FGF-2 and TGFβ1) and small-sized bone-forming cells B (generated with FGF-2, TGFβ1 and heparin) in mice.

As presented in Table 16, acute mortality (10-35%) was observed after intravenous administration of bone-forming cells A (A-1 and A-2), and the addition of anticoagulant heparin (4 units) in the cell suspension did not reduce such mortality (A-3 to A-5 with heparin). In contrast, no acute toxicity was observed after intravenous administration of control item (excipient) and of small-size bone-forming cells B (B-1 to B-4).

TABLE 16

Cell size profile of bone-forming cells A and B and acute toxicity observed following intravenous injection in mice

| Batch of bone-forming cells | Mean (µm) | Max (µm) | Min (µm) | Cells number >30 µm | Acute toxicity |
|---|---|---|---|---|---|
| A-1 | ND | ND | ND | ND | 10% (4/40) |
| A-2 | ND | ND | ND | ND | 35% (14/40) |
| A-3 + heparin | 21.7 | 34.9 | 14.1 | 1 cell/20 | 0% (0/20) |
| A-4 + heparin | 38.2 | 57.6 | 18.6 | 17 cells/20 | 21% (4/19) |
| A-5 + heparin | 26.8 | 53.6 | 53.6 | 5 cells/28 | 75% (3/4*) |
| B-1 | 17.5 | 29.5 | 11.6 | None | 0% (0/19) |
| B-2 | 21.5 | 30.8 | 16.9 | 1 cell/20 | 0% (0/20) |
| B-3 | 14.3 | 21.2 | 8.7 | None | 0% (0/18) |
| B-4 | 17.7 | 25.0 | 13.3 | None | 0% (0/17) |

Figure 7A:
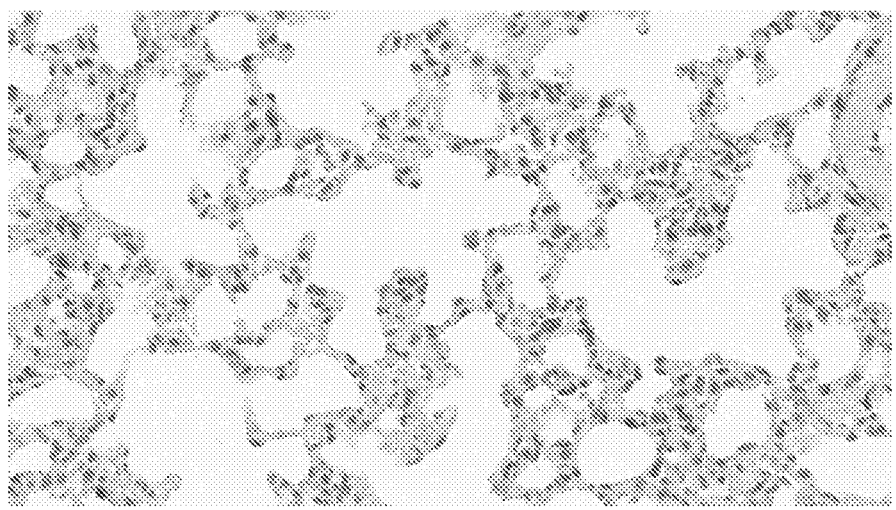
FIG. 7 illustrates the hematoxylin and eosin staining of lung parenchyma histological sections (200× magnification). (A) Animal injected with MSC-derived bone-forming cells B: normal lung parenchyma; (B) Animal injected with bone-forming cells A: lung parenchyma with disseminated numerous groups of injected cells in alveolar capillaries (arrows).
Figure 7B:
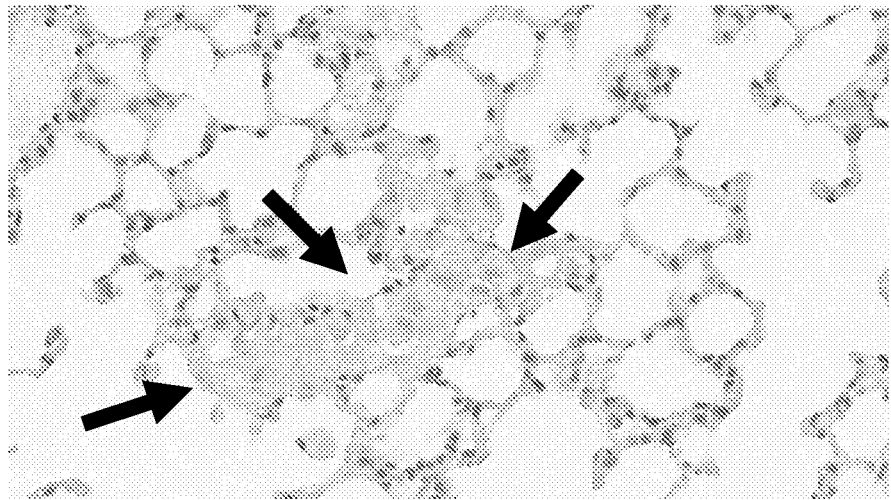

*Injections were stopped after 3 animals died (out of the 15 planned).
ND: not determined 2.2 Histopathological Examination After euthanasia, a necropsy was performed on all animals. Mice injected with small-sized bone-forming cells B presented overall normal lung architecture, with no cellular embolization of alveolar and bronchiolar capillaries observed (FIG. 7A). Mice injected with bone-forming cells A presented lung lesions characterized by moderate to severe disseminated embolization of alveolar and bronchiolar capillaries by a high number of middle size cells (interpreted as injected cells) often accompanied by an acute interstitial inflammation (FIG. 7B): 30% to 50% of alveolar capillaries and small to middle size bronchiolar arterioles were randomly enlarged by groups of cells which occlude the totality of the vascular lumen. Larger groups of occluded capillaries compressed bronchioles in their vicinity and were surrounded by alveolar collapse. Intra-alveolar and intra-bronchiolar microhemorrhage was rarely observed in the vicinity of groups of cells.

The main feature of all observed specimens was a moderate to severe disseminated embolization of alveolar and bronchiolar capillaries by a high number of injected cells (bone-forming cells A). The number of these cells as well as the number of occluded alveolar capillaries suggests that the gas exchange in the alveoli might have been severely disturbed leading to collapse of the respiratory system. It is very likely, that this process is responsible for the death of examined animals. Observed vascular congestion and microhemorrhage are interpreted as agonal changes.

No microthrombi were found to have formed in the heart, liver, kidney or spleen.

Example 6: In Vivo Bone Forming Properties of Bone-Forming Cells A and B Obtained by the Method of Example 1

Calvaria bone formation model consisted in a single subcutaneous administration of $2.5 \times 10^6$ bone forming cells formulated in 100 µl excipient (or 100 µl excipient alone as negative control) over the calvaria of 12-week-old female NMRI-Nude mice. At specific time points, calcium binding fluorescent dyes (i.e., alizarin red, green calcein, blue calcein, tetracycline) were administered to label neo-bone formation. Alizarin red was administered before bone forming cell administration whereas green calcein, blue calcein and tetracycline were administered after bone forming cell administration. Experimental animals were monitored for body weight, general clinical signs and clinical signs at site of administration during 2 weeks following the administration. After 2 weeks, experimental animals were euthanized to assess bone formation properties of bone forming cells by X-Ray imaging, histomorphometry (quantification of bone formation) and immunofluorescence.

1. Experimental Procedures 1.1 Cell Culture and Plasma Preparation

Cell culture and plasma preparation were performed as described in Example 1.

1.2 Mice

Female NMRI-Nude (nu/nu) mice of 9-10 weeks were purchased from Janvier S.A.S. (Le Genest-St-Isle, France) and housed in standard conditions with food and water ad libitum. 196 mice were used in total for the present study.

1.3 Calvaria Bone Formation Mouse Model

Twelve-week-old female NMRI-Nude (nu/nu) mice (n=137) were anesthetized with isoflurane (IsoFlo®) and received a single subcutaneous administration of MSC, bone-forming cells A (generated with FGF-2 and TGFβ1), or bone-forming cells B (generated with FGF-2, TGFβ1 and heparin) ($2.5 \times 10^6$ cells in 100 µl per mouse) or excipient (100 µl) over the calvaria bone. To label bone neo-formation over time, calcium-binding fluorochromes were sequentially administered to mice. Alizarin red (red), calceins (green and blue) and tetracycline (yellow) (all from Sigma-Aldrich®) were injected intraperitoneally 3 days before and 4, 8, and 12 days after cell administration, respectively. Experimental animals were monitored for body weight, general clinical signs, and clinical signs at site of administration for 2 weeks following the administration. Mice were euthanized 2 weeks after cell administration by cervical dislocation and the calvaria of each mouse was harvested to assess bone formation properties of bone forming cells by histomorphometry (quantification of bone formation) and immunofluorescence.

1.4 Sample Embedding and Histological Sectioning

For histomorphometry, ALP, TRAP (tartrate-resistant acid phosphatase), Masson Trichrome Goldner stainings and immunofluorescence, calvarias were fixed and dehydrated with successive incubations in 70%, 80% and 90% ethanol bath, for 12 hours each, at 4° C. with gentle shaking, and embedded in hydroxyethylmethacrylate (HEMA) plastic resin (HistoResin, Leica®). Four µm-thick and 8 µm-thick coronal sections were cut using a microtome (Leica, RM2255). For safranin-orange staining and immunoperoxidase, calvarias were fixed in 3.7% formaldehyde for 24 hours, decalcified in 10% ethylenediaminetetraacetic acid (EDTA) pH 7.4 for three days and embedded in paraffin. Seven µm-thick coronal and sagittal paraffin sections were cut using a microtome (Leica®, RM2255).

1.5. Immunofluorescence Staining

Assessment of the human and murine collagen I by immunofluorescence was performed on 4 µm-thick coronal plastic histological sections of calvaria. Briefly, after a step of permeabilization using a solution of PBS 1×/Triton 0.3% for 30 min at room temperature (RT), the histological sections were incubated for 1 hour at RT in the blocking solution (i.e., PBS/BSA/horse serum/Triton™) to sature non-specific binding sites. The histological slides were then incubated overnight at 4° C. with mouse anti-human and rabbit anti-murine collagen I primary antibodies (Abcam; #ab138492 and Abcam; #ab21286 respectively). After 3 steps of rinsing in PBS for 5 min at RT, blocking was realized with the blocking solution for 1 hour at RT. The secondary antibodies diluted in the blocking solution was then added for 2 hours at RT protected from the light. The secondary antibody Alexa Fluor® 488 Donkey anti-rabbit IgG H&L (ThermoFisher, #A21206) and Alexa Fluor® Cy3® Goat anti-mouse IgG H&L (Abcam; #ab97035) were used to visualize the murine collagen I in green and the human collagen I in red, respectively. The slides were then rinsed 3 times in PBS 1× for 5 min at RT and incubated with NucBlue® solution for 1 min at RT to stain the nucleus. Finally, the slides were briefly rinsed once in PBS then mounted in GlycerGel® reagent. As negative control of immunofluorescence, omission of primary antibody was performed on adjacent histological slide.

1.6 Histological Staining

Osteoblastic and osteoclastic activities were assessed on calvaria sections respectively using ALP and TRAP enzymatic activity detection methods respectively. For ALP staining, 4 µm-thick calvaria coronal plastic sections were incubated for 1 hour with a solution of Fast Blue RR Salt (Sigma-Aldrich®) and Naphtol AS-MX phosphate alkaline (Sigma-Aldrich®). TRAP staining was performed on 8 µm-thick calvaria coronal plastic sections using the Acid Phosphatase, Leukocyte (TRAP) Kit, (Sigma-Aldrich®) according to manufacturer's instructions. To assess the status of mineralization of the neo-formed bone, Masson Trichrome Goldner staining was performed on the calvaria sections stained with ALP using a kit (Bio-Optica®) according to manufacturer's instructions. To evidence cartilage formation, safranin-orange staining was performed on 7 µm-thick calvaria sagittal paraffin sections. Briefly, after deparaffinization, histological sections were successively incubated in Weigert's Hematoxylin (Klinipath®) for 10 min, 0.1% Fast Green (Klinipath®) for 5 min, 1% acetic acid (VWR Chemicals) for 15 sec and 0.1% safranin-orange (Fluka® ref: 84120) for 5 min. After dehydration, slides were mounted with glass coverslips using Pertex® (Histo-Lab®). Digital images were taken with an optical microscope (Leica) and the Leica® LAS EZ software.

1.7 Immunoperoxidase

After deparaffinization, 7 µm-thick calvaria coronal or sagittal paraffin sections were successively incubated with 2.5% hyaluronidase (Sigma-Aldrich®) for 30 min at 37° C., in 3% H2O2 (Sigma-Aldrich®) for 30 min at room temperature, in PBS containing 0.3% Triton X-100 (Sigma-Aldrich®) for 30 min at room temperature, and in blocking solution (i.e., PBS/BSA/horse serum/Triton) for 1 hour at RT at room temperature. Sections were incubated overnight at 4° C. with mouse anti-human type I collagen primary antibodies (Abcam, ab90395), rabbit anti-murine type I collagen primary antibodies (Abcam, ab21286) or with rabbit anti-Ku80 primary antibodies (Abcam, ab80592). Staining was visualized using a Vectastain kit (Vector Laboratories, PK6200) and 3,3' diaminobenzidine (Vector Laboratories), according to manufacturer's instructions. Sections were counterstained with Mayer's Hematoxylin (Klinipath®). Slides were mounted with glass coverslips using Pertex®.

1.8 Histomorphometrical Analyses of Calvarias: Quantification of Bone Formation

Quantification of bone formation (i.e., percentage of bone formation) was performed on plastic embedded tissues. Measures of the initial (basal mineralization front fluorescently labelled by alizarin red) and final thickness (neo-bone formation fluorescently labelled by calcein and tetracycline) of the calvaria were measured (in µm) on 4 µm-thick coronal section by ZENimage analysis software (Zeiss). The initial and final thicknesses of the calvaria were then used to calculate the percentage of neo-bone formation in each experimental animal following administration. For each animal, 4 measurements of initial and final thicknesses were performed on 5 independent levels, with a distance of 200 µm between each level. As the first step, mean of initial and final thickness±SD (i.e., mean of the 4 measures per level on the 5 levels) were calculated for each animal. Next, the percentage of bone formation for each mouse was calculated as the ratio of the mean of final thickness to the mean of initial thickness.

1.9 Quantification of the Surface Area of Neo-Formed Bone on Histological Images (ImageJ® software)

For the surface area analysis of osteoinduction and osteogenic nodules, digital images of 6 independent levels taken every 2 levels after the coronal suture were taken from plastic resin histological sections (4 µm) of calvaria, using a combination of multiple fluorescence and brightfield filters of the fluorescent microscope (Zeiss Axioscope A1, Zeiss, Germany). On each measured level, the selection of the osteoinducted bone neo-formation was manually defined in brightfield stiches images using ImageJ® software. The mineralized and total surface areas of this selection were measured (in $mm^2$). The same procedure was performed for the mineralized and total surface areas of the osteogenic nodules.

For the osteoinduction and the ostegenic nodules, the mean of the total surface area and the mean of the mineralized surface area was then calculated per experimental animal and per group. The total surface area of the bone neo-formation was finally calculated as the sum of the osteoinduction and osteogenic nodules surface areas.

1.10 Statistical Analyses

Results are expressed as means±standard error of the mean (SEM). Statistical analyses were performed using JMP® software (SAS Institute Inc.). For in vitro data (flow cytometry, RT-qPCR and multiplex), paired-t tests were performed on log 10 transformed values and for in vivo data, Mann-Whitney U tests were used. Unless indicated otherwise, differences between groups were considered statistically significant when $p<0.05$.

2. Results

Figure 9:
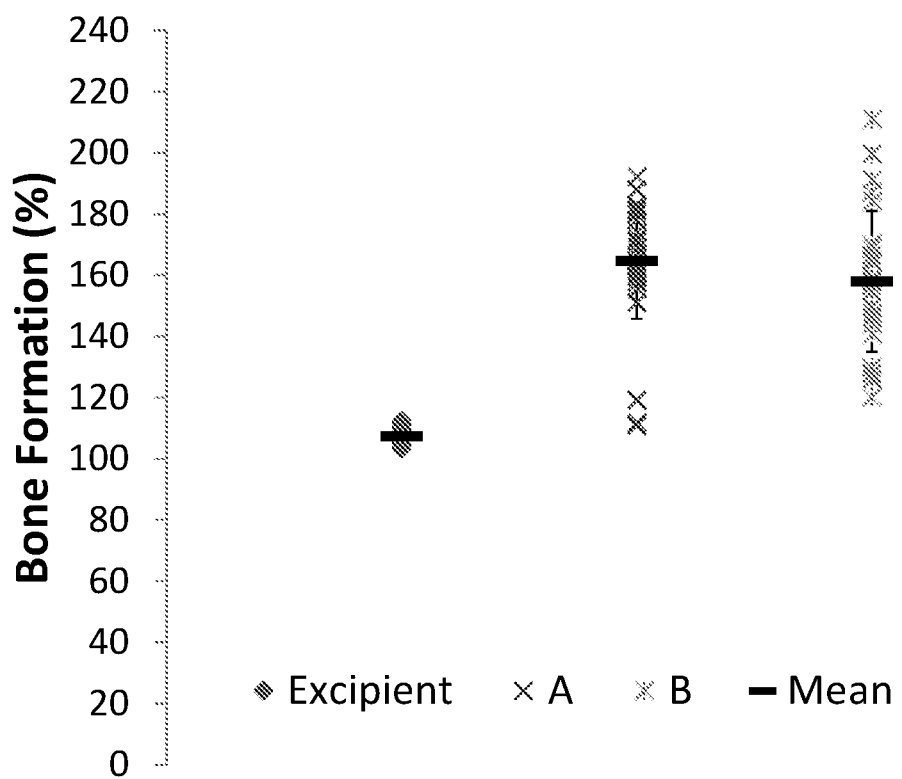
FIG. 9 illustrates the quantification of bone formation (%) performed on murine calvaria coronal sections, 2 weeks after administration of excipient alone (negative control), MSC-derived bone-forming cells A (generated with FGF-2 and TGFβ1) or MSC-derived bone-forming cells B (generated with FGF-2, TGFβ1 and heparin).

Both bone-forming cells A (generated with FGF-2 and TGFβ1) and bone-forming cells B (generated with FGF-2, TGFβ1 and heparin) showed significant higher bone formation than controls (excipient) 2 weeks after administration (FIGS. 8-9, Table 17). More particularly, FIG. 10 shows that bone-forming cells B displayed osteoinductive properties (homogenous bone formation from murine origin over the calvaria), and osteogenic properties (mineralized nodules from human and murine origins).

TABLE 17

Quantification of bone formation (%) on murine calvaria slices. Murine calvaria have been treated with excipient (negative control), bone-forming cells A or bone-forming cells B.

|  | Nb. of batches | Nb. of animals | % of bone formation Mean ± SD |
|---|---|---|---|
| Excipient | — | 59 | 107 ± 2 |
| Bone-forming cells A | 10 | 39 | 165 ± 19 |
| Bone-forming cells B | 7 | 30 | 158 ± 23 |

Abbreviations: SD: standard deviation

Osteoinductive properties (i.e., quantity of murine bone newly formed post-implantation) were equivalent for bone-forming cells A and B (FIGS. 8-9).

Very interestingly, the bone-forming cells B of the present invention displayed potent osteogenic properties and osteoinductive properties as shown by the high quantity of human and murine bone newly formed post-implantation (human and murine Coll IF staining, FIG. 10).

The presence of nodules was observed in 7/8 donors and 80% of mice of bone-forming cells B and in 4/11 donors and 20% of mice for bone-forming cells A. No nodule was observed after MSC or excipient administration. In addition to osteoinduction activities, bone-forming cells B thus promote a high osteogenic activity highlighted by the presence of large mineralized nodules observed in 80% of treated mice while bone-forming cells A display weak osteogenic activity i.e., small nodules in only 20% of treated mice (Table 18).

TABLE 18

Quantification of the presence of mineralized nodules on murine calvaria two weeks after administration over the calvaria of excipient, MSC, bone-forming cells A or bone-forming cells B

| Osteogeny occurrence | Donor | Batch | Animal |
|---|---|---|---|
| Excipient | NA | NA | 0/32 (0%) |
| MSC | 0/2 | 0/2 | 0/14 (0%) |
| Bone-forming cells A | 4/10 (40%) | 4/11 (36%) | 9/45 (20%) |
| Bone-forming cells B | 7/8 (88%) | 7/8 (88%) | 37/46 (80%) |

Abbreviations: MSC: mesenchymal stem cells; NA: not applicable

The histology staining of murine bone calvaria coronal sections two weeks after administration (excipient only, MSC, bone-forming cells A (generated with FGF-2 and TGFβ1; b-f cells A) or bone-forming cells B (generated with FGF-2, TGFβ1 and heparin; b-f cells B)) revealed that all treated conditions (MSC, b-f cells A and b-f cells B) have a high osteoinduction potential with a medium remodeling activity (ALP and TRAP staining) in the bone formed by osteoinduction.

Interestingly, the mineralized nodules observed in mice treated with bone-forming cells B were constituted of both murine (host) and human (donor) bone tissues (evidenced by human and murine type I collagen staining) demonstrating that the nodules were formed by both bone formation processes: osteogeny (donor bone formation) and osteoinduction process (host bone formation). In addition to a high osteoblast and osteoclast activities (ALP+TRAP staining), the nodules exhibited osteoid tissue (non-mineralized tissue) suggesting that bone formation was still progressing two weeks after administration, while the osteoinduction process observed in all conditions was already completed (FIG. 12).

FIG. 12 shows that human bone formation (i.e., osteogeny) (observed with anti-human type I collagen staining), and high osteoblast and osteoclast activities (observed with ALP+Goldner staining and TRAP staining respectively) were detected mostly in nodules of mice administered with bone-forming cells B, thereby showing that the bone formation process in the nodules was ongoing and was not completed at 2 weeks, unlike the osteoinduction process of MSC and bone-forming cells A that seemed completed. All treated conditions (MSC, b-f cells A, b-f cells B) had a high osteoinduction potential with a moderate remodeling activity (ALP and TRAP staining) in the osteoinducted bone formation (FIG. 12).

Figure 13:
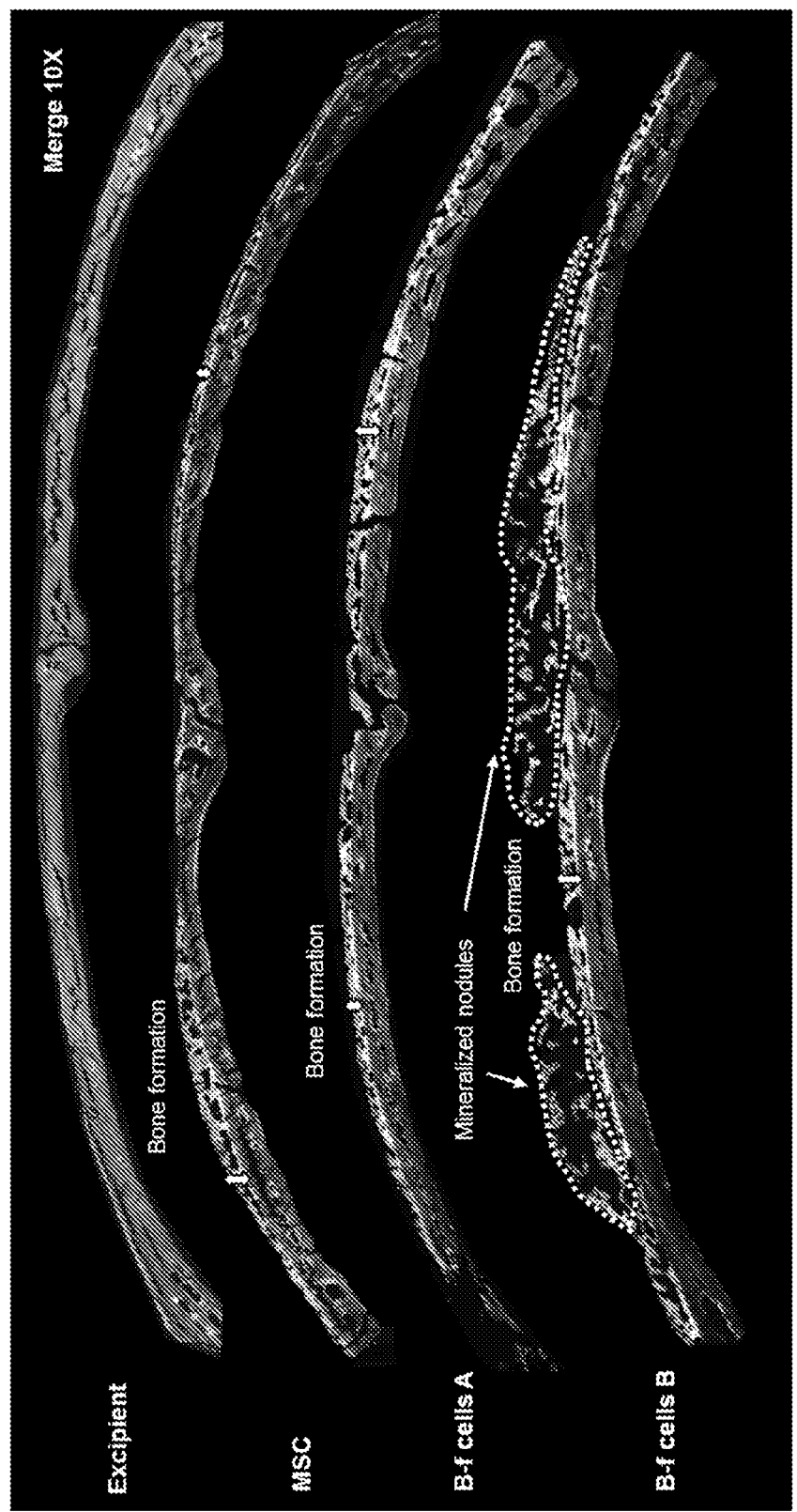
FIG. 13 represents photographs illustrating the bone neo-formation on murine bone calvaria coronal sections 2 weeks after administration of excipient alone; MSC; MSC-derived bone-forming cells A generated with FGF-2, TGFβ1 (b-f cells A); or MSC-derived bone-forming cells B generated with FGF-2, TGFβ1 and heparin (b-f cells B). The bone neo-formation is evidenced by fluorescence (labeled by the sequential integration of different fluorochromes: alizarin-red→calcein green→calcein blue→tetracycline yellow). Red, green and blue staining appears in light grey and bone neo-formation thickness is indicated with double arrows. Yellow staining has been surrounded by dotted lines.

The bone neo-formation was assessed by fluorescence two weeks after treatment with excipient only, MSC, b-f cells A or b-f cells B (FIG. 13). To this end, at specific time points, bone calcium binding fluorescent dyes (i.e., alizarin red, calcein green and blue, tetracycline yellow) were administered to the mice to label the neo-formed bone. The last fluorochrome to be administrated was tetracycline, administrated 12 days after administration of the cells.

As shown in FIG. 13, the nodules of the mice administered with bone forming cells B were mostly stained by tetracycline fluorochrome (yellow staining have been surrounded in dotted line in FIG. 13) confirming a later stage of formation compared to osteoinduction observed in the osteoinducted bone formation (alizarin red (red), calcein (green) and calecin blue (blue): these stainings appear in light grey and double arrows indicate the bone formation thickness).

The bone neo-formation of treated mice was assessed by quantification of the surface area of neo-formed bone on histological images (ImageJ® software). The total surface area of the neo-formed bone was determined by summing the osteo-induced and the bone nodule surface areas for each analyzed level and each mouse.

Figure 14:
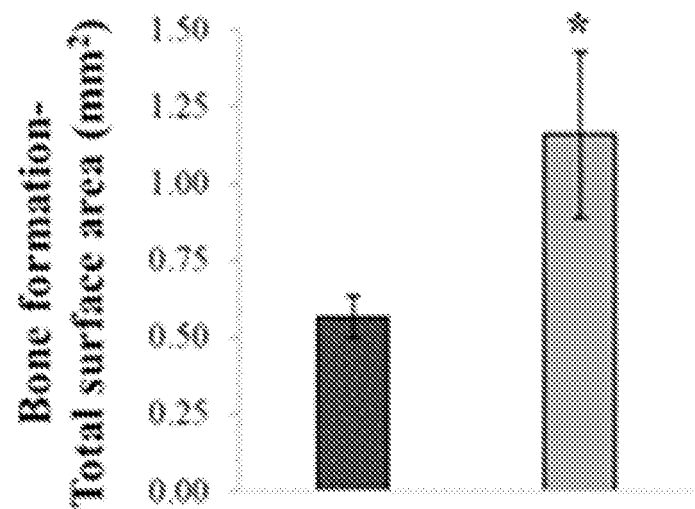
FIG. 14 represents a graph illustrating the total surface area of neo-formed bone (means±SEM, * p<0.05) measured on murine calvaria sections 2 weeks after administration of MSC (dark grey) or bone-forming cells B (light grey).

The results show that bone-forming cells B (n=7 mice, shown in FIG. 14 in light grey) significantly enhanced bone neo-formation 2 weeks after administration of the cells by about 2-fold compared to MSC (n=6 mice, shown in FIG. 14 in dark grey; Table 19). This difference was due to the high osteogeny property displayed by the bone-forming cells B and the absence of such property for MSC.

TABLE 19

Total bone neo-formation are measured on coronal sections
including the osteoinduction and the osteogenic formation

| Cell type (from the same donor) | Number of animals | Osteoinduction | | Osteogeny (nodules) | | Total (osteoinduction + osteogeny) | |
|---|---|---|---|---|---|---|---|
| | | Mineralized area (mm$^2$) (mean ± SD) | Total area (mm$^2$) (mean ± SD) | Mineralized area (mm$^2$) (mean ± SD) | Total area (mm$^2$) (mean ± SD) | Mineralized area (mm$^2$) (mean ± SD) | Total area (mm$^2$) (mean ± SD) |
| MSC | 6 | 0.42 ± 0.09 | 0.57 ± 0.17 | 0 | 0 | 0.42 ± 0.09 | 0.57 ± 0.17 |
| b-f cells B | 7 | 0.43 ± 0.16 | 0.59 ± 0.25 | 0.22 ± 0.19 | 0.57 ± 0.53 | 0.65 ± 0.30 | 1.16 ± 0.71 |

Abbreviations:
MSC: mesenchymal stem cells;
SD: standard deviation

Figure 15:
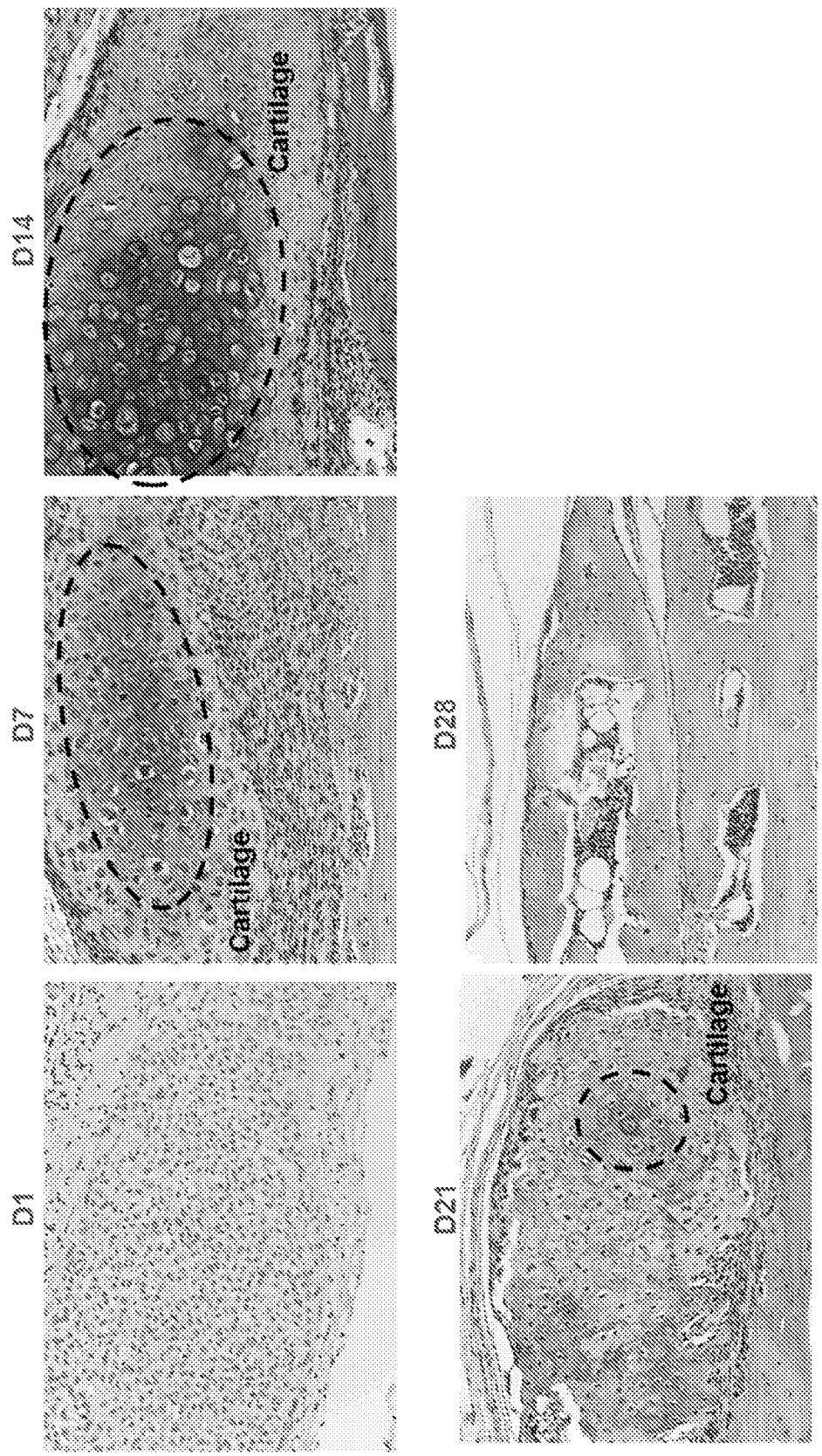
FIG. 15 illustrates safranin-orange staining of cartilaginous matrix (surrounded by dashes lines) of mineralized nodules performed on murine bone calvaria sagittal sections one day after the administration of bone-forming cells B (D1) and over time (D7, D14, D21) up to 28 days (D28) after administration.

Furthermore, the evaluation of the bone neo-formation over time using histological staining revealed that nodules observed on the top the calvaria of mice administered with bone-forming cells B were ossifying via an endochondral ossification mechanism. In FIG. 15, the safranin-orange staining shows proteoglycan (specific to cartilage) matrix (area surrounded by dashed lines); nuclei; bone tissue; and cytoplasm. Contrary to the osteo-induced bone that was produced by intramembranous ossification, bone nodules were produced through endochondral ossification, with cartilage matrix occurring between 1 week and 3 weeks after administration (FIG. 15).

Immunohistochemistry stainings targeting human type I collagen, murine type I collagen and human nucleus (i.e., Ku80) performed 4 weeks after the administration of bone-forming cells B confirmed the presence of human bone in the nodules. Moreover, Ku80 staining revealed that bone-forming cells B were engrafted in the bone matrix (nodules) and became osteocytes after in vivo administration.

Example 7: In Vivo Mouse Femoral Segmental Sub-Critical Size Defect (Sub-CSD) Repaired by Bone-Forming Cells B Obtained by the Method of Example 1

1. Experimental Procedures
1.1 Femoral Segmental Sub-Critical Size Defect (Sub-CSD) Model The surgical procedure was performed under aseptic conditions according to literature (Manassero et al., 2013, Tissue Engineering, Part C Methods, 19(4):271-80; Manassero et al., 2016, Journal of Visualized Experiments; (116): 52940). Briefly, 13-week-old female NMRI-Nude (nu/nu) mice (n=27) were anaesthetized with an intraperitoneal injection of a mix of dexmedetomidine hydrochloride (Dexdomitor, Orion Pharma, 1 mg/kg of body weight) and ketamine (Nimatek, Euronet, 150 mg/kg of body weight) and were placed in a ventral position on a warming plate. After applying a 6-hole titanium micro-locking plate (RI-System AG®) on the anterior side of the left femur, a 2-mm long mid-diaphyseal femoral osteotomy was performed using a Gigli saw and a jig (RSystem AG). As preventive medication, antibiotics (Baytril®, 10 mg/kg of body weight) were administered the day before the surgery (in drinking water) and analgesic (buprenorphine hydrochloride, Temgesic®, Schering-Plough, 0.1 mg/kg of body weight) was administered the day before the surgery and every 12 hours for at least 3 days following the surgery. MSC-derived cells (2.25×10$^6$ cells in a volume of 30 µl per mouse) or the excipient (control group) was administered on the day of the surgery (just after closing the wound with surgical sutures), locally at the site of the bone defect, by percutaneous injection using a 50 µl-Hamilton syringe. Mice were euthanized 6 weeks after cell or excipient administration by cervical dislocation. The left femur of each mouse was dissected, harvested and kept in 0.9% NaCl at room temperature until X-Ray imaging.

1.2 Quantification of Bone Repair by X-Ray Analyses

In vivo X-Ray imaging of the left femur of each mouse was performed, using the Faxitron MX-20 device just after the surgery to control the plate fixation, the segmental femoral defect size and to get a baseline, and every two weeks up to 6 weeks after administration of MSC-derived cells or excipient. Digital images were taken in mediolateral and anteroposterior views at a 4× magnification in manual mode with voltage set at 35 kV, exposure time at 4.8 sec, brightness at 4,300 and contrast at 7,100. Ex vivo X-Ray imaging was performed on left femurs harvested at euthanasia, 6 weeks after cell administration. Digital images were taken in mediolateral and anteroposterior views at a 5× magnification in manual mode with voltage set at 26 kV, exposure time at 15 sec, brightness at 4,850 and contrast at 6,850. The defect size was quantified for each mouse over time by measuring the distance (µm) between the two edges of the bone defect at three locations (right, middle and left of the defect) on mediolateral and anteroposterior X-Ray images, using ImageJ® software. The mean of the six measurements was calculated for each mouse at each time point.

1.3 Micro-Computed Tomography (Micro-CT) Analyses

After harvesting at euthanasia, the left femurs were fixed with 3.7% formaldehyde and transferred to the Center For Microscopy and Molecular Imaging (CMMI, ULB, Gosselies, Belgium) for micro-CT analyses. Samples were scanned using a multimodal microPET/CT nanoScan® PET/CT camera (Mediso) and the Nucline™ v2.01 software (Mediso). Scans were made using a semi-circular scan, the maximum zoom, a tube tension of 35 kVp, 720 projections per gantry rotation, an exposure time of 300 ms per projection, a detector pixel binning of 1 to 1. The scan lengths in the X and Y dimensions were adapted for each acquisition. The total duration of micro-CT scanning was 3 min 42 sec. Each micro-CT scan was post-reconstructed with a cubic voxel of 40 µm-side using a Shepp-Logan filter and a multi-sampling mode of 8 regular samples. The dimensions of the X and Y images were adapted for each reconstruction. The size of the Z-images corresponded to the scan length defined for the acquisition. A qualitative evaluation of bone repair was performed on the micro-CT images after reorienting the bone with the Z-axis (scanner axis) and cropping the image from one proximal to the other proximal screw in the femoral bone on the Z-axis, and as narrow as possible in the transverse (X-Y) plane. Then, a 3D Maximum Intensity projection (MIP) rendering was produced. To quantitatively assess bone repair, a virtual cylinder of 2 mm-diameter and 2 mm-axial length was placed in the defect space on the micro-CT scans and the mean bone volume was evaluated in this cylinder by thresholding voxels with radiological intensity equal or higher than 1500 HU.

Figure 16A:
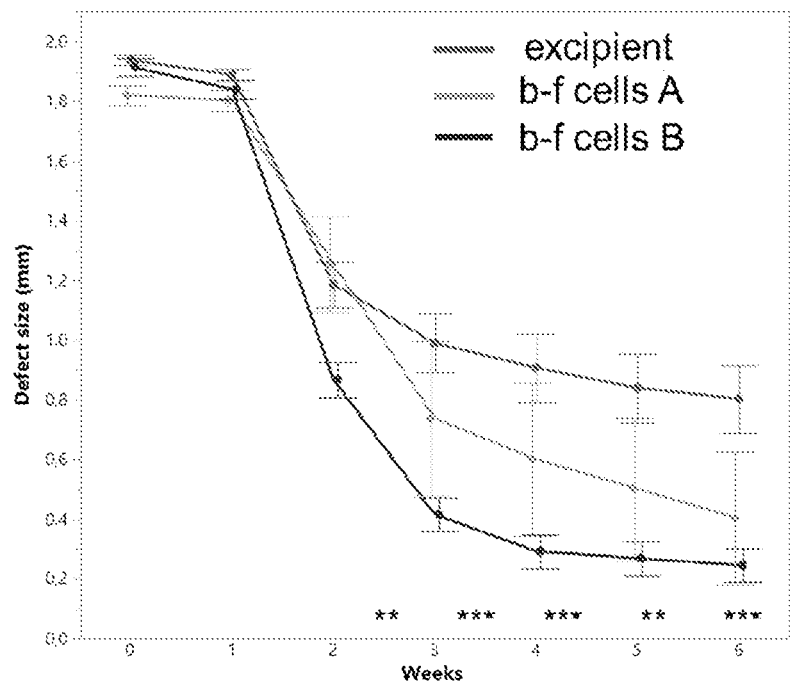
FIG. 16 illustrates the effect of MSC-derived cells in a segmental femoral sub-critical size defect model. (A) represents a graph illustrating the measurement of the defect size on X-Ray images on the day of the surgical procedure/item administration (D0) and over time (1, 2, 3, 4, 5 weeks) up to 6 weeks (6 W) after administration of the excipient alone, bone-forming cells A (b-f cells A) or bone-forming cells B (b-f cells B); means±SEM,  p<0.01, * p<0.001; (B) represents representative X-Ray images of segmental femoral defects at D0 and 6 W after administration of the excipient alone or bone-forming cells B (b-f cells B); (C) represents a graph illustrating the volume measurement of bone repair by micro-computed tomography (micro-CT) analyses at 6 W after administration of the excipient alone (n=7) and bone-forming cells B (n=8); mean SEM,* p<0.05.

2. Results 2.1 Bone-Forming Cells B Improved the Repair of Mice Femoral Sub-Critical Segmental Defect In the sub-critical size segmental defect (CSD) model in NMRI-Nude mice, bone-forming cells B (n=12 mice, 2 batches) improved fracture repair as shown by a significant reduction of the bone defect size compared to the excipient (n=11 mice), and to the bone-forming cells A (n=4 mice) from 2 to 6 weeks after administration (FIG. 16A).

Figure 16B:
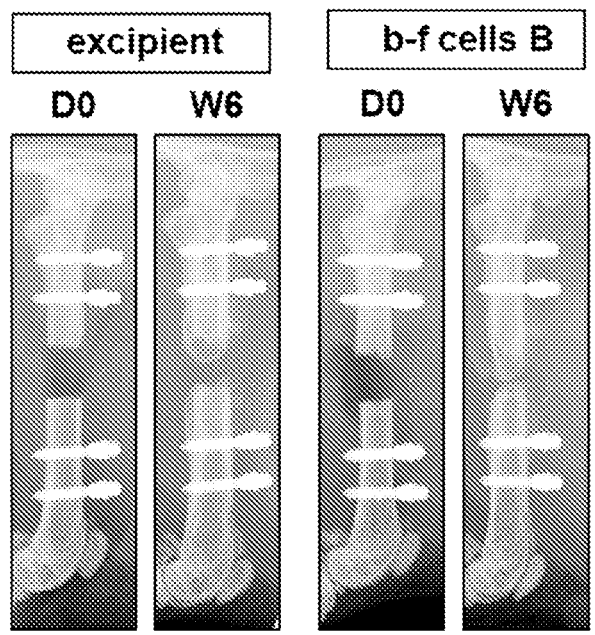

X-Ray images of segmental femoral defects at D0 and 6 W after administration of the excipient, bone-forming cells A (not shown) or bone-forming cells B showed a reduction of the bone defect size in mice administered with bone-forming cells B according to an embodiment of the invention compared to mice administered with the excipient (FIG. 16B) or bone-forming cells A (not shown).

Figure 16C:
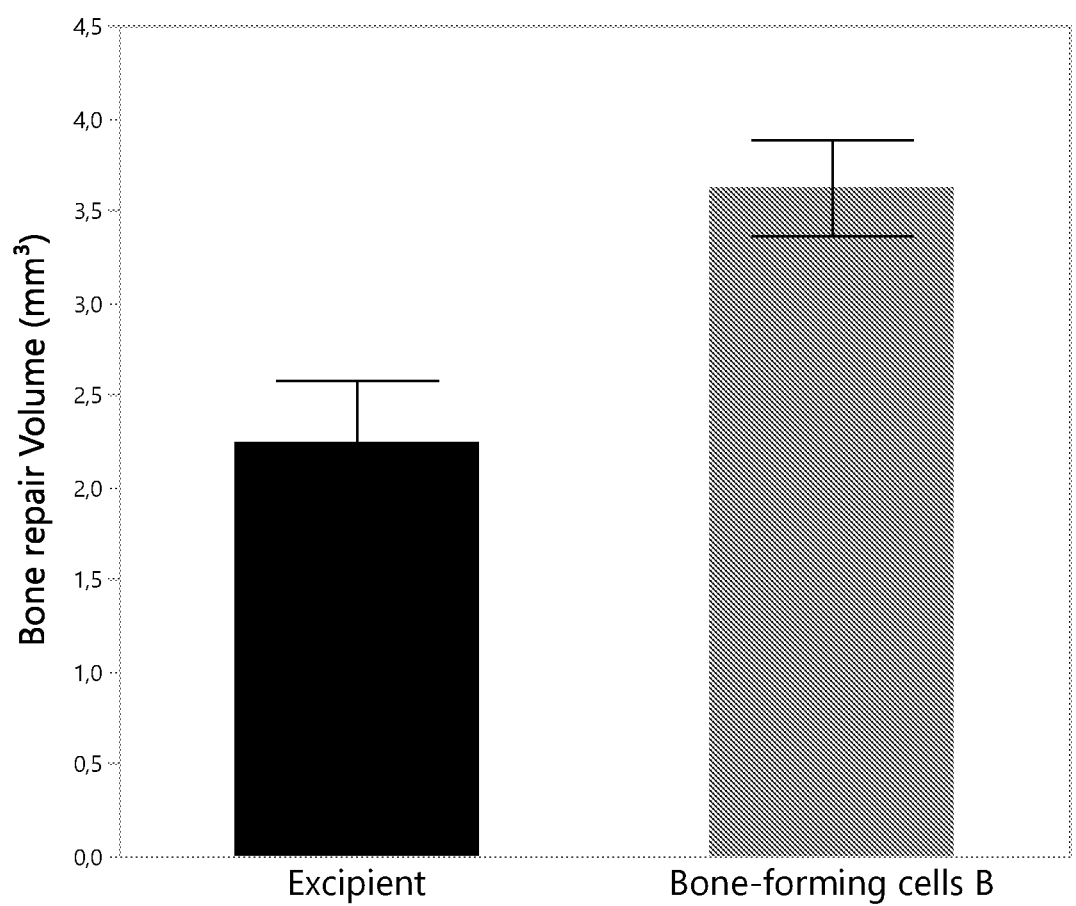

The bone repair volumes of segmental femoral defect were quantified by micro-computed tomography (micro-CT) analyses at 6 W after administration of the excipient and bone-forming cells B. The results confirmed that bone-forming cells B induced higher bone repair compared to excipient (FIG. 16C).

The invention claimed is:

1. A method for obtaining progenitor cells committed to the osteoblastic lineage from mesenchymal stem cells (MSC), the method comprising:
   differentiating MSC into progenitor cells committed to osteoblastic lineage by contacting the MSC in vitro or ex vivo with
   fibroblast growth factor-2 (FGF-2),
   transforming growth factor beta (TGFβ), and
   heparin or a derivative or analogue thereof at a concentration of at least 0.01 IU/ml; and
   harvesting the progenitor cells committed to the osteoblastic lineage so as to obtain a substantially pure population of the progenitor cells committed to the osteoblastic lineage;
   wherein the progenitor cells committed to the osteoblastic lineage have the ability to differentiate into cells of the osteoblastic lineage.

2. The method according to claim 1, wherein the progenitor cells committed to the osteoblastic lineage are osteoprogenitors or pre-osteoblasts.

3. The method according to claim 1, wherein the substantially pure population of progenitor cells committed to the osteoblastic lineage comprises at least 90% by number progenitor cells committed to the osteoblastic lineage.

4. The method according to claim 1, wherein the substantially pure population of progenitor cells committed to the osteoblastic lineage comprises at least 95% by number progenitor cells committed to the osteoblastic lineage.

5. The method according to claim 1, wherein the the substantially pure population of progenitor cells committed to the osteoblastic lineage comprises progenitor cells committed to the osteoblastic lineage at a concentration between about $1\times10^7$/ml and about $1\times10^8$/ml of the population.

6. The method according to claim 1, wherein the progenitor cells committed to the osteoblastic lineage comprise increased expression of a gene encoding an osteoblastic marker selected from the group consisting of Runt-related transcription factor 2 (RUNX2), alkaline phosphatase, biomineralization associated (ALPL), bone morphogenetic protein 2 (BMP2), osteoprotegerin (OPG), periostin (POSTN), cell adhesion molecule 1 (CADM1), connexin 43 (CX43), membrane metalloendopeptidase (CD10), and WNT1 inducible signaling pathway 1 (WISP1) as compared to the expression of the respective gene in MSC.

* * * * *